(12) United States Patent
Gross et al.

(10) Patent No.: US 8,148,097 B2
(45) Date of Patent: Apr. 3, 2012

(54) SCREENING METHOD FOR IDENTIFICATION OF COMPOUNDS WITH CALCIUM-INDEPENDENT PHOSPHOLIPASE $A_2\beta$ ($IPLA_2\beta$) MODULATING ACTIVITY

(75) Inventors: Richard W. Gross, Chesterfield, MO (US); Christopher Jenkins, Richmond Heights, MO (US)

(73) Assignee: Washington University, St. Louis, MO (US)

( * ) Notice: Subject to any disclaimer, the term of this patent is extended or adjusted under 35 U.S.C. 154(b) by 494 days.

(21) Appl. No.: 12/269,515

(22) Filed: Nov. 12, 2008

(65) Prior Publication Data

US 2010/0068703 A1 Mar. 18, 2010

Related U.S. Application Data

(63) Continuation of application No. 11/539,141, filed on Oct. 5, 2006, now abandoned.

(60) Provisional application No. 60/723,685, filed on Oct. 5, 2005.

(51) Int. Cl.
   *C12Q 1/34* (2006.01)
(52) U.S. Cl. ........ 435/18; 435/6.13; 435/6.18; 435/183; 435/198
(58) Field of Classification Search ........................ None
   See application file for complete search history.

(56) References Cited

U.S. PATENT DOCUMENTS

| | | | |
|---|---|---|---|
| 4,239,780 A | 12/1980 | Wallach | |
| 4,917,826 A | 4/1990 | Johnson et al. | |
| 5,279,957 A | 1/1994 | Gross | |
| 5,322,776 A | 6/1994 | Knopf et al. | |
| 5,328,842 A | 7/1994 | Chiou et al. | |
| 5,354,677 A | 10/1994 | Knopf et al. | |
| 5,356,787 A | 10/1994 | Gross | |
| 5,466,595 A | 11/1995 | Jones et al. | |
| 5,527,698 A | 6/1996 | Knopf et al. | |
| 5,554,511 A | 9/1996 | Jones et al. | |
| 5,589,170 A | 12/1996 | Jones et al. | |
| 5,593,878 A | 1/1997 | Knopf et al. | |
| 5,840,511 A | 11/1998 | Jones et al. | |
| 5,976,854 A | 11/1999 | Jones et al. | |
| 6,274,140 B1 | 8/2001 | Jones et al. | |
| 6,291,490 B1 | 9/2001 | Young | |
| 6,858,421 B2 | 2/2005 | Kriz et al. | |
| 6,916,841 B2 | 7/2005 | Seehra et al. | |
| 7,112,325 B2 | 9/2006 | Jones et al. | |
| 7,195,888 B2 * | 3/2007 | Gross | 435/18 |
| 7,468,266 B2 | 12/2008 | Ryan | |
| 7,473,541 B2 | 1/2009 | Gross et al. | |
| 2004/0185519 A1 | 9/2004 | Gross | |
| 2005/0003388 A1 | 1/2005 | Gross et al. | |
| 2008/0031951 A1 | 2/2008 | Guichard et al. | |

OTHER PUBLICATIONS

Connelly et al., FEBS Letter, 1994, vol. 352, p. 285-290.*
Kudo, I., and Murakami, M. (2002) Prostaglandins Other Lipid Mediat 68-69, 3-58.
Scott, D. L., and Sigler, P. B. (1994) Adv Protein Chem 45, 53-88.
Tischfield, J. A. (1997) J Biol Chem 272, 17247-17250.
Leslie, C. C. (1997) J Biol Chem 272, 16709-16712.
Underwood, K. W., Song, C., Kriz, R. W., Chang, X. J., Knopf, J. L., and Lin, L. L (1998) J Biol Chem 273, 21926-21932.
Pickard, R. T., Strifler, B. A., Kramer, R. M., and Sharp, J. D. (1999) J Biol Chem 274, 8823-8831.
Chiba, H., Michibata, H., Wakimoto, K., Seishima, M., Kawasaki, S., Okubo, K., Mitsui, H., Torii, H., and Imai, Y. (2004) J Biol Chem 279, 12890-12897.
Andrews, D. L., Beames, B., Summers, M. D., and Park, W. D. (1988) Biochem J 252, 199-206.
Wolf, M. J., and Gross, R. W. (1996) J Biol Chem 271, 30879-30885.
Tang, J., Kriz, R. W., Wolfman, N., Shaffer, M., Seehra, J., and Jones, S. S. (1997) J Biol Chem 272, 8567-8575.
Mancuso, D. J., Jenkins, C. M., and Gross, R. W. (2000) J Biol Chem 275, 9937-9945.
Schaffer, J. E, and Lodish, H. F. (1994) Cell 79, 427-436.
Hall, A. M., Smith, A. J., and Bernlohr, D. A. (2003) J Biol Chem 278, 43008-43013.
Marszalek, J. R., Kitidis, C., Dararutana, A., and Lodish, H. F. (2004) J Biol Chem 279, 23882-23891.
Smith, S., Witkowski, A., and Joshi, a. K. (2003) Prog Lipid Res 42, 289-317.
Moon, Y. A., and Horton, J. D. (2003) J Biol Chem 278, 7335-7343.
Dircks, L., and Sul, H. S. (1999) Prog Lipid Res 38, 461-479.
Coleman, R. A., and Lee, D. P. (2004) Prog Lipid Res 43, 134-176.
Hiltunen, J. K., and Qin, Y. (2000) Biochim Biophys Acta 1484, 117-128.
Eaton, S., Bartlett, K., and Pourfarzam, M. (1996) Biochem J 320 ( Pt 2), 345-357.
Mannaerts, G. P., Van Veldhoven, P. P., and Casteels, M. (2000) Cell Biochem Biophys 32 Spring, 73-87.
Kakar, S. S., Huang, W. H., and Askari, A. (1987) J Biol Chem 262, 42-45.
Branstrom, R., Leibiger, I. B., Leibiger, B., Corkey, B. E., Berggren, P. O., and Larsson, O. (1998) J Biol Chem 273, 31395-31400.
Gribble, F. M., Proks, P., Corkey, B. E., and Ashcroft, F. M. (1998) J Biol Chem 273, 26383-26387.
Glick, B. S., and Rothman, J. E. (1987) Nature 326, 309-312.
Pfanner, N., Orci, L., Glick, B. S., Amherdt, M., Arden, S. R., Malhotra, V., and Rothman, J. E. (1989) Cell 59, 95-102.
Ostermann, J., Orci, L., Tani, K., Amherdt, M., Ravazzola, M., Elazar, Z., and Rothman, J. E. (1993) Cell 75, 1015-1025.
Fitzsimmons, T. J., McRoberts, J. A., Tachiki, K. H., and Pandol, S. J. (1997) J Biol Chem 272, 31435-31440.
Knudsen, J., Jensen, M. V., Hansen, J. K., Faergeman, N. J., Neergaard, T. B., and Gaigg, B. (1999) Mol Cell Biochem 192, 95-103.
Linder, M. E., and Deschenes, R. J. (2003) Biochemistry 42, 4311-4320.
Hertz, R., Magenheim, J., Berman, I., and Bar-Tana, J. (1998) Nature 392, 512-516.
Rajas, F., Gautier, A., Bady, I., Montano, S., and Mithieux, G. (2002) J Biol Chem 277, 15736-15744.

(Continued)

*Primary Examiner* — Kade Ariani
(74) *Attorney, Agent, or Firm* — Armstrong Teasdale LLP

(57) ABSTRACT

An in vitro screening method for identifying a compound with $iPLA_2\beta$ modulating activity.

8 Claims, 20 Drawing Sheets

OTHER PUBLICATIONS

Elholm, M., Dam, I., Jorgensen, C., Krogsdam, A. M., Hoist, D., Kratchmarova, I., Gottlicher, M., Gustafsson, J. A., Berge, R., Flatmark, T., Knudsen, J., Mandrup, S., and Kristiansen, K. (2001) J Biol Chem 276, 21410-21416.

Murakami, K., Ide, T., Nakazawa, T., Okazaki, T., Mochizuki, T., and Kadowaki, T. (2001) Biochem J 353, 231-238.

Forman, B. M., Chen, J., and Evans, R. M. (1997) Proc Natl Acad Sci U S A 94, 4312-4317.

Kliewer, S. A., Sundseth, S. S., Jones, S. A., Brown, P. J., Wisely, G. B., Koble, C. S., Devchand, P., Wahli, W., . Willson, T. M., Lenhard, J. M., and Lehmann, J. M. (1997) Proc Natl Acad Sci U S A 94, 4318-4323.

Xu, H. E., Lambert, M. H., Montana, V. G., Parks, D. J., Blanchard, S. G., Brown, P. J., Sternbach, D. D., Lehmann, J. M., Wisely, G. B., Willson, T. M., Kliewer, S. A., and Milburn, M. V. (1999) Mol Cell 3, 397-403.

Hunt, M. C., and Alexson, S. E. (2002) Prog Lipid Res 41, 99-130.

Gross, R. W. (1983) Biochemistry 22, 5641-5646.

Nocito, M., Roy, G. Villar, L. M. Palacios, C., Serrano, A., Alvarez-Cermeno, J. C., and Gonzalez-Porque, P. (1996) Biochim Biophys Acta 1299, 17-22.

Camp, L. A., Verkruyse, L. A., Afendis, S. J., Slaughter, C. A., and Hofmann, S. L. (1994) J Biol Chem 269, 23212-23219.

Soyombo, A. A., and Hofmann, S. L. (1997) J Biol Chem 272, 27456-27463.

Duncan, J. A., and Gilman, A. G. (1998) J Biol Chem 273, 15830-15837.

Hertz, R., Kalderon, B., Byk, T., Berman, I., Za'tara, G., Mayer, R., and Bar-Tana, J. (2005) J Biol Chem 280, 24451-24461.

Lehman, J. J., Brown, K. A., Ramanadham, S., Turk, J., and Gross, R. W. (1993) J Biol Chem 268, 20713-20716.

Wolf, M. J., Wang, J., Turk, J., and Gross, R. W. (1997) J Biol Chem 272, 1522-1526.

Atsumi, G., Tajima, M., Hadano, A., Nakatani, Y., Murakami, M., and Kudo, I. (1998) J Biol Chem 273, 13870-13877.

Ramanadham, S., Hsu, F. F., Zhang, S., Jin, C., Bohrer, A., Song, H., Bao, S., Ma, Z., and Turk, J. (2004) Biochemistry 43, 918-930.

Roshak, A. K., Capper, E. A., Stevenson, C., Eichman, C., and Marshall, L. A. (2000) J Biol Chem 275, 35692-35698.

Su, X., Mancuso, D. J., Bickel, P. E., Jenkins, C. M., and Gross, R. W. (2004) J Biol Chem 279, 21740-21748.

Ramanadham, S., Song, H., Hsu, F. F., Zhang, S., Crankshaw, M., Grant, G. A., Newgard, C. B., Bao, S., Ma, Z., and Turk, J. (2003) Biochemistry 42, 13929-13940.

Smani, T., Zakharov, S. I., Leno, E., Csutora, P., Trepakova, E. S., and Bolotina, V. M. (2003) J Biol Chem 278, 11909-11915.

Smani, T., Zakharov, S. I., Csutora, P., Leno, E., Trepakova, E. S., and Bolotina, V. M. (2004) Nat Cell Biol 6, 113-120.

Mancuso, D. J., Abendschein, D. R., Jenkins, C. M., Han, X., Saffitz, J. E., Schuessler, R. B., and Gross, R. W. (2003) J Biol Chem 278, 22231-22236.

Wolf, M. J., and Gross, R. W. (1996) J Biol Chem 271, 20989-20992.

Jenkins, C. M., Wolf, M. J., Mancuso, D. J., and Gross, R. W. (2001) J Biol Chem 276, 7129-7135.

Bolotina, V. M. (2004) Sci STKE 2004, pe34.

Randriamampita, C., and Tsien, R. Y. (1993) Nature 364, 809-814.

Randriamampita, C., and Tsien, R. Y. (1995) J Biol Chem 270, 29-32.

Hazen, S. L., and Gross, R. W. (1991) J Biol Chem 266, 14526-14534.

Hazen, S. L., and Gross, R. W. (1991) Biochem J 280 ( Pt 3), 581-587.

Jenkins, C. M., Han, X., Mancuso, D. J., and Gross, R. W. (2002) J Biol Chem 277, 32807-32814.

Cohen Simonsen, A., Bernchou Jensen, U., Faergeman, N. J., Knudsen, J., and Mouritsen, O. G. (2003) FEBS Lett 552, 253-258.

Chao, H., Martin, G. G., Russell, W. K., Waghela, S. D., Russell, D. H., Schroeder, F., and Kier, A. B. (2002) Biochemistry 41, 10540-10553.

Hazen, S. L., Stuppy, R. J., and Gross, R. W. (1990) J Biol Chem 265, 10622-10630.

Wessel, D., and Flugge, U. I. (1984) Anal Biochem 138, 141-143.

Laemmli, U. K. (1970) Nature 227, 680-685.

Nesterenko, M. V., Tilley, M., and Upton, S. J. (1994) J Biochem Biophys Methods 28, 239-242.

Gross, R. W. (1984) Biochim Biophys Acta 802, 197-202.

Hunt, M. C., Solaas, K., Kase, B. F., and Alexson, S. E. (2002) J Biol Chem 277, 1128-1138.

Hazen, S. L., Zupan, L. A., Weiss, R. H., Getman, D. P., and Gross, R. W. (1991) J Biol Chem 266, 7227-7232.

Zupan, L. A., Weiss, R. H., Hazen, S. L, Parnas, B. L., Aston, K. W., Lennon, P. J., Getman, D. P., and Gross, R. W. (1993) J Med Chem 36, 95-100.

O'Brien, P. J., St Jules, R. S., Reddy, T. S., Bazan, N. G., and Zatz, M. (1987) J Biol Chem 262, 5210-5215.

Duncan, J. A., and Gilman, A. G. (1996) J Biol Chem 271, 23594-23600.

Tu, Y., Wang, J., and Ross, E. M. (1997) Science 278, 1132-1135.

Ford, D. A., Homer, C. C., and Gross, R. W. (1998) Biochemistry 37, 11953-11961.

Schaller, J. (2000) Methods Mol Biol 146, 425-437.

Quach, T. T., Li, N., Richards, D. P., Zheng, J., Keller, B. 0., and Li, L. (2003) J Proteome Res 2, 543-552.

Zischka, H., Gloeckner, C. J., Klein, C., Willmann, S., Swiatek-de Lange, M., and Ueffing, M. (2004) Proteomics 4, 3776-3782.

Eichacker, L. A., Granvogl, B., Mirus, O., Muller, B. C., Miess, C., and Schleiff, E. (2004) J Biol Chem 279, 50915-50922.

Nowatzke, W., Ramanadham, S., Ma, Z., Hsu, F. F., Bohrer, A., and Turk, J. (1998) Endocrinology 139, 4073-4085.

Thomas, D., and Hanley, M. R. (1995) J Biol Chem 270, 6429-6432.

Han, X., and Gross, R. W. (1994) Proc Natl Acad Sci U S A 91, 10635-10639.

Wolf, R. A., and Gross, R. W. (1985) J Biol Chem 260, 7295-7303.

McHowat, J., and Creer, M. H. (1998) Am J Physiol 274, C447-454.

Murakami, M., Shimbara, S., Kambe, T., Kuwata, H., Winstead, M. V., Tischfield, J. A., and Kudo, I. (1998) J Biol Chem 273, 14411-14423.

Tessier, C., Hichami, A., and Khan, N. A. (2002) FEBS Lett 520, 111-116.

Ma, Z., Ramanadham, S., Wohltmann, M., Bohrer, A., Hsu, F. F., and Turk, J. (2001) J Biol Chem 276, 13198-13208.

Hazen, S. L., Ford, D. A., and Gross, R. W. (1991) J Biol Chem 266, 5629-5633.

Williams, S. D., and Gottlieb, R. A. (2002) Biochem J 362, 23-32.

Ma, Z., Ramanadham, S., Kempe, K., Chi, X. S., Ladenson, J., and Turk, J. (1997) J Biol Chem 272, 11118-11127.

Larsson Forsell, P. K., Kennedy, B. R, and Claesson, H. E. (1999) Eur J Biochem 262, 575-585.

Larsson, P. K., Claesson, H. E., and Kennedy, B. P. (1998) J Biol Chem 273, 207-214.

Atsumi, G., Murakami, M., Kojima, K., Hadano, A., Tajima, M., and Kudo, I. (2000) J Biol Chem 275, 18248-18258.

Lauber, K., Bohn, E., Krober, S. M., Xiao, Y. J., Blumenthal, S. G., Lindemann, R. K., Marini, P., Wiedig, C., Zobywalski, A., Baksh, S., Xu, Y., Autenrieth, I. B., Schulze-Osthoff, K., Belka, C., Stuhler, G., and Wesselborg, S. (2003) Cell 113, 717-730.

Tay, H. K., and Melendez, A. J. (2004) J Biol Chem 279, 22505-22513.

Wang, Z., Ramanadham, S., Ma, Z. A., Bao, S., Mancuso, D. J., Gross, R. W., and Turk, J. (2005) J Biol Chem 280, 6840-6849.

Jenkins, C. M., Han, X., Yang, J., Mancuso, D. J., Sims, H. F., Muslin, A. J., and Gross, R. W. (2003) Biochemistry 42, 11798-11807.

Lehner, R., and Kuksis, A. (1993) J Biol Chem 268, 24726-24733.

Liu, G. X., Hanley, P. J., Ray, J., and Daut, J. (2001) Circ Res 88, 918-924.

Rohacs, T., Lopes, C. M., Jin, T., Ramdya, P. P., Molnar, Z., and Logothetis, D. E. (2003) Proc Natl Acad Sci U S A 100, 745-750.

Mignen, O., Thompson, J. L., and Shuttleworth, T. J. (2003) J Biol Chem 278, 10174-10181.

Gubitosi-Klug, R. A., Yu, S. P., Choi, D. W., and Gross, R. W. (1995) J Biol Chem 270, 2885-2888.

Honore, E., Barhanin, J., Attali, B., Lesage, F., and Lazdunski, M. (1994) Proc Natl Acad Sci U S A 91, 1937-1941.

Hamilton, K. L., Syme, C. A., and Devor, D. C. (2003) J Biol Chem 278, 16690-16697.

Carattino, M. D., Hill, W. G., and Kleyman, T. R. (2003) J Biol Chem 278, 36202-36213.

Paucek, P., Yarov-Yarovoy, V., Sun, X., and Garlid, K. D. (1996) J Biol Chem 271, 32084-32088.

Bolotina, V. M., and Csutora, P. (2005) Trends Biochem Sci 30, 378-387.

Kim, Y. C., Gomez, F. E., Fox, B. G., and Ntambi, J. M. (2000) J Lipid Res 41, 1310-1316.

Resh, M. D. (1999) Biochim Biophys Acta 1451, 1-16.

Bijlmakers, M. J., and Marsh, M. (2003) Trends Cell Biol 13, 32-42.

Smotrys, J. E., and Linder, M. E. (2004) Annu Rev Biochem 73, 559-587.

Lopaschuk, G. D., and Russell, J. C. (1991) Myocardial function and energy substrate metabolism in the insulin-resistant JCR:LA corpulent rat, J. Appl. Physiol. 71, 1302-1308.

Han, X., Abendschein, D. R., Kelley, J. G., and Gross, R. W. (2000) Diabetes-induced changes in specific lipid molecular species in rat myocardium, Biochem. J. 352, 79-89.

Kraegen, E. W., Cooney, G. J., Ye, J. M., Thompson, A. L., and Furler, S. M. (2001) The role of lipids in the pathogenesis of muscle insulin resistance and beta cell failure in type II diabetes and obesity, Exp. Clin. Endocrinol. Diabetes 109 Suppl 2, S189-201.

Finck, B. N., Lehman, J. J., Leone, T. C., Welch, M. J., Bennett, M. J., Kovacs, A., Han, X., Gross, R. W., Kozak, R., Lopaschuk, G. D., and Kelly, D. P. (2002) the cardiac phenotype induced by PPAR overexpression mimics that caused by diabetes mellitus, J, Clin. Invest. 109, 12 1-130.

Kelley, D. E. (2002) Skeletal muscle triglycerides: an aspect of regional adiposity and insulin resistance, Ann. N. Y. Acad. Sci. 967, 135-145.

Unger, R. H. (2002) Lipotoxic diseases, Annu. Rev. Med. 53, 319-336.

Hung, T., Sievenpiper, J. L, Marchie, A., Kendall, C. W., and Jenkins, D. J. (2003) Fat versus carbohydrate in insulin resistance, obesity, diabetes and cardiovascular disease, Curr Opin Clin Nutr Metab Care 6, 165-176.

Finck, B. N., Han, X., Courtois, M., Aimond, F., Nerbonne, J. M., Kovacs, A., Gross, R. W., and Kelly, D. P. (2003) A critical role for PPARalpha-mediated lipotoxicity in the patbogenesis of diabetic cardiomyopathy: modulation by dietary fat content, Proc. Natl. Acad. Sci. U S. A, 100, 1226-1231.

Su, X., Han, X., Mancuso, D. J., Abendschein, D. R., and Gross, R. W. (2005) Accumulation of long-chain acylcarnitine and 3-hydroxy acylcarnitine molecular species in diabetic myocardium: identification of alterations in mitochondrial fatty acid processing in diabetic myocardium by shotgun lipidomics, Biochemistry 44, 5234-5245.

Han, X., and Gross, R. W. (2003) Global analyses of cellular lipidomes directly from crude extracts of biological samples by ESI mass spectrometry: a bridge to lipidomics, J. Lipid Res. 44, 1071-1079.

Han, X., and Gross, R. W. (2005) Shotgun lipidomics: Electrospray ionization mass spectrometric analysis and quantitation of the cellular lipidomes directly from crude extracts of biological samples, Mass Spectrom. Rev. 24, 367-412.

Han, X., and Gross, R. W. (2005) Shotgun lipidomics: multi-dimensional mass spectrometric analysis of cellular lipidomes, Expert Rev. Proteomics 2, 253-264.

Pulfer, M., and Murphy, R. C. (2003) Electrospray mass spectrometry of phospholipids, Mass Spectrom. Rev. 22, 332-364.

Welti, R., and Wang, X. (2004) Lipid species profiling: a high-throughput approach to identify lipid compositional changes and determine the function of genes involved in lipid metabolism and signaling, Curr. Op/n. Plant BioL 7, 337-344.

Forrester Jeffrey, S., Milne Stephen, B., Ivanova Pavlina, T., and Brown, H. A. (2004) Computational Lipidomics: A Multiplexed Analysis of Dynamic Changes in Membrane Lipid Composition during Signal Transduction, Mol. Pharmacol. 65, 813-821.

Ekroos, K., Chernushevich, I. V., Simons, K., and Shevchenko, A. (2002) Quantitative profiling of phospholipids by multiple precursor ion scanning on a hybrid quadrupole time-of-flight mass spectrometer, Anal. Chem. 74, 941-949.

Hermansson, M., Uphoff, A., Kakela, R., and Somerharju, P. (2005) Automated quantitative analysis of complex lipidomes by liquid chromatography/mass spectrometry, Anal. Chem. 77, 2166-2175.

Ishida, M., Yamazaki, T., Houjou, T., Imagawa, M., Harada, A., Inoue, K., and Taguchi, R. (2004) High-resolution analysis by nano-electrospray ionization Fourier transform ion cyclotron resonance mass spectrometry for the identification of molecular species of phospholipids and their oxidized metabolites, Rapid Commun. Mass Spectrom. 18, 2486-2494.

Han, X., Holtzman, D. M., and McKeel, D. W., Jr. (2001) Plasmalogen deficiency in early Alzheimer's disease subjects and in animal models: molecular characterization using electrospray ionization mass spectrometry, J. Neurochem. 77, 1168-1180.

Han, X., Holtzman, D. M., McKeel, D. W., Jr., Kelley, J., and Morris, J. C. (2002) Substantial sulfatide deficiency and ceramide elevation in very early Alzheimer's disease: potential role in disease pathogenesis, J. Neurochem. 82, 809-818.

Mancuso, D. J., Abendschein, D. R., Jenkins, C. M., Han, X., Saffitz, J. E., Schuessler, R. B., and Gross, R. W. (2003) Cardiac ischemia activates calcium-independent phospholipase A2β, precipitating ventricular tachyarrhythmias in transgenic mice: rescue of the lethal electrophysiologic phenotype by mechanism-based inhibition, J. BioL Chem. 278, 22231-22236.

Jain, S., Jayasimhulu, K., and Clark, J. F. (2004) Metabolomic analysis of molecular species of phospholipids from normotensive and preeclamptic human placenta electrospray ionization mass spectrometry, Front. Biosci. 9, 3167-3175.

Sparagna, G. C., Johnson, C. A., McCune, S. A., Moore, R. L., and Murphy, R. C. (2005) Quantitation of cardiolipin molecular species in spontaneously hypertensive heart failure rats using electrospray ionization mass spectrometry, J. Lipid Res. 46, 1196-1204.

Vreken, P., Valianpour, F., Nijtmans, L. G., Grivell, L. A., Plecko, B., Wanders, R. J., and Barth, P. G. (2000) Defective remodeling of cardiolipin and phosphatidylglycerol in Barth syndrome, Biochem. Biophys. Res. Commun. 279, 378-382.

Schlame, M., Towbin, J. A., Heerdt, P. M., Jehle, R., DiMauro, S., and Blanck, T. J. (2002) Deficiency of tetralinoleoylc-ardiolipin in Barth syndrome, Ann. Neurol. 51, 634-637.

Valianpour, F., Wanders, R. J., Overmars, H., Vreken, P., Van Gennip, A. H., Baas, F., Plecko, B., Santer, R., Becker, K., and Barth, P. G. (2002) Cardiolipin deficiency in Xlinked cardioskeletal myopathy and neutropenia (Barth syndrome, MIM 302060): a study in cultured skin fibroblasts, J. Pediatr. 141, 729-733.

Barth, P. G., Valianpour, F., Bowen, V. M., Lam, J., Duran, M., Vaz, F. M., and Wanders, R. J. (2004) X-linked cardioskeletal myopathy and neutropenia (Barth syndrome): an update, Am J Med Genet a 126, 349-354.

Gu, Z., Valianpour, F., Chen, S., Vaz, F. M., Hakkaart, G. A., Wanders, R. J., and Greenberg, M. L. (2004) Aberrant cardiolipin metabolism in the yeast tazl mutant: a model for Barth syndrome, MoL MicrobioL 51, 149-158.

Han, X., Yang, J., Cheng, H., Ye, H., and Gross, R. W. (2004) Towards fingerprinting cellular lipidomes directly from biological samples by two-dimensional electrospray ionization mass spectrometry, Anal. Biochem. 330, 317-331.

Bligh, E. C., and Dyer, W. J. (1959) A rapid method of total lipid extraction and purification, Can. J. Biochem. Physiol. 37,911-917.

Le Belle, J. F., Harris, N. G., Williams, S. R., and Bhakoo, K. K. (2002) A comparison of cell and tissue extraction techniques using high-resolution 1H-NMR spectroscopy, NMR Biomed. 15, 37-44.

Gibon, Y., Vigeolas, H., Tiessen, A., Geigenberger, P., and Stitt, M. (2002) Sensitive and high throughput metabolite assays for inorganic pyrophosphate, ADPGlc, nucleotide phosphates, and glycolytic intermediates based on a novel enzymic cycling system, Plant J. 30, 221-235.

Schlame, M., and Haldar, D. (1993) Cardiolipin is synthesized on the matrix side of the inner membrane in rat liver mitochondria, J Biol. Chem. 268, 74-79.

Mandieau, V., Martin, I., and Ruysschaert, J. M. (1995) Interaction between cardiolipin and the mitochondrial presequence of cytochrome c oxidase subunit IV favours lipid mixing without destabilizing the bilayer structure, FEBS Lett. 368, 15-18.

Zhang, M., Mileykovskaya, E., and Dowhan, W. (2002) Gluing the respiratory chain together. Cardiolipin is required for supercomplex formation in the inner mitochondrial membrane, J. Biol. Chem. 277, 43553-43556.

Pfeiffer, K., Gohil, V., Stuart, R. A., Hunte, C., Brandt, U., Greenberg, M. L., and Schagger, H. (2003) Cardiolipin stabilizes respiratory chain supercomplexes, J. Biol. Chem. 278, 52873-52880.

McMillin, J. B., and Dowhan, W. (2002) Cardiolipin and apoptosis, Biochim. Biophys. Acta 1585, 97-107.

Degli Esposti, M. (2004) Mitochondria in apoptosis: past, present and future, Biochem. Soc. Trans. 32, 493-495.

Ostrander, D. B., Sparagna, C. C., Amoscato, A. A., McMillin, J. B., and Dowhan, W. (2001) Decreased cardiolipin synthesis corresponds with cytochrome c release in palmitate-induced cardiomyocyte apoptosis, J. Biol. Chem. 276, 38061-38067.

Ortiz, A., Killian, J. A., Verkleij, A. J., and Wilschut, J. (1999) Membrane fusion and the lamellar-to-inverted-hexagonal phase transition in cardiolipin vesicle systems induced by divalent cations, Biophys. 1. 77, 2003-2014.

Bossy-Wetzel, E., Barsoum, M. J., Godzik, A., Schwarzenbacher, R., and Lipton, S. A. (2003) Mitochondrial fission in apoptosis, neurodegeneration and aging, Curr. Opin. Cell Biol. 15, 706-7 16.

Xu, Y., Kelley, R. I., Blanek, T. J., and Schlame, M. (2003) Remodeling of cardiolipin by phospholipid transacylation, J. Biol. Chem. 278, 51380-51385.

Vaz, F. M., Houtkooper, R. H., Valianpour, F., Barth, P. G., and Wanders, R. J. (2003) Only one splice variant of the human TAZ gene encodes a functional protein with a role in cardiolipin metabolism, J. Biol. Chem. 278, 43089-43094.

Lopaschuk, G. D., Tahiliani, A. G., Vadlamudi, R. V., Katz, S., and McNeill, J. H. (1983) Cardiac sarcoplasmic reticulum function in insulin- or carnitine-treated diabetic rats, Am. J. Physiol. 245, H969-976.

Katz, F. B., Stenbit, A. E., Hatton, K., DePinho, R., and Charron, M. J. (1995) Cardiac and adipose tissue abnormalities but not diabetes in mice deficient in GLUT4, Nature 377, 151-155.

Stenbit, A. F., Tsao, T. S., Li, J., Burcelin, R., Geenen, D. L., Factor, S. M., Houseknecht, K., Katz, F. B., and Charron, M. J. (1997) GLUT4 heterozygous knockout mice develop muscle insulin resistance and diabetes, Nat. Med. 3, 1096-1101.

Dhalla, N. S., Liu, X., Panagia, V., and Takeda, N. (1998) Subcellular remodeling and heart dysfunction in chronic diabetes, Cardiovasc. Res. 40, 239-247.

Godin, D.V., Lopaschuk, G.D., and McNeill, J.H. (1986) Subcellular myocardial abnormalities in experimental diabetes: role of long-chain acylcarnitines, Can. J. Cardiol. 2, 222-229.

Valianpour, F., Wanders, R. J., Overmars, H., Vaz, F.M., Barth, P. G., and van Gennip, A. H. (2003) Linoleic acid supplementation of Barth syndrome fibroblasts restores cardiolipin levels: implications for treatment, J. Lipid Res. 44, 560-566.

Broekemeier, K. M., Iben, J. R., LeVan, E. G., Crouser, E. D., and Pfeiffer, D.R. (2002) Pore formation and uncoupling initiate a Ca2+-independent degradation of mitochondrial phospholipids, Biochemistry 41, 7771-7780.

Han, X., and Gross, R. W. (1990) Plasmenylcholine and phosphatidylcholine membrane bilayers possess distinct conformational motifs, Biochemistry 29, 4992-4996.

Samuelsson et al., Annu. Rev. Biochem. 47:997-1029, (1978).

Moolenaar, W.H., Curr. Opin. Cell. Biol. 7:203-10, (1995).

Needleman et al., Annu. Rev. Biochem. 55:69-102, (1986).

Demel et al, Biochim. Biopliys. Acta 406:97-107, (1975).

Demel et al., supra; Tischfield, J.A., J. Biol. Chem. 272:17247-50, (1997).

Loeb et al., J. Biol. Chem. 261:10467-70, (1986).

Kramer et al., Biochim. Biophys. Acta 878:394-403.

Glover et al., J. Biol. Chem. 270:15359-67, (1986).

Wolf et al., J. Biol. Chem. 260:7295-303.

Hirashima et al., J. Neurochem. 59:708-14.

Lehman et al., J. Biol. Chem. 268:20713-16.

Evenberg et al., J. Biol. Chem. 252: 1189-96, (1977).

Tischfeld, J.A., J. Biol. Chem. 272: 17247-50, (1997).

Andrews et al., Biochem. J. 252:199-206, (1988).

Tang et al., J. Biol. Chem. 272:8567-75, (1998).

Underwood et al., J. Biol. Chem. 273: 21926-32, (1998).

Pickard et al., J Biol. Chem. 274: 8823-31, (1999).

Van der Vusse et al., Hydrolysis of phospholipids and cellular integrity, In: H.M. Piper (ed.) Pathophysiology of Severe Ischemic Myocardial injury, Kluwer Academic Publishers, Dordrecht, The Netherlands, 1990, 167-93.

Farooqui et al., Neurochem. Int. 30: 5 17-22, (1997).

Farooqui et al., Brain Res. Bull. 49: 139-53, (1999).

Sambrook et al., 1989, Molecular Cloning, a Laboratory Manual, Cold Spring Harbor Press, N.Y.

Rosenberg et al., Science 242:1575-1578 (1988).

Wolff et al., PNAS 86:9011-9014 (1989).

Caplen et al., Nature Med., 1:39-46 (1995).

Zhu et al., Science, 261:209-211 (1993).

Berkner et al., Biotechniques, 6:616-629 (1988).

Trapnell et al., Advanced Drug Delivery Rev., 12:185-199 (1993).

Hodgson et al., BioTechnology 13:222 (1995).

Jenkins et al., The Journal of Biological Chemistry, Nov. 2004, vol. 279, No. 47, pp. 48968-48975.

Hosteller et al., JBC, May 2005, vol. 280, No. 19, pp. 18667-18682.

Zeviani & Spinazzola, Current Neurology & Neuroscience reports, 2003, vol. 3, pp. 423-232.

Schlame, M., Towbin, J.A., Heerdt, P.M., Jehle, R., DiMauro, S., and Blanck, T.J. (2002) Deficiency of Tetralinoleoyl-cardiolipin in Barth Syndrome, Ann. Neurol. 51, 634-637.

* cited by examiner

SEQUENCE LISTING

```
<160> NUMBER OF SEQ ID NOS: 13

<210> SEQ ID NO 1
<211> LENGTH: 752
<212> TYPE: PRT
<213> ORGANISM: Homo sapiens

<400> SEQUENCE: 1

Met Gln Phe Phe Gly Arg Leu Val Asn Thr Phe Ser Gly Val Thr Asn
 1               5                  10                  15

Leu Phe Ser Asn Pro Phe Arg Val Lys Glu Val Ala Val Ala Asp Tyr
             20                  25                  30

Thr Ser Ser Asp Arg Val Arg Glu Glu Gly Gln Leu Ile Leu Phe Gln
         35                  40                  45

Asn Thr Pro Asn Arg Thr Trp Asp Cys Val Leu Val Asn Pro Arg Asp
     50                  55                  60

Ser Gln Ser Gly Phe Arg Leu Phe Gln Leu Glu Leu Glu Ala Asp Ala
 65                  70                  75                  80

Leu Val Asn Phe His Gln Tyr Ser Ser Gln Leu Leu Pro Phe Tyr Glu
                 85                  90                  95

Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
        115                 120                 125

Leu Gly Ile Arg Glu Cys Phe His His Ser Arg Ile Ile Ser Cys Ala
    130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
        195                 200                 205

Ala Val Ala Gly Leu Asn Gln Val Asn Asn Gln Gly Leu Thr Pro Leu
    210                 215                 220
```

```
His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
            245                 250                 255

His Ser Ala Met Lys Phe Ser Gln Lys Gly Cys Ala Glu Met Ile Ile
        260                 265                 270

Ser Met Asp Ser Ser Gln Ile His Ser Lys Asp Pro Arg Tyr Gly Ala
    275                 280                 285

Ser Pro Leu His Trp Ala Lys Asn Ala Glu Met Ala Arg Met Leu Leu
290                 295                 300

Lys Arg Gly Cys Asn Val Asn Ser Thr Ser Ala Gly Asn Thr Ala
305                 310                 315                 320

Leu His Val Ala Val Met Arg Asn Arg Phe Asp Cys Ala Ile Val Leu
            325                 330                 335

Leu Thr His Gly Ala Asn Ala Asp Ala Arg Gly Glu His Gly Asn Thr
        340                 345                 350

Pro Leu His Leu Ala Met Ser Lys Asp Asn Val Glu Met Ile Lys Ala
    355                 360                 365

Leu Ile Val Phe Gly Ala Glu Val Asp Thr Pro Asn Asp Phe Gly Glu
370                 375                 380

Thr Pro Thr Phe Leu Ala Ser Lys Ile Gly Arg Gln Leu Gln Asp Leu
385                 390                 395                 400

Met His Ile Ser Arg Ala Arg Lys Pro Ala Phe Ile Leu Gly Ser Met
            405                 410                 415

Arg Asp Glu Lys Arg Thr His Asp His Leu Leu Cys Leu Asp Gly Gly
        420                 425                 430

Gly Val Lys Gly Leu Ile Ile Ile Gln Leu Leu Ile Ala Ile Glu Lys
    435                 440                 445

Ala Ser Gly Val Ala Thr Lys Asp Leu Phe Asp Trp Val Ala Gly Thr
450                 455                 460

Ser Thr Gly Gly Ile Leu Ala Leu Ala Ile Leu His Ser Lys Ser Met
465                 470                 475                 480

Ala Tyr Met Arg Gly Met Tyr Phe Arg Met Lys Asp Glu Val Phe Arg
            485                 490                 495

Gly Ser Arg Pro Tyr Glu Ser Gly Pro Leu Glu Glu Phe Leu Lys Arg
        500                 505                 510

Glu Phe Gly Glu His Thr Lys Met Thr Asp Val Arg Lys Pro Lys Val
    515                 520                 525

Met Leu Thr Gly Thr Leu Ser Asp Arg Gln Pro Ala Glu Leu His Leu
530                 535                 540

Phe Arg Asn Tyr Asp Ala Pro Glu Thr Val Arg Glu Pro Arg Phe Asn
545                 550                 555                 560

Gln Asn Val Asn Leu Arg Pro Pro Ala Gln Pro Ser Asp Gln Leu Val
            565                 570                 575

Trp Arg Ala Ala Arg Ser Ser Gly Ala Ala Pro Thr Tyr Phe Arg Pro
        580                 585                 590

Asn Gly Arg Phe Leu Asp Gly Gly Leu Leu Ala Asn Asn Pro Thr Leu
    595                 600                 605

Asp Ala Met Thr Glu Ile His Glu Tyr Asn Gln Asp Leu Ile Arg Lys
610                 615                 620

Gly Gln Ala Asn Lys Val Lys Lys Leu Ser Ile Val Val Ser Leu Gly
625                 630                 635                 640

Thr Gly Arg Ser Pro Gln Val Pro Val Thr Cys Val Asp Val Phe Arg
            645                 650                 655
```

```
Pro Ser Asn Pro Trp Glu Leu Ala Lys Thr Val Phe Gly Ala Lys Glu
            660                 665                 670

Leu Gly Lys Met Val Val Asp Cys Cys Thr Asp Pro Asp Gly Arg Ala
            675                 680                 685

Val Asp Arg Ala Arg Ala Trp Cys Glu Met Val Gly Ile Gln Tyr Phe
    690                 695                 700

Arg Leu Asn Pro Gln Leu Gly Thr Asp Ile Met Leu Asp Glu Val Ser
705                 710                 715                 720

Asp Thr Val Leu Val Asn Ala Leu Trp Glu Thr Glu Val Tyr Ile Tyr
                725                 730                 735

Glu His Arg Glu Glu Phe Gln Lys Leu Ile Gln Leu Leu Ser Pro
            740                 745                 750

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: variable amino acid

<400> SEQUENCE: 2

Gly Xaa Ser Gly Ser
  1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: variable amino acid

<400> SEQUENCE: 3

Gly Xaa Ser Thr Gly
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 4

His His His His His His
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Gly Thr Ser Thr Gly
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Val Lys Gly
  1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Asn Tyr Asp Ala Pro Glu Val Ile Arg Glu
  1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Gln Pro Ala Glu Leu His Leu Phe Arg Asn
  1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Lys Pro Ala Phe Ile Leu Ser Ser Met Arg Asp
  1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Asn Tyr Asp Ala Pro Glu Val Ile Arg Glu Pro Arg Phe
  1               5                  10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
```

-continued

```
                                peptide

<400> SEQUENCE: 11

Arg Gly Ser Arg Pro Tyr Glu Ser Gly Pro Leu Glu Glu Phe Leu Lys
 1               5                  10                  15

Arg

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Val Met Leu Thr Gly Thr Leu Ser Asp Arg Gln Pro Ala Glu Leu
 1               5                  10                  15

His Leu Phe Arg Asn
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Phe Asn Gln Asn Ile Asn Leu Lys Pro Pro Thr Gln Pro Ala Asp
 1               5                  10                  15

Gln Leu Val Trp Arg Ala
            20
```

SCREENING METHOD FOR IDENTIFICATION OF COMPOUNDS WITH CALCIUM-INDEPENDENT PHOSPHOLIPASE $A_2\beta$ ($iPLA_2\beta$) MODULATING ACTIVITY

CROSS-REFERENCE TO RELATED APPLICATIONS

This application is a continuation of U.S. patent application Ser. No. 11/539,141 filed Oct. 5, 2006 now abandoned, which claims the priority of U.S. Provisional Patent Application Ser. No. 60/723,685 filed Oct. 5, 2005, which is hereby incorporated by reference in its entirety.

STATEMENT REGARDING FEDERALLY SPONSORED RESEARCH AND DEVELOPMENT

This invention was made under contracts NIH 5P01HL57278 and NIH 5R01HL41250. The government has certain rights in the invention.

BACKGROUND OF THE INVENTION

This invention relates generally to biomarker screening and more particularly to identifying new targets for pharmacological inhibition.

This invention also relates generally to analytical (assays) methods for identifying compounds useful for promoting health in living mammalian systems. In particular this invention relates to assays and analytical tools for monitoring health in living mammals.

The function of complex living biological organisms relies on the meticulous control of cellular activity, including close regulation of cell growth, proliferation and function. The family of enzymes known as phospholipases $A_2$ has been implicated in the control of cellular activity by catalyzing the esterolytic cleavage of fatty acids from phospholipids, thereby regulating the release of lipid second messengers, cellular growth factors, and the properties of the cellular membrane (Samuelsson et al., Annu. Rev. Biochem. 47:997-1029, 1978; Moolenaar, W. H., Curr. Opin. Cell. Biol. 7:203-10, 1995). In particular, by controlling the production of second messengers such as arachidonic acid and its biologically active eicosanoid metabolites, phospholipases $A_2$ are involved in modulating such processes as cellular growth programs, inflammation, vascular tone and ion channel function. (Needleman et al., Annu. Rev. Biochem. 55:69-102, 1986).

Phospholipases $A_2$ are a broad family of enzymes with varying kinetic and physical properties, and distinct functions. Early research focused on distinguishing broad classes of the enzymes within the larger family. Several classes were distinguished using in vitro activity assays, and are categorized based on the dependence of their enzymatic activity on the presence of calcium ion. (See e.g., Demel et al, Biochim. Biopliys. Acta 406:97-107, 1975). Thus, one class, the secretory phospholipases $A_2$ are distinguished by an obligatory dependence on high (millimolar) concentrations of calcium ions, as well as low molecular weights (14-18 kDa) and relative heat stability. (Demel et al., supra; Tischfield, J. A., J. Biol. Chem. 272:17247-50, 1997). The activity of a second class, the cytosolic phospholipases $A_2$ is facilitated by the presence of nanomolar concentrations of calcium ions, but the presence of the calcium ion is not obligatory. (Loeb et al., J. Biol. Chem. 261:10467-70, 1986; Kramer et al., Biochim. Biophys. Acta 878:394-403; Glover et al., J. Biol. Chem. 270:15359-67, 1986). A third class of enzymes is entirely calcium-independent in in vitro studies, and is also distinguished by a finely tuned inhibition by (E)-6-(bromomethylene)-3-(1-napthalenyl)-2H-tetrahydropyran-2-one (BEL). (Wolf et al., J. Biol. Chem. 260:7295-303; Hirashima et al., J. Neurochem. 59:708-14; Lehman et al., J. Biol. Chem. 268: 20713-16).

Application of molecular biological techniques has provided some insights into the structure and function of founding members in each class of phospholipases $A_2$ and has provided a further basis for distinguishing among the classes. (See, e.g. Demel et al., supra; Evenberg et al., J. Biol. Chem. 252: 1189-96, 1977; Tischfield, J. A., J. Biol. Chem. 272: 17247-50, 1997). For example, members of the secretory phospholipases $A_2$ use a calcium ion to polarize the carbonyl for attack by a histidine-activated $H_2O$ molecule, while the intracellular phospholipases use a nucleophilic serine. The calcium-facilitated phospholipases $A_2$ have a GXSGS (SEQ ID NO: 2) consensus lipase motif, in contrast to the $iPLA_2$ group which has a GXSTG (SEQ ID NO: 3) consensus motif. The calcium-independent phospholipases $A_2$ are also distinguished by a consensus sequence for nucleotide binding. (Andrews et al., Biochem. J. 252:199-206, 1988; Tang et al., J. Biol. Chem. 272:8567-75, 1998). These findings have clearly boosted progress toward identifying the polypeptides responsible for catalyzing the synthesis of the eicosanoid metabolites and toward understanding the regulatory mechanisms of phospholipases $A_2$ that are involved in normal and disease states.

The more recent developments of intense genome sequencing efforts have produced partial sequence data on the phospholipases and have led to related structural insights. For example, two new calcium-facilitated phospholipases have recently been described based on data from protein and nucleotide databases. (Underwood et al., J. Biol. Chem. 273: 21926-32, 1998; Pickard et al., J. Biol. Chem. 274: 8823-31, 1999). Further, during sequencing of the long arm of chromosome 7 in the Human Genome Sequencing Project, a predicted protein product of 40 kDa was identified. The polypeptide contained two 10 amino acid segments homologous to the lipase and nucleotide-binding consensus sequences described for the founding members of the $iPLA_2$ family. (Tang et al., supra).

Earlier work has been done with respect to phospholipases and certain disease conditions in animals. For example, intensive study of reperfusion injury in myocardial tissue has led to the hypothesis that pathology is ultimately generated because of membrane phospholipid breakdown attributable to activation of myocardial phospholipase $A_2$ activity. (See e.g. Van der Vusse et al., Hydrolysis of phospholipids and cellular integrity, In: H. M. Piper (ed.) Pathophysiology of Severe Ischemic Myocardial injury, Kluwer Academic Publishers, Dordrecht, The Netherlands, 1990, 167-93). Furthermore, calcium-dependent and calcium-independent phospholipase $A_2$ activities have also been found to be present in the human cerebral cortex. Some reports have suggested a possible link between the activity of both calcium-dependent calcium independent phospholipases $A_2$ and cortical degenerative diseases such as Alzheimer's disease. (For reviews, see e.g. Farooqui et al., Neurochem. Int. 30: 5 17-22, 1997; Farooqui et al., Brain Res. Bull. 49: 139-53, 1999).

Certain inhibitors of phospholipases $A_2$ have been identified as possible therapeutic candidates for treating $PLA_2$-mediated diseases. For example, fatty acid trifluoromethyl ketones, bromoenol lactone, methyl arachidonyl fluorophosphonate, benzenesulfonamides and other specific inhibitors of phospholipases $A_2$ have been shown to decrease $PLA_2$ activity and all have been considered for treating inflammatory diseases thought to be mediated by $PLA_2$. (See e.g. Farooqui et al, 1999, supra). Nevertheless, as noted above, the phospholipases $A_2$, as well as the $iPLA_2$ subfamily itself, are a heterogeneous group of enzymes, with differing molecular weights, substrates, and responses to inhibitors. Because of this, the development of agents for treating diseases mediated by these compounds is ideally based upon determining and characterizing the structure and functional characteristics of the particular $iPLA_2$ involved in the disease process. Thus, it is important to identify and characterize the phospholipases $A_2$ family members.

During the last decade, excessive consumption of fat in high caloric Western diets in conjunction with a sedentary life style, has resulted in an epidemic of obesity in industrialized nations (1, 2). Obesity is associated with insulin resistance, hypertension, dyslipidemia, type 2 diabetes and atherosclerosis, which collectively constitute the metabolic syndrome (3, 4, 5). Despite the enormous proportions of this public health problem, the biochemical mechanisms underlying the metabolic syndrome and its end-organ sequelae are poorly understood.

With respect to diabetes, glucose utilization is necessary for the body to be able to use sugar which is stored in the blood as glucose. Insulin initiates the process of taking glucose from the blood and moving it into the cells. However, when glucose builds up in the blood instead of going into cells (e.g., insulin resistance), it can cause serious life threatening problems which results in type 2 diabetes. These include heart disease (cardiovascular disease), blindness (retinopathy), nerve damage (neuropathy), and kidney damage (nephropathy).

Type 2 diabetes is the most common form of diabetes. In this condition the body does not produce enough insulin to cause cells to transport glucose or the cells are not sensitive enough to the insulin present. The concentration of blood glucose becomes and remains high in the blood resulting in unnecessary and undesired damage to the body. Thus glucose is not utilized, proteins are covalently modified, inappropriate oxidation occurs and a change to fatty acid substrate occurs.

DETAILED DESCRIPTION OF THE DRAWINGS

Figure 1A:
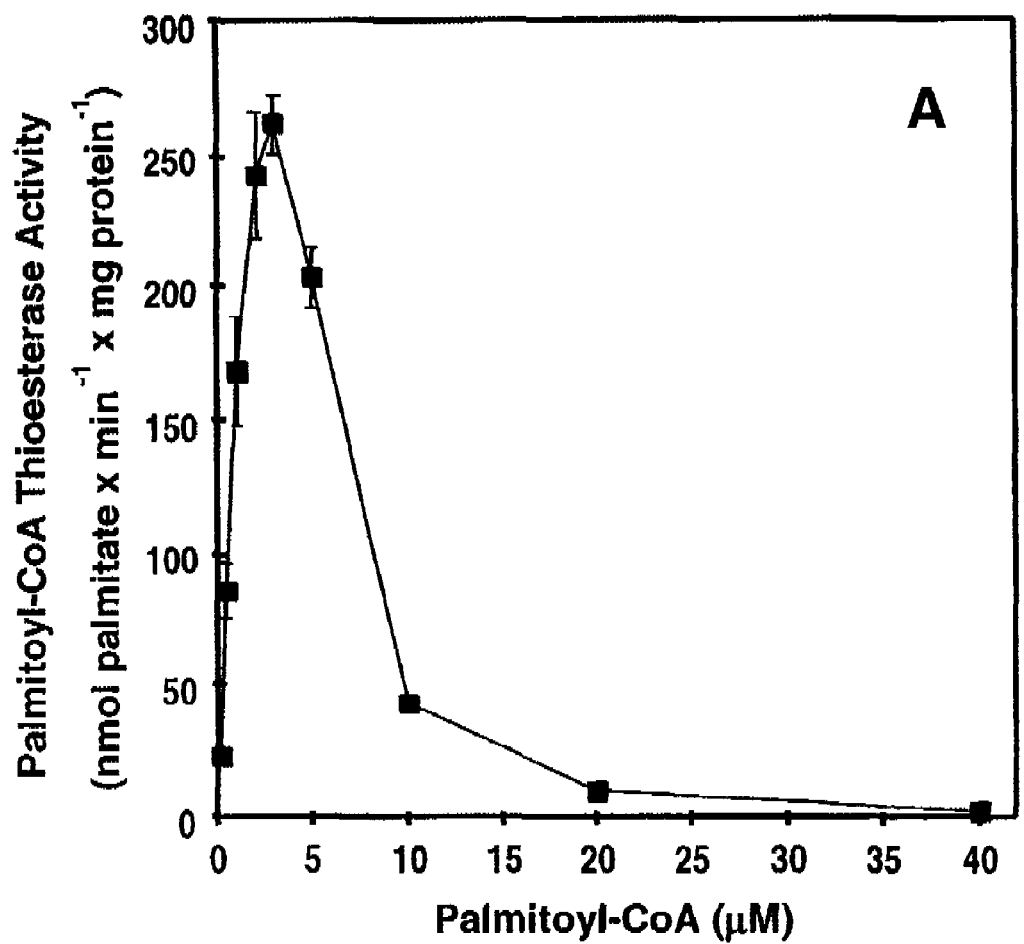
FIGS. 1A and 1B depict palmitoyl-CoA Thioesterase Activity of $iPLA_2\beta$. 1A depicts Substrate inhibition of $iPLA_2\beta$ palm-CoA hydrolase activity. 1B depicts $iPLA_2\beta$ catalyzed hydrolysis of palmitoyl-CoA guest in host POPC/DOPS vesicles.
Figure 1B:
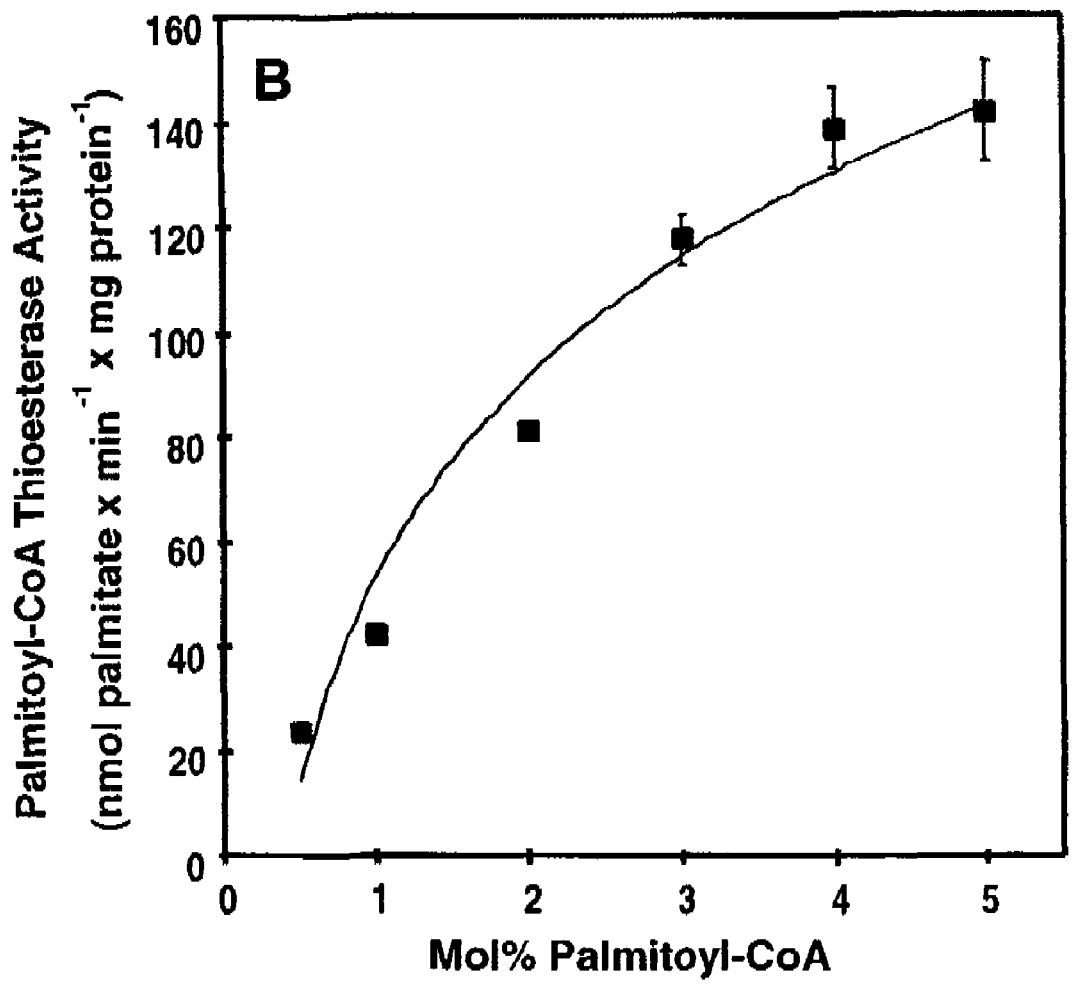

FIGS. 1A and 1B—Purified $iPLA_2\beta$ $(His)_6$ (peptide disclosed as SEQ ID NO: 4) was incubated with the indicated concentrations of $[1-^{14}C]$-palmitoyl-CoA for 1-2 min at 37° C. Reactions were terminated by vortexing with butanol and $[1-^{14}C]$-palmitic acid extracted into the butanol layer was resolved by TLC and quantified by liquid scintillation spectrometry as described in Experimental Procedures. B, $iPLA_2\beta$ catalyzed hydrolysis of palmitoyl-CoA guest in host POPC/DOPS vesicles. The indicated mol % of $[^{14}C]$-palmitoyl-CoA were incorporated into POPC/DOPS (90:10) vesicles (100 μM final vesicle lipid concentration). Each data point represents the average±S.E. for at least 4 separate determinations.

Figure 2:
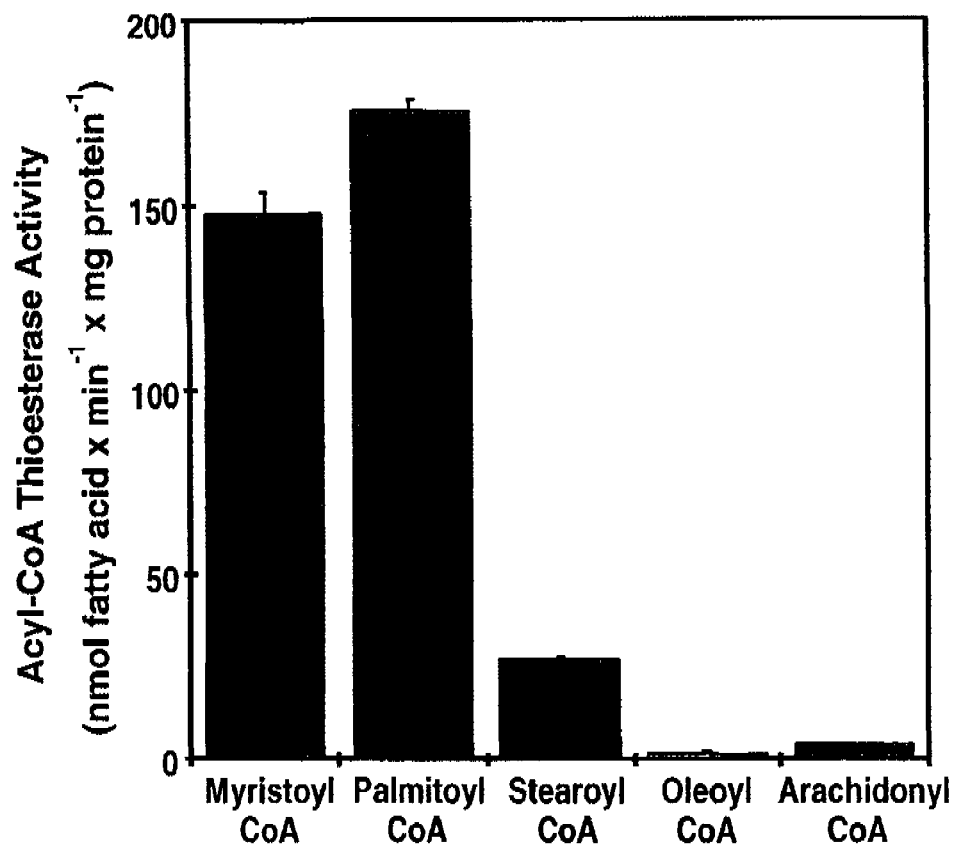
FIG. 2 depicts substrate Selectivity of $iPLA_2\beta$ Long-chain Acyl-CoA Hydrolase Activity in the Presence of POPC/DOPS Vesicles.

FIG. 2—Purified $iPLA_2\beta$ $(His)_6$ (peptide disclosed as SEQ ID NO: 4) was incubated with equal amounts of the indicated $[1-^{14}C]$-acyl-CoA guest (5 mol %) in POPC/DOPS (90:10) host vesicles for 2 min at 37° C. Released $[1-^{14}C]$-fatty acid was extracted into butanol by vortexing, resolved by TLC, and quantified by liquid scintillation spectrometry as described in Experimental Procedures. Each data point represents the average ±SE. from 8 separate determinations.

Figure 3:
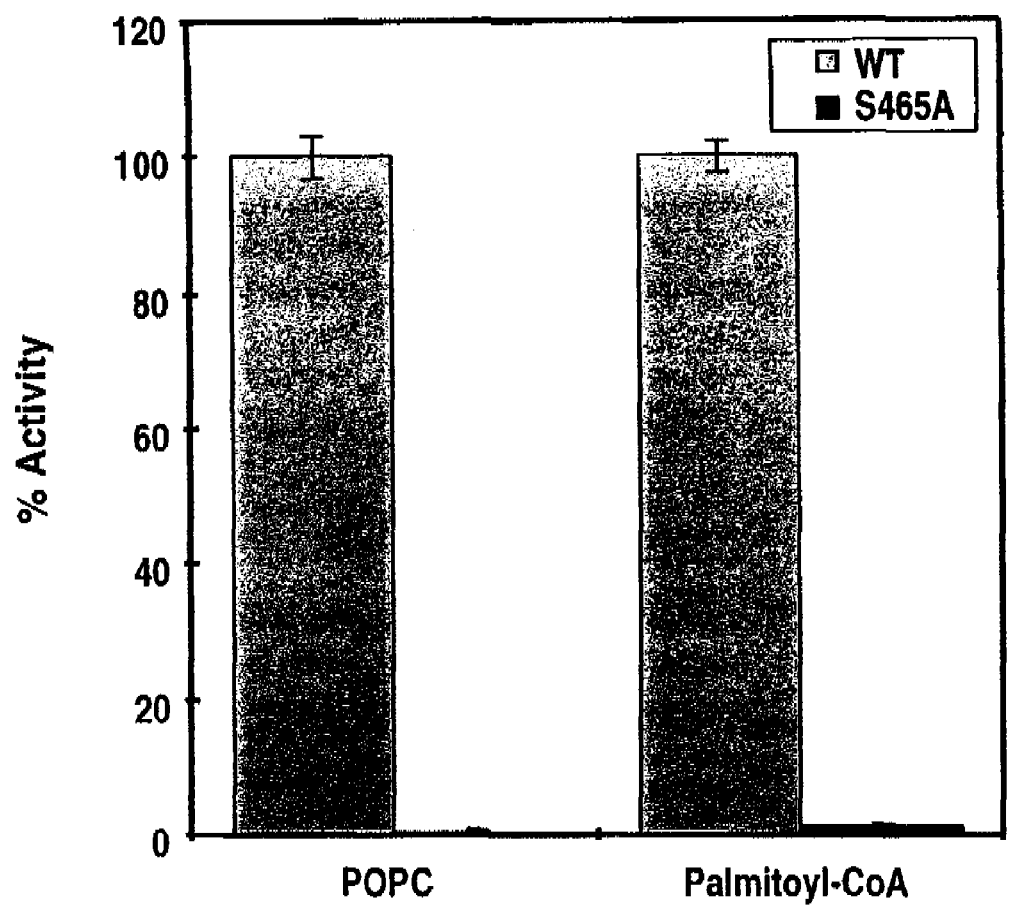
FIG. 3 depicts mutagenesis of Ser-465 to Alanine Eliminates $iPLA_2\beta$ Phospholipase $A_2$ and Palmitoyl-CoA Hydrolase Activities.

FIG. 3—Equivalent amounts of purified $iPLA_2\beta$ $(His)_6$ (peptide disclosed as SEQ ID NO: 4) (WT) or mutant $iPLA_2\beta$ $(His)_6$ (peptide disclosed as SEQ ID NO: 4) (S465A) were incubated with either 1-palmitoyl-2-$[1-^{14}C]$-oleoyl-sn-glycero-3-phosphocholine (5 μM) or $[1-^{14}C]$-palmitoyl-CoA (5 μM) for 2 min at 37° C. Radiolabeled fatty acids from the reaction were extracted into butanol, resolved by TLC, and quantified by liquid scintillation spectrometry as described in Experimental Procedures. Results are representative of the average ±S.E. of 4 separate determinations.

Figure 4:
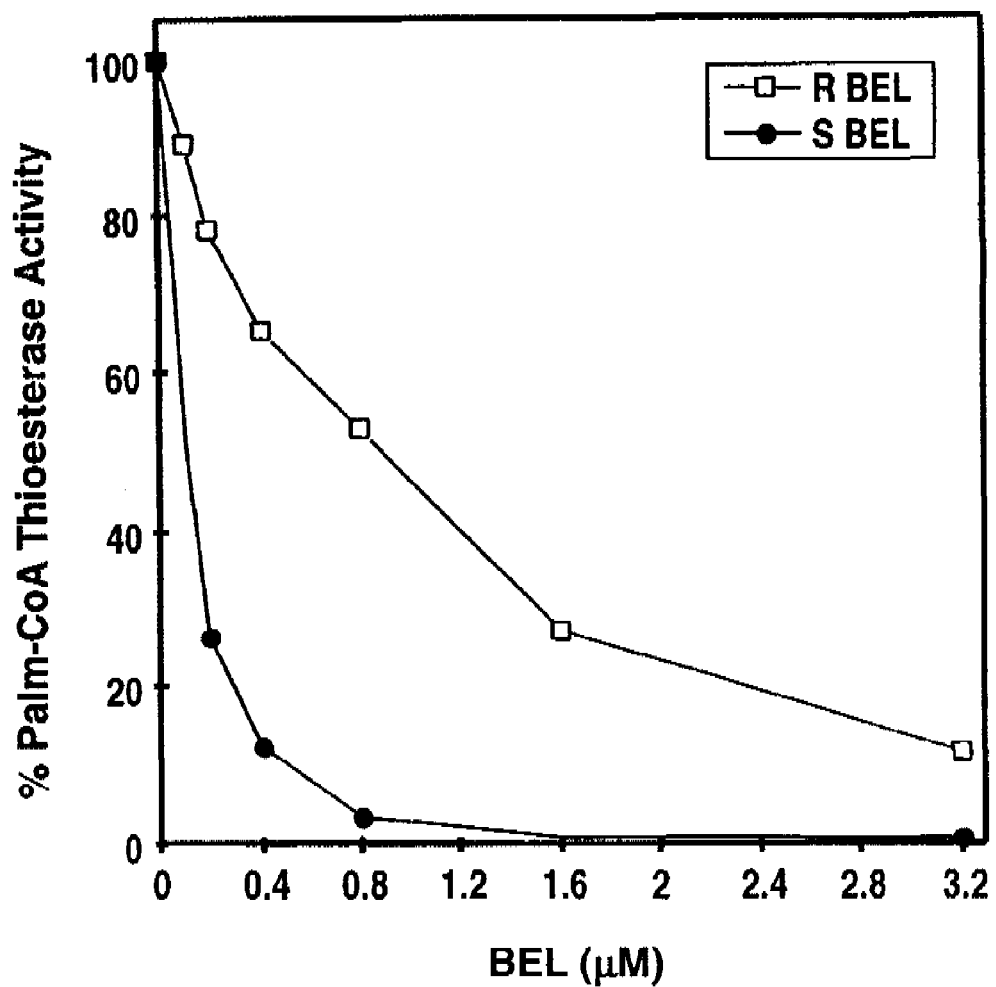
FIG. 4 depicts inhibition of $iPLA_2\beta$ Palmitoyl-CoA Thioesterase Activity by (R)- and (S)-BEL.

FIG. 4—Purified $iPLA_2\beta$ $(His)_6$ (peptide disclosed as SEQ ID NO: 4) was preincubated with the indicated concentrations of either enantiomer of BEL or ethanol vehicle for 3 min at 23° C. The enzyme was then added to 100 mM Tris-HCl, pH 7.2 containing 1 mM EGTA and $[1-^{14}C]$-palmitoyl-CoA guest (5 mol %) in POPC (100 μM) host vesicles for 2 min at 37° C. Following extraction into butanol, liberated $[1-^{14}C]$-palmitic acid was separated from $[1-^{14}C]$-palmitoyl-CoA by TLC and quantified by liquid scintillation spectrometry as described in Experimental Procedures.

Figure 5:
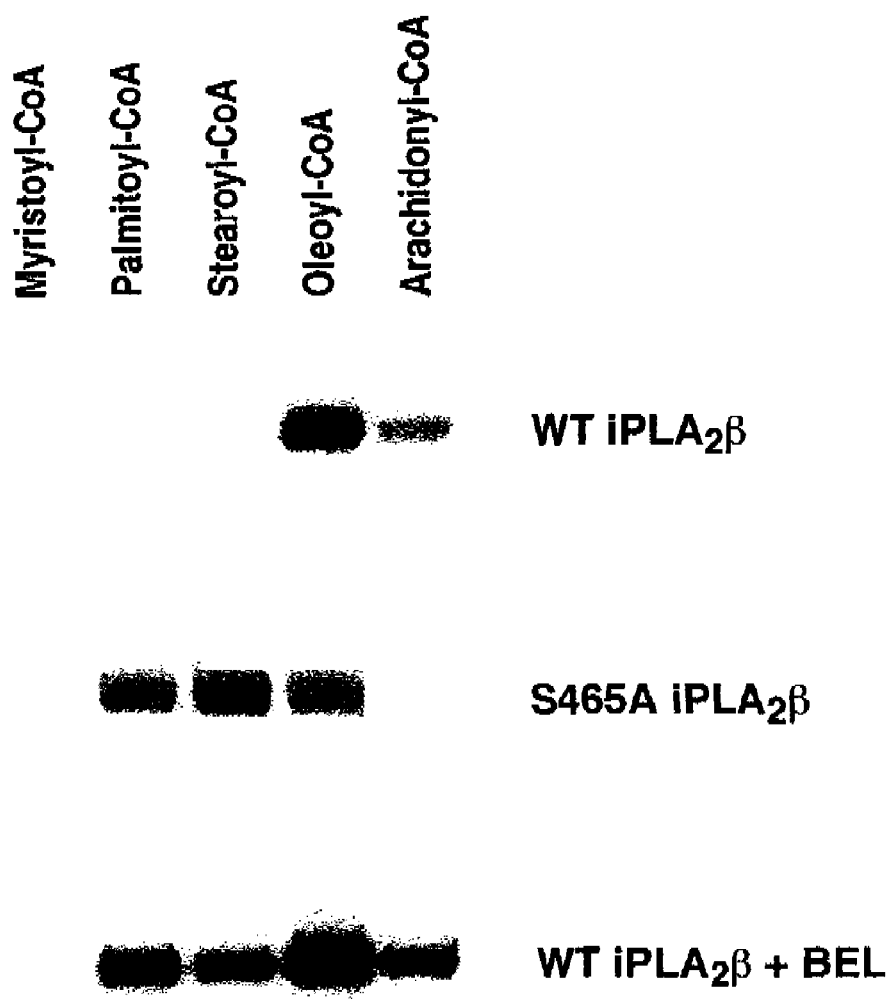
FIG. 5 depicts selective acylation of $iPLA_2\beta$ Wild-type, S465A Mutant, and BEL pretreated Wild-type Proteins with Various Long-chain Acyl-CoAs.

FIG. 5—Equivalent amounts of the indicated $[1-^{14}C]$-acyl-CoA guests (5 mol %) were incorporated into host POPC (100 μM) vesicles and incubated for 1 hr at 37° C. with equal amounts of either wild-type (WT) $iPLA_2\beta(His)_6$ (peptide disclosed as SEQ ID NO: 4), S465A $iPLA_2\beta(His)_6$ (peptide disclosed as SEQ ID NO: 4), or BEL-pretreated WT $iPLA_2\beta$ $(His)_6$ (peptide disclosed as SEQ ID NO: 4) enzyme as described in Experimental Procedures. Samples were resolved by SDS-PAGE (10% gel), fixed, and dried before visualization by autoradiography.

Figure 6:
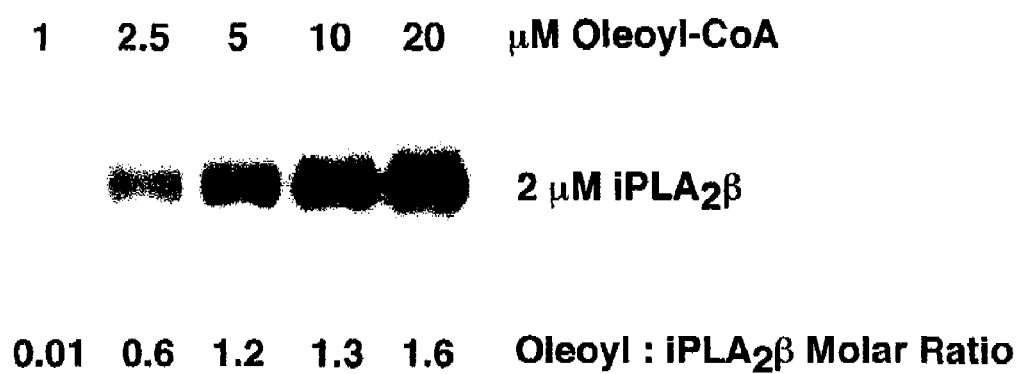
FIG. 6 depicts stoichiometry of $iPLA_2\beta$ Acylation by Oleoyl-CoA.

FIG. 6—Purified $iPLA_2\beta(His)_6$ (peptide disclosed as SEQ ID NO: 4) (2 μM) was incubated with the indicated concentrations of $[1-^{14}C]$-oleoyl-CoA present as guest in host POPC (100 μM) vesicles for 1 hr at 37° C. Samples were electrophoresed in parallel with standard amounts (0.5-10 nCi) of $[^{14}C]$-BSA of known activity (not shown). The fixed and dried gel was exposed to film and the resultant signals from the $[^{14}C]$-BSA were utilized to generate a standard curve utilizing ID software from a Kodak Imagestation to determine the incorporation of $[1-^{14}C]$-oleate into $iPLA_2\beta$.

Figure 7:
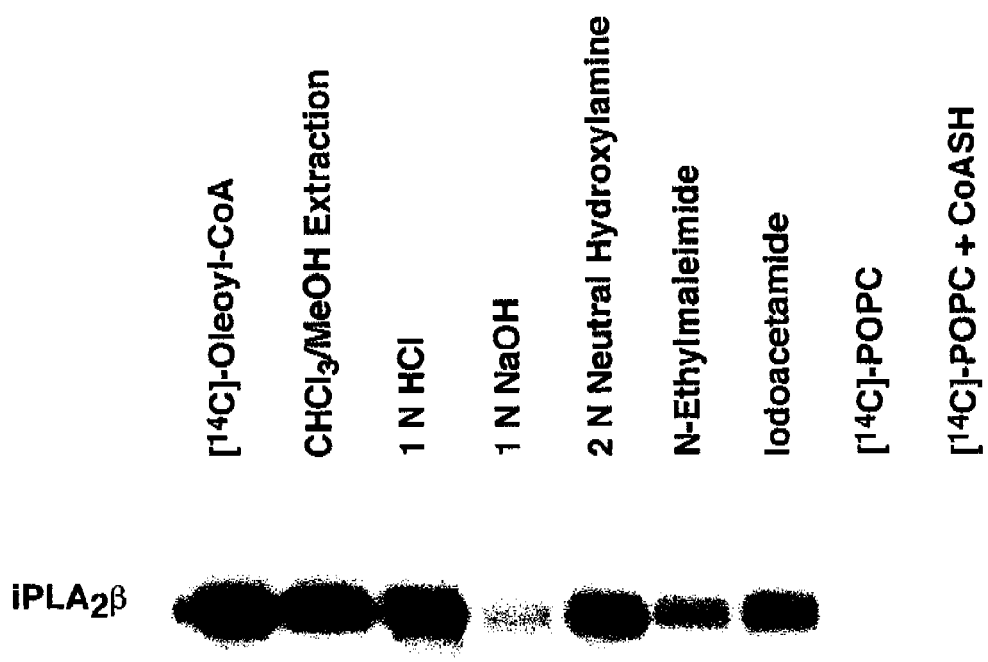
FIG. 7 depicts effect of Various Chemical Treatments on $iPLA_2\beta$ Autoacylation with $[1-^{14}C]$-Oleoyl-CoA.

FIG. 7—Purified iPLA$_2\beta$(His)$_6$ (peptide disclosed as SEQ ID NO: 4) was incubated with [1-$^{14}$C]-oleoyl CoA (10 mol %) incorporated as guest in host POPC vesicles. N-ethylmaleimide and iodoacetamide samples were pretreated with 5 mM of either reagent for 5 min at 30° C. before addition of [1-$^{14}$C]-oleoyl-CoA. Samples were incubated with 1 N HCl, 1 N NaOH, or 2 N neutral hydroxylamine for 1 hr at 30° C. as indicated. All samples, except lane 1, were precipitated with CHCl$_3$/MeOH and washed with 70% acetone before SDS-PAGE and autoradiography as described in Experimental Procedures.

Figure 8:
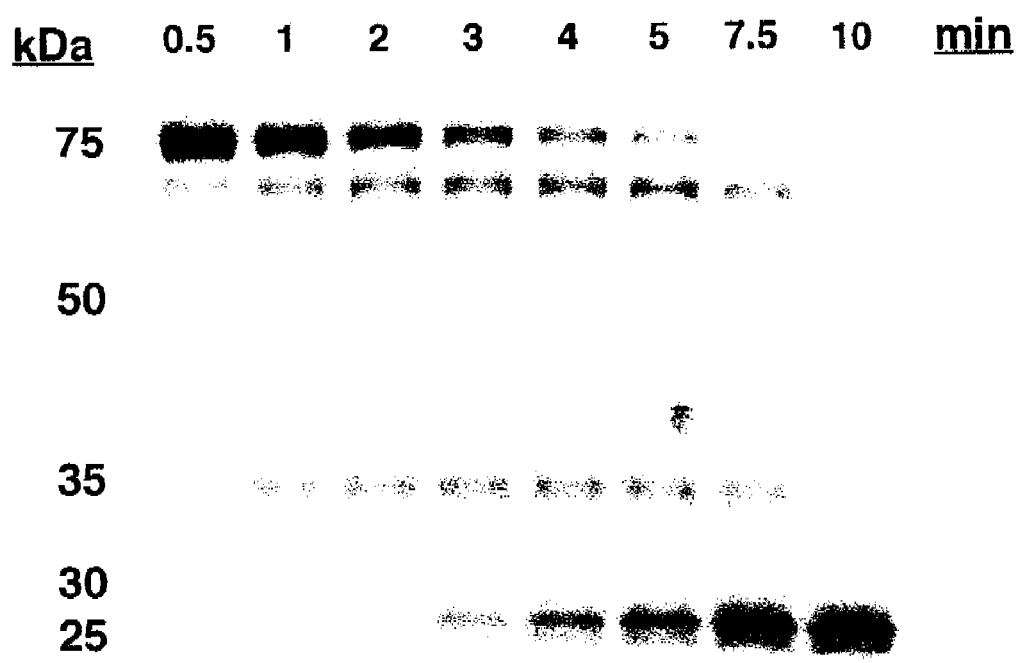
FIG. 8 depicts partial trypsinolysis of $[1-^{14}C]$-Oleoyl-$iPLA_2\beta$.

FIG. 8—[1-$^{14}$C]-oleoyl-iPLA$_2\beta$(His)$_6$ (peptide disclosed as SEQ ID NO: 4) was prepared by incubation of the unmodified enzyme (10 μM) with 50 μM [1-$^{14}$C]-oleoyl-CoA for 1 hr at 37° C. Trypsin (1:25 w/w) was added and incubated with [1-$^{14}$C]-oleoyl-iPLA$_2\beta$(His)$_6$ (peptide disclosed as SEQ ID NO: 4) for the indicated times. Following termination of proteolysis by addition of loading buffer, tryptic peptides were resolved by SDS-PAGE and radiolabeled fragments were visualized by autoradiography as described in Experimental Procedures.

Figure 9:
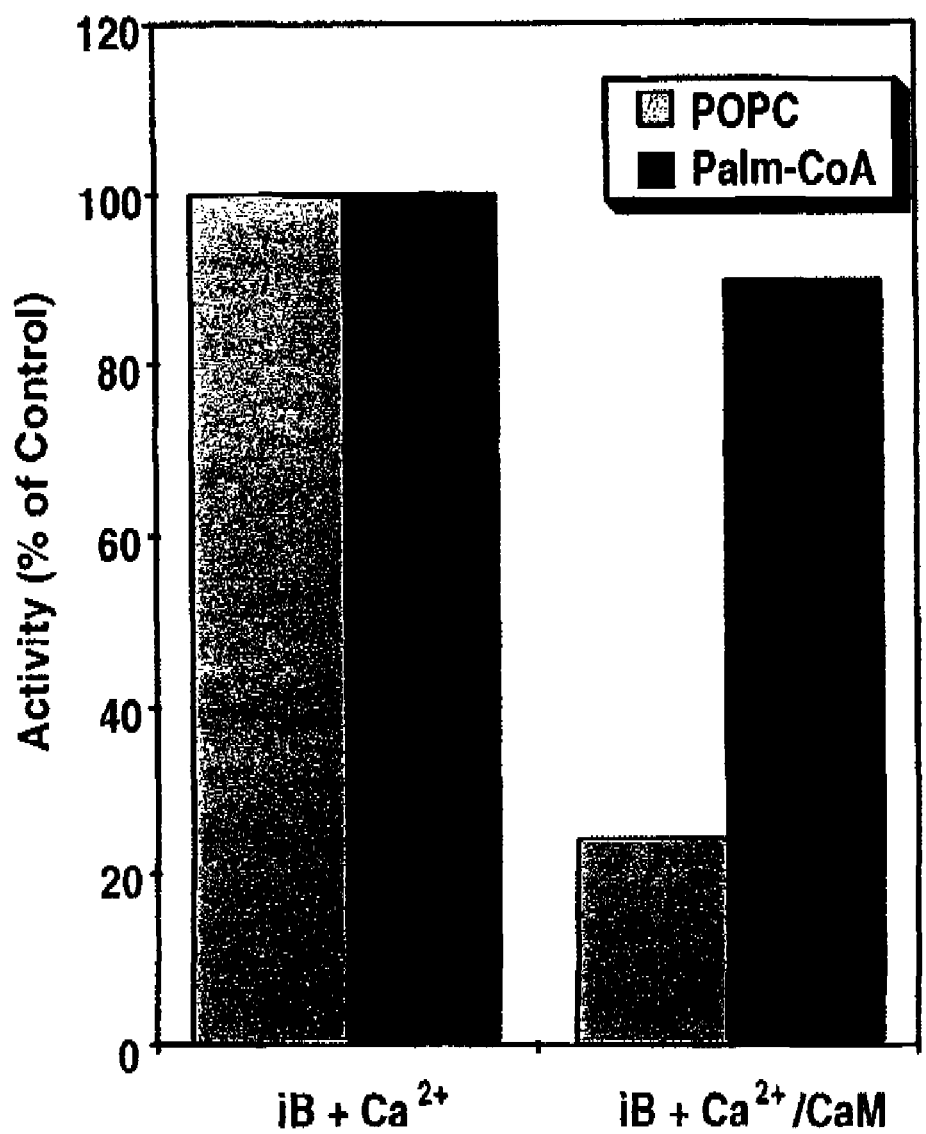
FIG. 9 depicts $Ca^{2+}$-CaM Does Not Inhibit the Palmitoyl-CoA Thioesterase Activity of $iPLA_2\beta$.

FIG. 9—Calcium-independent iPLA$_2\beta$ was pre-incubated in the presence of Ca$^{2+}$ (1 mM) or Ca$^{2+}$-CaM (3 μg) on ice before addition to 95 μM POPC containing either 5 mol % [1-$^{14}$C]-POPC or [1-$^{14}$C]-palmitoyl-CoA in 100 mM Tris-HCl, pH 7.2. After incubation at 37° C. for 3 min, reactions were terminated by vortexing in the presence of butanol and released radiolabeled fatty acids were resolved by TLC and quantitated by liquid scintillation spectrometry as described in Experimental Procedures.

Figure 10:
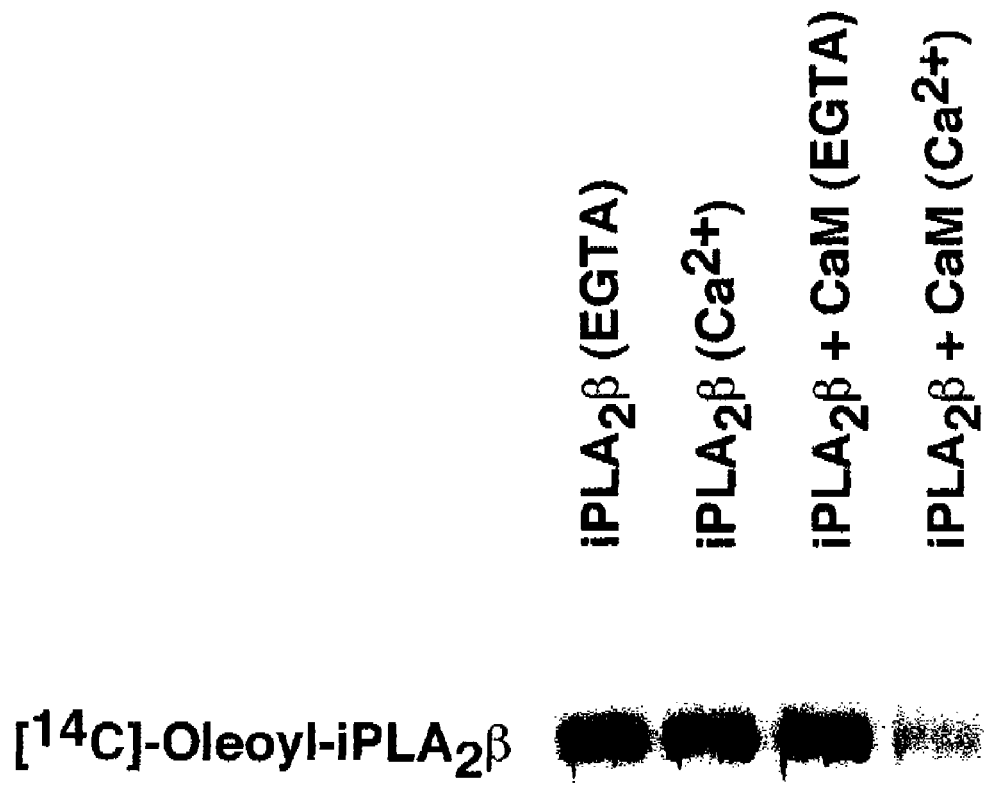
FIG. 10 depicts $Ca^{2+}$-CaM Inhibits Covalent Acylation of $iPLA_2\beta$ by Oleoyl-CoA.

FIG. 10—Purified iPLA$_2\beta$(His)$_6$ (peptide disclosed as SEQ ID NO: 4) was incubated with [1-$^{14}$C]-oleoyl CoA (10 mol %) incorporated as guest in host POPC vesicles in the presence of EGTA (5 mM), Ca$^{2+}$ (1 mM), CaM (3 μg), or Ca$^{2+}$-CaM for 1 h at 37° C. Samples were resolved by SDS-PAGE and the gel was soaked in Amplify fluorographic reagent, dried, and exposed to film as described in Experimental Procedures.

FIGS. 11A-11D—Purified iPLA$_2\beta$+/−Ca$^{2+}$/CaM was incubated with POPC/BODIPY-PC (95:5 mol %) host vesicles for 2 min at 37° C. with the indicated concentrations of guest oleoyl-CoA. Relative fluorescence was recorded utilizing 495 nm excitation and 515 nm emission wavelengths as described in Experimental Procedures. FIGS. 11E-11H—ESI-MS analysis of phosphatidylcholine molecular species from the reactions described in panels A and D. Spectra were acquired in the positive ion mode with the indicated internal standards as described in Experimental Procedures. FIG. 11I—Purified iPLA$_2\beta$ in the presence or absence of Ca$^{2+}$/CaM was incubated with 1-palmitoyl-2-[1-$^{14}$C]-oleoyl-sn-glycero-3-phosphocholine (100 μM) host vesicles with or without guest oleoyl-CoA (10 μM) for 3 min at 37° C. Radiolabeled fatty acid was extracted into butanol, resolved by TLC, and quantified by scintillation spectrometry as described in Experimental Procedures.

BRIEF DESCRIPTION OF THE INVENTION

A method for treating a mammal, said method comprising administering a gene, enzyme or pharmaceutical which modulates the concentration of iPLA$_2\beta$ through transcriptional and/or translational regulation or effectively modulates the inhibition of iPLA$_2\beta$ through calmodulin or derivatives thereof.

A method of regulating cellular processes dependent upon Ca$^{2+}$ influx or entry related to the activation or inhibition of iPLA$_2\beta$, the method comprising at least one of the steps of reversing the interaction of iPLA$_2\beta$ with calcium-activated calmodulin, and enhancing the interaction of iPLA$_2\beta$ with Calcium-activated calmodulin.

A method of activation of iPLA$_2\beta$ during ischemia comprises promoting re-formation of the iPLA$_2\beta$:CaM complex in a subject, and decreasing phospholipid hydrolysis and associated ischemic damage.

DETAILED DESCRIPTION OF THE INVENTION

Without being bound by theory, the discovery comprises an isolated and characterized oleoyl-iPLA$_2\beta$ having Sequence NO. 1. In an aspect the oleoyl-iPLA$_2\beta$ comprises that of a living human. In an aspect the oleoyl-iPLA$_2\beta$ comprises that of a living mouse.

Unless otherwise defined, technical and scientific terms used herein have the same meaning as commonly understood by one of ordinary skill in the art. Methods and materials similar or equivalent to those described herein can be used in the practice or testing of the present discovery.

As used herein, the term "peptide" includes any of a group of compounds comprising two or more amino acids linked by chemical bonding between their respective carboxyl and amino groups. The term "peptide" includes peptides and proteins that are of sufficient length and composition to effect a biological response, e.g. antibody production or cytokine activity whether or not the peptide is a hapten. The term "peptide" includes modified amino acids, such modifications including, but not limited to, phosphorylation, glycosylation, prenylation, lipidization and methylation.

As used herein, the term "polypeptide" includes any of a group of natural or synthetic polymers made up of amino acids chemically linked together such as peptides linked together. The term "polypeptide" includes peptide, translated nucleic acid and fragments thereof.

As used herein, the term gene includes "polynucleotide" which includes nucleotide sequences and partial sequences, DNA, cDNA, RNA variant isoforms, splice variants, allelic variants and fragments thereof.

As used herein, the terms "protein", "polypeptide" and "peptide" are used interchangeably herein when referring to a translated nucleic acid (e.g. a gene product). The term "polypeptide" includes proteins. The term "protein" includes any large molecule composed of one or more chains of amino acids in a specific order; the order is determined by the base sequence of nucleotides in the gene that codes for the protein. The term "protein" includes a fragment and functional fragments of proteins.

As used herein, the term "nucleic acid" refers to oligonucleotides or polynucleotides such as deoxyribonucleic acid (DNA) and ribonucleic acid (RNA) as well as analogs of either RNA or DNA, for example made from nucleotide analogs any of which are in single or double stranded form.

As used herein, the term "therapeutic agent" is any molecule or atom which is conjugated, fused or otherwise affixed to an antibody moiety to produce a conjugate which is useful for therapy.

As used herein, the term "biological sample" includes vascular tissue or blood, urine or other body fluids.

As used herein, the term "antisense" means a strand of RNA whose sequence of bases is complementary to messenger RNA.

As used herein the term "oligo" includes oligonucleotides which are polymers of nucleosides joined, generally, through phosphoester linkages.

As used herein a "therapeutic amount" is an amount of a moiety which produces a desired or detectable therapeutic effect on or in a mammal administered the moeity.

As used herein, the term "sample" means a viable (analyzable) sample of biological tissue or fluid. A biological sample includes an effective amount of a representative section of tissues or fluids of living animals, viable cells or cell culture.

In an aspect, the DNA or genetic construct further comprises an expression control sequence operably linked to a sequence encoding (and expressing) the expression product.

As used herein, the terms "DNA construct" or "genetic gene construct", "gene" or "cDNA" are used interchangeably herein to refer to a nucleic acid molecule which may be one or more of the following: regulatory regions, e.g. promoter and enhancer sequences (that are competent to initiate and otherwise regulate the expression of a gene product(s)); any other mutually desired compatible DNA elements for controlling the expression and/or stability of the associated gene product(s) such as polyadenylation sequences; other DNA sequences which function to promote integration of operably linked DNA sequences into the genome of the host cell and any associated DNA elements contained in any nucleic acid system (e.g. plasmid expression vectors) used for the propagation, selection, manipulation and/or transfer of recombinant nucleic acid sequences, sequences encoding proteins that are part of the biosensor or proteins that are functional G protein coupled receptors.

As used herein, the terms "regulatory DNA sequences" or "regulatory regions" or "DNA sequences which regulate the expression of" are used interchangeably herein to refer to nucleic acid molecules which function as promoters, enhancers, insulators, silencers and/or other similarly defined sequences which control the spatial and temporal expression of operably linked and/or associated gene products.

As used herein, the term "transgenic" refers to an organism, or progeny derived from such organism(s) by germ cell transmission or cloning, that contains exogenous genetic constructs that have been purposefully introduced into the organism. Moreover, this refers to organisms which may or may not have the introduced genetic construct stably integrated into their genome, that is, constructs which are maintained stably and can be propagated through germ cell transmission (i.e. sexual reproduction) or constructs which are expressed transiently by the organism.

As used herein the term "expression library" includes a library of chemical moieties generally whose functions are unknown. "Expression library" also includes a database, collection or assemblage of moieties or a system of containing capably identified moieties, cataloged or uncataloged, present or not present in the collection or assemblage and illustratively includes expression products of cDNA such as proteins, and enzymes including those wherein one or more of identity and function or known or are unknown.

As used herein, the term "expression" includes the biosynthesis of a product as an expression product from a gene such as the transcription of a structural gene into mRNA and the translation of mRNA into at least one peptide or at least one polypeptide. The term "expression" includes gene products such as proteins and functional fragments thereof.

As used herein, the term "mammal" includes living animals including humans and non-human animals such as murine, porcine, canine and feline.

As used herein, the term "isolated polypeptide" includes a polypeptide essentially and substantially free from contaminating cellular components.

As used herein, the term "isolated protein" includes a protein that is essentially free from contamination cellular components normally associated with the protein in nature.

As used herein, the term "patient" and subject" are synonymous and are used interchangeably herein.

We have identified the modulation (inhibition) of calcium independent phospholipase $A_2$ activity by calcium-activated calmodulin. We have demonstrated that activation of iPLA$_2\beta$ activity in intact cells results from the disinhibition of iPLA$_2\beta$ during calcium pool depletion either by agonist stimulation (leading to IP$_3$ mediated internal store calcium release) or by direct depletion of internal stores by inhibition of the Sarcoplasmic Endoplasmic Reticulum $Ca^{2+}$-ATPase (SERCA) by thapsigargin (46). Recently, this hypothesis has been reformulated to include the activation of the calcium channels by lysophospholipids through the activation of iPLA$_2\beta$ mediated by CIF-induced dissociation of the iPLA$_2\beta$-calmodulin complex. Thus, capacitative calcium entry is mediated by the activation of iPLA$_2\beta$ accomplished through the dissociation of the inhibitory calmodulin-iPLA$_2$ complex. The resultant lysolipids produced by iPLA$_2$, and perhaps other mediators as well (e.g., eicosanoids), serve to open plasma membrane calcium channels to accomplish capacitative calcium influx. This cellular signaling pathway is known to occur in a wide variety of cell specific contexts. However, the chemical identity of CIF is unknown. Similarly, the molecular types and classes of molecules that serve to disinhibit the calmodulin-iPLA$_2$ complex have not been directly identified or demonstrated. In this work, we demonstrate that the class of acyl-CoAs can serve to activate iPLA$_2\beta$ by release of calmodulin mediated inhibition. Since fatty acids are produced by depletion of internal calcium stores by either agonist stimulation or indirectly through SERCA inhibition and intracellular fatty acids are rapidly converted to acyl-CoAs these results: 1) identify acyl-CoAs as the factor that activates iPLA$_2\beta$ by relief of calmodulin mediated inhibition; 2) identify the sequential production of CIF first through calcium depletion fatty acid release and subsequent thioesterificaton; and 3) provide a molecular basis for pharmacotherapy to modulate the signals generated through capacitative calcium influx pathways for salutary interventions in a wide variety of disease states. Such diseases include, but are not limited to, inflammation, hypertension, diabetes and insulin release, congestive heart failure, atherosclerosis, myocardial infarction, arrhythmias, cancer, stroke and disorders of calcium mediated motility in general (e.g., GI, urinary, conception, birth control) or calcium influenced processes (e.g., erectile dysfunction, wrinkles and hair loss).

During cellular stimulation, multiple cell types activate calcium influx pathways in the plasma membrane facilitating the influx of extracellular calcium through non-voltage dependent calcium channels. This influx of extracellular calcium is induced by agonist-receptor interaction, activation of phospholipase C and the subsequent release of IP$_3$. The released IP$_3$ diffuses to its receptor in internal calcium stores in the endoplasmic reticulum and results in the release of calcium from the IP$_3$ gated calcium channels. Next, a second messenger of unknown chemical identity is released from these internal stores after calcium pool depletion. This second messenger diffuses to the plasma membrane to activate calcium channels in a process known as capacitative calcium influx. This calcium influx factor (CIF) has shown to be a critical component for cellular signaling in multiple cell specific contexts. However, the chemical identity of CIF is unknown. Moreover, the influx of extracellular calcium is critical both for signaling functions as well as for the repletion of internal calcium stores.

Inclusion of fatty acyl-CoA guest in phosphatidyl-choline host vesicles was demonstrated to disrupt or reverse $Ca^{2+}$-activated calmodulin inhibition of $iPLA_2\beta$ phospholipase $A_2$ activity resulting in activation of the enzyme $iPLA_2\beta$. Shotgun lipidomics identification of cardiolipin decrease in diabetic hearts. Calcium-independent phospholipase $A_2\beta$ and $iPLA_2\gamma$ were demonstrated to catalyze hydrolysis of cardiolipin as guest in phosphatidylcholine vesicles.

This invention could be used in the development of pharmaceuticals which would target the activation of $iPLA_2\beta$ and $iPLA_2\gamma$ during ischemia, diabetes, heart disease, atherosclerosis, and obesity. Biomarkers for diabetes include cardiolipin Inhibition of $iPLA_2\beta$ and $iPLA_2\gamma$ would be predicted to decrease cardiolipin degradation and improve mitochondrial function.

Calcium-independent phospholipase $A_2\beta$ ($iPLA_2\beta$) participates in numerous diverse cellular processes such as arachidonic acid release, insulin secretion, calcium signaling, and apoptosis. Herein, we demonstrate the highly selective $iPLA_2\beta$-catalyzed hydrolysis of saturated long chain fatty acyl-CoAs (rank order: palmitoyl-CoA≈myristoyl-CoA>>stearoyl-CoA>>oleoyl-CoA≈arachidonyl-CoA) present either as monomers in solution or guests in a host bilayer membrane. Site-directed mutagenesis of the catalytic serine (S465A) of $iPLA_2\beta$ completely abolished acyl-CoA thioesterase activity, demonstrating that the same active site serine residue catalyzes both phospholipid and acyl-CoA hydrolysis. Remarkably, incubation of $iPLA_2\beta$ with oleoyl-CoA, but not other long-chain acyl-CoAs, resulted in robust stoichiometric covalent acylation of the enzyme (~1:1 oleoyl/ $iPLA_2\beta$ mol ratio). Moreover, mutagenesis of Ser-465 or pretreatment of wild-type $iPLA_2\beta$ with (E)-6-(bromomethylene)-3-(1-naphthalenyl)-2H-tetrahydropyran-2-one (BEL) unexpectedly increased acylation of the enzyme, demonstrating the presence of a second reactive nucleophilic residue that participates in the formation of the fatty acyl-$iPLA_2\beta$ adduct. Partial trypsinolysis of oleoylated $iPLA_2\beta$ and MALDI-MS analysis localized the acylation site to a hydrophobic 25 kDa fragment (residues ~400-600) spanning the active site to the calmodulin (CaM) binding domain. Intriguingly, calmodulin-$Ca^{2+}$ blocked acylation of $iPLA_2\beta$ by oleoyl-CoA. Remarkably, addition of low micromolar concentrations (5 μM) of oleoyl-CoA resulted in significant reversal of calmodulin-mediated inhibition of $iPLA_2\beta$ phospholipase $A_2$ activity. These results collectively identify the robust and molecular species specific $iPLA_2\beta$ catalyzed hydrolysis of acyl-CoA, demonstrate the presence of a second active site that mediates $iPLA_2\beta$ autoacylation, and identify long-chain acyl-CoAs and their cogeners as potential candidates for calcium influx factor.

Phospholipases $A_2$ ($PLA_2$s) catalyze the hydrolysis of ester-linked fatty acids from glycerophospholipids, thereby regulating numerous cellular processes through the generation of lysophospholipids, free fatty acids (e.g. arachidonic acid) and their downstream metabolites. In eukaryotes, $PLA_2$s are broadly categorized into three families: secretory ($sPLA_2$), cytosolic ($cPLA_2$), and calcium-independent phospholipases $A_2$ ($cPLA_2$) (1). Secretory $PLA_2$s are low molecular weight (~12-15 kDa) enzymes secreted into the extracellular space which require high micromolar to millimolar concentrations of $Ca^{2+}$ for catalysis (2,3). Six cytosolic phospholipases $A_2$ (α, β, γ, δ, ε, ξ) have been characterized at present, five of which (α, β, δ, ε, ξ) contain C2 domains that require sub-micromolar $Ca^{2+}$ for membrane association (4-7). Calcium-independent $PLA_2$s are intracellular, do not require calcium ion for membrane association or catalysis, and currently are comprised of seven family members (α, β, γ, δ, ε, ξ, η) (8-11), all of which contain conserved nucleotide-binding (GXGXR/KG) and lipase (GXSXG) consensus sequence motifs.

Long-chain fatty acyl-CoAs occupy a central position in mammalian neutral lipid and phospholipid metabolism. The biosynthesis of long-chain acyl-CoAs represents the first committed step in the flux of fatty acids into either lipid storage pools or towards energy (ATP) production. Extracellular non-esterified fatty acids arriving at the inner leaflet of the plasma membrane are trapped within the cell by thioesterification to CoASH catalyzed by acyl-CoA synthetases (12-14). Alternatively, fatty acyl-CoAs can be synthesized de novo from acetyl-CoA and malonyl-CoA by fatty acid synthase (15), to produce palmitoyl-CoA, which can then be acted upon by a long chain fatty acyl-CoA elongase to yield stearoyl-CoA (16). Importantly, the generation of mono-unsaturated (e.g. oleic) and polyunsaturated (e.g. arachidonic) fatty acyl species requires Δ5, Δ6, and Δ9 desaturases and elongases which utilize specific long chain fatty acyl-CoAs as substrates. Following synthesis, long chain acyl-CoAs are predominantly delivered to one of many acyl-CoA transferases (e.g. for the synthesis of phospholipids and triglycerides (17,18)) or used in the mitochondria or peroxisomes for β-oxidation (19-21).

In addition to their fundamental lipid metabolic roles, fatty acyl-CoAs can also participate in numerous regulatory cascades such as ion channel function (22-24), membrane fusion (25-27), and signal transduction (28,29). Modulation of signaling pathways by fatty acyl-CoAs can occur through either proximal association (e.g. activation of $K_{ATP}$-channels through interactions with the Kir6.2 pore-forming subunit (23)), covalent modification (e.g. through acylation of regulatory proteins by palmitoyl acyl-CoA transferases (30)), or by regulating transcriptional factor activity by acting as ligands for hepatic nuclear factor 4α (HNF-4α) (31,32).

Furthermore, acyl-CoAs have been implicated in peroxisome proliferator activated receptor (PPAR) inhibition (33, 34) and, conversely, non-esterified fatty acids have been shown to activate PPAR-mediated transcription (35-37). Thus, long chain acyl-CoA thioesterases may regulate cellular energy expenditure and signaling by determining acyl-CoA substrate availability, by metabolic "futile" cycling of acyl equivalents through acyl-CoA hydrolysis, by production of lipid second messengers, and by influencing transcription of PPAR and HNF-4α regulated genes through controlling the ratio of cellular free fatty acids to their CoA derivatives.

Multiple fatty acyl-CoA thioesterases have been purified from mammalian cytosol, peroxisomes, and mitochondria and have been cloned and characterized with respect to substrate selectivity, enzyme kinetics, and sensitivity to various inhibitors (38). In general, fatty acyl-CoA thioesterases have been tentatively classified as those which are structurally related to those induced by peroxisome proliferators (Type-I or Type-II thioesterases) and those which do not share significant sequence homology with these isoforms (38). Several other mammalian enzymes, such as lysophospholipases (39), secretory phospholipase $A_2$(40), and palmitoyl-protein thioesterases (41-43), have also been shown to exhibit acyl-CoA hydrolase activity. Interestingly, HNF-4α has been recently demonstrated to hydrolyze fatty acyl-CoAs, followed by binding of the fatty acid product to HNF-4α, thereby allowing crosstalk between the acyl-CoA and free fatty acid binding domains (44). Despite advances in identifying the proteins and enzymes mediating acyl-CoA binding, hydrolysis, and transcriptional signaling, the metabolic significance and integrated functional roles of these chemical entities in different cellular, subcellular, and tissue-specific contexts remains incompletely understood.

Calcium-independent phospholipase $A_2\beta$ has been implicated as an important participant in multiple and diverse cellular processes such as agonist-induced arachidonic acid release (45,46), apoptosis (47,48), lymphocyte proliferation (49), fat cell differentiation (50), insulin secretion (51) and lysolipid production mediating capacitive calcium influx (52, 53). In addition, recent tests utilizing transgenic mice selectively overexpressing $iPLA_2\beta$ in myocardium have provided evidence that cardiac ischemia activates $iPLA_2\beta$, precipitating ion channel dysfunction and resultant malignant ventricular tachyarrythnias which can be suppressed by pretreatment with the mechanism-based $iPLA_2$ inhibitor, (E)-6-(bromomethylene)-3-(1-naphthalenyl)-2H-tetrahydropyran2-one (BEL) (54). Previously, we have demonstrated that $iPLA_2\beta$ activity is regulated through calmodulin-mediated inhibition of phospholipase $A_2$ activity in the presence of physiologic concentrations of calcium (~200 nM) (55). Subsequent structural studies identified the calmodulin binding domain of $iPLA_2\beta$, containing "1-9-14" and IQ sequence motifs, located within a ≈15 kDa region approximately 50 amino acid residues from the C-tenninus (56). During cellular stimulation and the depletion of intracellular $Ca^{2+}$ stores, activation of $iPLA_2\beta$ has been proposed to occur through disassociation of the $iPLA_2\beta$-CaM complex (46,53), potentially through the actions of a low molecular weight cellular component known as calcium influx factor (CIF) (53,57). Although CIF was first described and partially characterized more than 10 years ago as a diffusible messenger released upon intracellular $Ca^{2+}$ store depletion which stimulated $Ca^{2+}$ influx through the plasma membrane (58,59), the precise molecular identity of CIF has largely remained a mystery and for this reason, its existence has been controversial.

In addition to its calmodulin binding domain, $iPLA_2\beta$ possesses a conserved nucleotide binding motif (GXGXR/KG) which binds ATP, resulting in both enzyme stabilization and activation (60,61). Thus, modulation of $iPLA_2\beta$ activity by ATP provides a potential mechanism through which phospholipid hydrolysis and second messenger generation can be regulated by the energy state (e.g. ATP/ADP ratio) of the cell. From this perspective, we considered the possibility that $iPLA_2\beta$ might also bind and hydrolyze long-chain acyl-CoAs, given the structural similarity of the 3'-phosphoadenosine moiety of CoA to ATP. In this manuscript, we demonstrate that $iPLA_2\beta$ catalyzes the hydrolysis of saturated long chain acyl-CoAs present as either monomers or as guests in host membrane vesicles at physiologic concentrations (1-5 mol %). Moreover, robust and highly selective covalent acylation of $iPLA_2\beta$ by oleoyl-CoA occurred at a second site(s) within the catalytic domain which is protected from oleoylation by calcium-activated calmodulin. Finally, oleoyl-CoA was found to attenuate calmodulin-mediated inhibition of $iPLA_2\beta$ phospholipase $A_2$ activity.

The above describes the previously unrecognized fatty acyl-CoA thioesterase catalytic activity and fatty acyl-CoA dependent covalent acylation of $iPLA_2\beta$, thereby revealing an additional level of chemical complexity in the integration and participation of this multifunctional signaling enzyme in the regulation of numerous cellular pathways.

In an aspect, pharmaceutical compositions and preparations are made in a manner well known in the pharmaceutical art. One exemplary preparation utilizes a vehicle of physiological saline solution comprising at least one of a chemical agent, siRNA, and penetrant that is combined with a pharmaceutically acceptable carrier. A suitable buffer, such as sterile water, may be present in the composition.

In an aspect, the carrier can also contain other pharmaceutically-acceptable excipients and additives for modifying or maintaining pH, osmolarity, viscosity, clarity, color, sterility, stability, rate of dissolution, or odor of the formulation. Similarly, the carrier may contain still other pharmaceutically acceptable excipients for modifying or maintaining release or absorption or penetration.

It is also contemplated that some formulations are more conveniently administered orally in an effective amount and dosage. Such formulations are preferably encapsulated and formulated with suitable carriers in solid dosage forms.

The construction of a suitable vector can be achieved by any of the methods well-known in the art for the insertion of exogenous DNA into a vector. see Sambrook et al., 1989, Molecular Cloning, A Laboratory Manual, Cold Spring Harbor Press, N.Y.; Rosenberg et al., Science 242:1575-1578 (1988); Wolff et al., PNAS 86:9011-9014 (1989). For Systemic administration with cationic liposomes, and administration in situ with viral vectors, see Caplen et al., Nature Med., 1:39-46 (1995); Zhu et al., Science, 261:209-211 (1993); Berkner et al., Biotechniques, 6:616-629 (1988); Trapnell et al., Advanced Drug Delivery Rev., 12:185-199 (1993); Hodgson et al., BioTechnology 13:222 (1995).

The following Example illustrates the best currently-known method of practicing this invention which is described in detail in order to facilitate a clear understanding of the discovery. It should be understood, however, that the detailed expositions of the application of the invention, while indicating exemplary embodiments, are given by way of illustration only and are not to be construed as limiting the discovery since various changes and modifications within the spirit of the discovery will become apparent to those skilled in the art from this detailed description. In the following examples, which illustrate the invention, and throughout the specification, parts and percent are by weight unless otherwise indicated.

Example

Materials—[1-$^{14}$C]-palmitoyl-CoA and [1-$^{14}$C]-oleoyl-CoA, and 1-palmitoyl-2-[1-$^{14}$C]-oleoyl-sn-glycero-3-phosphocholine were obtained from Perkin-Elmer. [1-$^{14}$C]-Arachidonoyl-CoA, [1-$^{14}$C]-myristoyl-CoA, [1-$^{14}$C]-stearoyl-CoA, and [methyl-14C] human albumin were obtained from American Radiolabeled Chemicals. 1-palmitoyl-2-oleoyl-sn-glycero-3-phosphocholine (POPC) and 1,2-dioleoyl-sn-glycero-3-[phospho-L-serine] (DOPS) were purchased from Avanti Polar Lipids. 2-decanoyl-1-(O-(11-(4,4-difluoro-5,7-dimethyl-4-bora-3α,4α-diaza-s-indacene-3-propionyl)amino)undecyl)-sn-glycero3phosphocholine (BODIPY-PC) was purchased from Invitogen. High purity bovine calmodulin was obtained from Calbiochem. Most other materials were obtained from either Sigma or Fisher Scientific. BEL was purchased from Cayman Chemical and separated into individual enantiomers as described previously (62).

Expression and Affinity Purification of iPLA2β(His)$_6$ (peptide disclosed as SEQ ID NO: 4) from Sf9 Cells—Following infection of 3×100 ml cultures of Sf9 cells (1.5×10$^6$ cells/ml) with baculovirus encoding $iPLA_2\beta(His)_6$ (peptide disclosed as SEQ ID NO: 4) for 48 hr, cells were harvested by centrifugation (900×g for 10 mm), washed once with Grace's Insect Medium without serum, and resuspended in 30 ml of 25 mM sodium phosphate, pH 7.8, 20% glycerol, 2 mM β-ME, 5 µg/ml aprotinin, 5 µg/ml leupeptin. After lysing the cells by sonication (30×1 s bursts), the homogenate was centrifuged at 100,000×g for 1 h to obtain the cytosol to which NaCl was added to a final concentration of 250 mM. The cytosol was then mixed by inversion with 3 ml of HIS-Select-Co2+ affinity resin (Sigma) for 1 hr and the cytosol-resin suspension was poured into a Pharmacia 1×10 cm column. Following washing of the settled resin with 30 mL of Buffer A (25 mM sodium phosphate, pH 7.8 containing 500 mM NaCl, 20% glycerol, and 2 mM β-ME), bound protein was eluted from the column at a flow rate of 0.25 ml/min utilizing a 250 mM imidazole gradient in Buffer A (50 ml total volume) generated using a Pharmacia FPLC system. Column fractions were assayed for $iPLA_2$ activity as described below, pooled and dialyzed overnight against Buffer B (25 mM imidazole, pH 7.8 containing 20% glycerol, 1 mM DTT, and 1 mM EGTA). The dialyzed sample was applied to a 2.5 ml column of ATP agarose equilibrated with Buffer B and washed with Buffer B containing 1 mM AMP and 50 mM NaCl. Bound $iPLA_2\beta$ $(His)_6$ (peptide disclosed as SEQ ID NO: 4) was eluted with Buffer B containing 2 mM ATP and 50 mM NaCl, dialyzed against Buffer B (EGTA concentration was reduced to 0.1 mM) containing 50 mM NaCl to remove ATP, flash frozen in liquid nitrogen, and stored at −80° C. Approximately 1 mg (65% yield) of $iPLA2\beta(His)_6$ (peptide disclosed as SEQ ID NO: 4) with a specific activity of 500 nmol oleic acid $min^{-1} \cdot mg^{-1}$ utilizing 5 μM $[^{14}C]$-POPC as substrate was typically recovered from 300 ml of Sf9 cell culture by this procedure.

Phospholipase $A_2$ and Acyl-CoA Hydrolase Enzymatic Assays—Purified recombinant $iPLA_2\beta(His)_6$ (peptide disclosed as SEQ ID NO: 4) (0.1-1 μg) was incubated with radiolabeled phospholipid or acyl-CoA in 25 mM Tris-HCl, pH 7.2 containing 1 mM EGTA (200 μl final volume) for 1-2 mm at 37° C. In tests using acyl-CoAs as guests in host phospholipid bilayers, radiolabeled acyl-CoAs were incorporated into POPC/DOPS (90:10 mol %) vesicles before addition to the reaction mix. Long-chain acyl-CoAs have been previously demonstrated to integrate into lipid bilayers within seconds (63). Incorporation of acyl-CoA into the POPC/DOPS vesicles employed was determined as described previously (64). Reactions were terminated by extraction of the released radiolabeled fatty acids into 100 μl butanol, separation of fatty acids from unreacted substrate by thin layer chromatography, and quantitation by scintillation spectroscopy as previous described (65). For tests examining the effects of acyl-CoAs on calmodulin-mediated inhibition of $iPLA_2\beta$, phospholipase $A_2$ activity was continuously measured utilizing a SPECTRAmax GEMINI XS Dual-Scanning Microplate Spectrofluorometer (Molecular Devices). BODIPY-PC substrate (1.17 μM in DMSO, 5 μM final concentration) was co-sonicated (10 mm. at 40% power, 50% duty cycle) with POPC (95 μM final concentration) in 25 mM HEPES, pH 7.2. Oleoyl-CoA and $CaCl_2$ were added at the indicated concentration to the lipid vesicles before addition to $iPLA_2\beta$ with or without CaM (preincubated on ice for 10 mm) present in individual wells of a black 96-well microtiter plate. Fluorescence readings were acquired at 20 sec intervals for 5 mm at 37° C. utilizing excitation/emission wavelengths of 495/515 nm, respectively.

Covalent Modification of $IPLA_2\delta$ with $[^{14}C]$-long chain Acyl CoAs—Purified recombinant $iPLA_2\beta(His)_6$ (peptide disclosed as SEQ ID NO: 4) was incubated with POPC vesicles containing 10 mol % $[1-^{14}C]$-acyl-CoA for 1 h at 37° C. In some tests, $iPLA_2\beta$ $(His)_6$ (peptide disclosed as SEQ ID NO: 4) was pre-incubated with BEL (3 min at 23° C.), N-ethylmaleimide (5 min at 30° C.) or iodoacetamide (5 min at 30° C.) prior to addition of radiolabeled acyl-CoA. Chloroform/methanol precipitation of some samples was performed as described (66) utilizing 15 μg of bovine serum albumin as carrier. In tests to examine the nature of the covalent linkage between oleic acid and $iPLA_2\beta$, acid (HCl), base (NaOH), and hydroxylamine were added to the indicated concentrations and the samples were incubated at 30° C. for 1 h. Bovine serum albumin (15 μg) and SDS-PAGE loading buffer were then added to each sample prior to dialysis against 50 mM Tris-HCl, pH 6.8 containing 10% glycerol and 1% SDS for 4 h. Samples were electrophoresed by SDS-PAGE, fixed (40% methanol containing 10% acetic acid), stained with Coomassie Blue R-250, incubated in Amplify fluorographic reagent, dried, and exposed to Kodak Biomax MR film for 2-5 days at −80° C.

Partial Trypsinolysis of Oleoylated $IPLA_2\beta$—Purified $iPLA_2\beta(His)_6$ (peptide disclosed as SEQ ID NO: 4) (10 μM) was incubated with 50 μM $[1-^{14}C]$-oleoyl-CoA or unlabeled oleoyl-CoA in 25 mM imidazole, pH 7.8 containing 50 mM NaCl, 0.1 mM EGTA, 1 mM DTT, and 20% glycerol for 1 h at 37° C. Excess $[1-^{14}C]$-oleoyl-CoA was removed by using a Micro Bio-Spin (Bio-Rad) column equilibrated with the above buffer. Recovered $iPLA_2\beta$ was partially digested with trypsin (1:25 w/w) for 1-30 mm at 37° C. Tryptic peptides were separated by SDS-PAGE, fixed in 40% methanol/10% glacial acetic acid, stained with Coomassie Blue, and destained in the fixation solution. Gels containing the radiolabeled peptide fragments were soaked in Amplify fluorogenic reagent (Amersham), dried, and exposed to film. In parallel samples utilizing unlabeled oleoyl-CoA, the band corresponding to the ~25 kDa radiolabeled was excised, cut into ~1×1 mm pieces, and destained further by washing with 50% acetonitrile at 37° C. The gel pieces were then dried in a Speed-Vac, resuspended in 50 mM ammonium bicarbonate (100 μL) containing 0.5 μg of sequencing grade modified trypsin (Promega), and incubated 12 h at 37° C. After aliquoting the supernatant solution to a separate tube, residual peptides in the gel pieces were extracted into 50% acetonitrile, 20% isopropanol, 0.1% TFA, combined with the supernatant solution, and concentrated utilizing a Speed-Vac.

MALDI-TOF of $iPLA_2\beta$ Tryptic Fragments—Concentrated peptide samples were diluted with 0.5% TFA, absorbed to a C18 Zip-Tip (Millipore), and desorbed with a solution comprised of 50% acetonitrile, 20% isopropanol, 0.1% TFA, and containing in addition 5 mg/ml α-cyano-4-hydroxycinnamic acid. Samples were applied to 192-spot sample plates (ABI) and allowed to air dry. Mass spectral (MS) analysis was performed utilizing an Applied Biosystems 4700 Proteomics Analyzer (Framingham, Mass.), which possesses a 200 Hz Nd:YAG laser operating at 355 nm. Mass accuracy of the instrument was externally calibrated to the 4700 Proteomics Analyzer Calibration Mixture of peptides. For MALDI-MS analysis, spectra were obtained by the accumulation of 2500 consecutive laser shots at a collision energy of 1 kV with air serving as the collision gas. Calculations of predicted peptide and peptide fragment masses were performed using programs developed at the UCSF Mass Spectrometry Facility (http://prospector.ucsf.edu).

SDS-PAGE was performed according to Laemmli (67). Silver staining of SDS-PAGE gels was performed as described (68). Protein concentration was determined by a version of the Bradford protein assay (Bio-Rad) with bovine serum albumin as a standard.

Results $iPLA_2\beta$ Hydrolyzes Fatty Acyl-CoAs as Either Monomers or as Guests in Membrane Bilayers.

Calcium-independent phospholipase $A_2\beta$ contains a highly conserved nucleotide binding domain (GxGxR/KG) which tightly binds ATP, resulting in both stabilization and activation of the enzyme (60,61). Due to the structural similarity between ATP and the 3'-phosphoadenosine moiety present in CoA, we hypothesized that iPLA$_2$β could bind to, and potentially hydrolyze, the thioester linkage of long chain fatty acyl-CoAs. Accordingly, we overexpressed iPLA$_2$β (His)$_6$ (peptide disclosed as SEQ ID NO: 4) in Sf9 cells and purified the enzyme to apparent homogeneity (as determined by SDS-PAGE and silver staining) by sequential cobalt and ATP affinity chromatographies as described in Experimental Procedures. Initial assays with iPLA$_2$β utilizing supramicellar concentrations of palmitoyl-CoA (100 µM) typically used for acyl CoA thioesterases revealed very low rates of iPLA$_2$β-catalyzed palmitoyl-CoA hydrolysis (FIG. 1A). Remarkably, robust rates of palmitoyl-CoA thioesterase activity catalyzed by iPLA$_2$β were demonstrated at low micromolar concentrations of palmitoyl-CoA with a maximal rate of ≈250 nmol palmitic acid×min$^{-1}$×mg$^{-1}$ protein at 2.5 µM palmitoyl-CoA (FIG. 1A). Similar requirements for low acyl-CoA concentrations due to substrate-mediated inhibition were observed in previous studies of a purified mitochondrial thioesterase from rabbit myocardium (69) and peroxisomal acyl-CoA thioesterase 2 (70). It should be recognized that significant palmitoyl-CoA-mediated inhibition of iPLA$_2$β occurs below the critical micelle concentration of palmitoyl-CoA and may imply the presence of a second acyl CoA binding site on the enzyme (vide infra).

iPLA$_2$β Catalyzes Hydrolysis of Palm-CoA Present as Guests in a Host Phospholipid Bilayer.

Since iPLA$_2$β would likely be expected to encounter acyl-CoAs in a membrane bilayer environment in vivo, we examined whether the enzyme could hydrolyze palm-CoA present as a guest (at a low mol %) in phospholipid host vesicles. Purified iPLA$_2$β effectively hydrolyzed palmitoyl-CoA at physiologically relevant concentrations of acyl-CoA (i.e. 1-5 mol %) when present as a guest in 1-palmitoyl-2-oleoyl-sn-glycero-3-phosphocholine (POPC)/1,2-dioleoyl-sn-glycero-3-phospho-L-serine (DOPS) host bilayers (9:1 mol ratio) (FIG. 1B). This was surprising since POPC is an excellent substrate for iPLA$_2$β and would be expected to efficiently compete with the palmitoyl-CoA as substrate. To determine whether iPLA$_2$β could hydrolyze acyl-CoAs other than palmitoyl-CoA, incubations were performed with a series of different long-chain acyl CoA molecular species in host POPC/DOPS bilayers. A dramatic selectivity for myristoyl- and palmitoyl-CoA hydrolysis was observed (up to 20-fold) in comparison to stearoyl-, oleoyl-, and arachidonyl-CoAs (FIG. 2). Thus, iPLA$_2$β displays substantial selectivity for saturated acyl-CoA substrates (14-16 carbons in length) in comparison to longer unsaturated acyl-CoA molecular species (C18:1 and C20:4) in the presence of membrane bilayers.

Determination of the Active Site Nucleophile Mediating Palmitoyl-CoA Hydrolysis.

Site-directed mutagenesis of the lipase consensus motif serine (GTS$^{465}$TG) (SEQ ID NO: 5) of iPLA$_2$β to alanine has been previously demonstrated to ablate phospholipase A$_2$ activity (10). To determine if Ser-465 was equally crucial for iPLA$_2$β acyl-CoA thioesterase activity, we mutated S465 to alanine and compared the phospholipase A$_2$ and palmitoyl-CoA hydrolase activities of the affinity purified mutant protein to its wild-type counterpart. Importantly, the S465A iPLA$_2$β(His)$_6$ (peptide disclosed as SEQ ID NO: 4) bound to ATP agarose (as determined by Western analysis) demonstrating that the mutant protein was properly folded near the region of nucleotide binding site ($^{431}$GGGVKG$^{436}$) (SEQ ID NO: 6) which is ≈30 amino acid residues away from the lipase consensus site. As expected, substitution of an alanine residue at Ser-465 abolished calcium-independent PLA$_2$ activity utilizing POPC as substrate (FIG. 3). Importantly, hydrolysis of palmitoyl-CoA incorporated into POPC/DOPS vesicles also was virtually eliminated in the S465A mutant (FIG. 3), indicating that the active site serine hydroxyl likely serves as the primary nucleophile for both phospholipase A$_2$ and acyl-CoA thioesterase reactions catalyzed by iPLA$_2$β.

Chiral Mechanism-Based Inhibition of Acyl-CoA Hydrolysis by (R)- and (S)-BEL.

In previous work, we demonstrated that racemic (E)-6-(bromomethylene)-3-(1-naphthalenyl)-2H-tetrahydropyran-2-one (BEL) is a potent and highly selective inhibitor of both iPLA$_2$β (IC$_{50}$~0.2 µM) and iPLA$_2$γ (IC$_{50}$~3 µM) phospholipase A$_2$ activities (11,71,72). Through resolving the enantiomers of BEL by chiral HPLC, we have further shown that (S)- and (R)-BEL are selective for iPLA$_2$β and iPLA$_2$γ, respectively (62). To determine if the distinct enantiomers of BEL had similar effects on iPLA$_2$β palmitoyl-CoA thioesterase activity, (R) and (S) BEL were pre-incubated with purified iPLA$_2$β(His)$_6$ (peptide disclosed as SEQ ID NO: 4) prior to addition of radiolabeled palmitoyl-CoA as guest in POPC/DOPS host bilayers. As seen in FIG. 4, (S)-BEL inhibited iPLA$_2$β palm-CoA hydrolase activity with an IC$_{50}$ of approximately 0.1 µM, whereas (R)-BEL was ≈8-fold less effective (IC$_{50}$=0.8 µM). Thus, the selectivity of the BEL enantiomers for inhibiting iPLA$_2$β palmitoyl-CoA thioesterase activity is virtually identical to that previously observed for inhibition of phospholipase A$_2$ activity (62). Collectively these results suggest that both long-chain acyl-CoA and phospholipid substrates utilize the same mechanism and hydrolytic site (binding domain and catalytic residue(s)) in iPLA$_2$β for hydrolysis.

Identification of Specific Autoacylation of iPLA$_2$β by Oleoyl-CoA.

Since prior work has demonstrated that various proteins such as rhodopsin (73), G-protein α subunits (74, 75), and PKC (76) are autoacylated in the presence of palmitoyl-CoA, we sought to determine if iPLA$_2$β could become similarly acylated in the presence of various saturated and unsaturated long-chain acyl-CoA substrates. Remarkably, although incubations with [1-$^{14}$C]-myristoyl-CoA, [1-$^{14}$C]-palmitoyl-CoA, and [1-$^{14}$C]-stearoyl-CoA demonstrated either no observable or only diminutive acylation of iPLA$_2$β following SDS-PAGE, those containing [1-$^{14}$C]-oleoyl-CoA resulted in the dramatic radiolabeling of iPLA$_2$β which was 10-100 fold greater than their saturated counterparts (FIG. 5). Furthermore, incubations with [1-$^{14}$C]-arachidonoyl-CoA resulted in ≈25-fold-less signal intensity than with [1-$^{14}$C]-oleoyl-CoA, but iPLA$_2$β was still arachidonoylated under these conditions (FIG. 5). To our surprise, similar tests with the iPLA$_2$β S465A mutant displayed a shift in the selectivity of acylation, i.e. autoacylation was greatest with stearoyl-CoA and labeling with palmitoyl-CoA became clearly detectable (FIG. 5). In addition, labeling of the S465A mutant with oleoyl-CoA was notably reduced relative to wild-type iPLA$_2$β. Similar incubations of BEL-pretreated iPLA$_2$β with the different [1-$^{14}$C]-acyl-CoAs revealed marked increases in acylation with palmitoyl-CoA and stearoyl-CoA that were not observed with the wild-type protein (FIG. 5). Thus, inactivation of the catalytic site through either site directed mutagenesis or pretreatment with BEL does not abolish iPLA$_2$ acylation supporting the existence of a second active site which catalyzes autoacylation.

To determine the stoichiometry of iPLA$_2$β acylation with oleoyl-CoA, we incubated increasing concentrations of [1-$^{14}$C]-oleoyl-CoA with iPLA$_2$β and compared the intensity of radiolabeleing to a standard curve generated from adding incremental amounts of [methyl-$^{14}$C]-human serum albumin of known specific activity (FIG. 6). The results demonstrate that approximately 1 mole of [1-$^{14}$C]-oleic acid was incorporated per mole of iPLA$_2$β in the presence of POPC vesicles containing up to a 5-fold molar excess of [1-$^{14}$C]-oleoyl-CoA relative to iPLA$_2$β. One potential consequence of iPLA$_2$β oleoylation is alteration of catalytic activity, either toward phospholipid or acyl-CoA substrates. To address this possibility, iPLA$_2$β was incubated with or without oleoyl-CoA and then purified by Co$^{2+}$ metal affinity chromatography to remove residual oleoyl-CoA. Results from these tests indicated that oleoylation did not significantly affect either iPLA$_2$β mediated POPC or palmitoyl-CoA hydrolysis (data not shown). Thus, iPLA$_2$β autoacylation with oleoyl-CoA occurs at site which does not block accessibility of substrate to, or inhibit release of products from, the active site.

Although SDS-PAGE would be expected to remove the overwhelming majority of non-covalently associated lipid, it was remotely conceivable that the hydrophobicity of the iPLA$_2$β putative substrate binding site could possibly cause tight non-covalent association of radiolabeled oleoyl-CoA or oleic acid to the denatured iPLA$_2$β. To exclude this possibility, iPLA$_2$β was incubated with [1-$^{14}$C]-oleoyl-CoA, precipitated with chloroform/methanol and the resultant pellet was extensively washed with 70% acetone (FIG. 7, lane 2) in which both oleic acid and oleoyl-CoA are readily soluble. This treatment did not result in an appreciable decrease in signal intensity, indicating that the [1-$^{14}$C]-oleate is covalently bound to iPLA$_2$β. Since esterification of fatty acids to proteins has been demonstrated to occur through either amide, oxyester, or thioester linkages which can be distinguished through chemical treatment with strong acid (HCl), strong base (NaOH), or neutral hydroxylamine, additional tests were performed to determine the nature of the covalent linkage. In the case of [1-$^{14}$C]-oleoyl-iPLA$_2$β, addition of either 1 N HCl or 1-2 N neutral hydroxylamine did not result in a significant decrease in radiolabeling, while addition of 1 NaOH completely eliminated the majority of covalently bound [1-$^{14}$C]-oleate (FIG. 7). The insensitivity of [1-$^{14}$C]-oleoyl-iPLA$_2$β to hydroxylamine and HCl would indicate the absence of thioester and oxyester linkages, respectively, while the disappearance of radiolabeling in the presence of NaOH is consistent with an amide linkage. Pretreatment of iPLA$_2$β with N-ethylmaleimide and iodoacetamide decreased radiolabeling with [1-$^{14}$C]-oleoyl-CoA (FIG. 7), indicating that free thiol (cysteine) groups are important for either the formation of oleoyl-iPLA$_2$β acylintermediate(s) or for its subsequent transfer to the terminal nucleophilic acceptor residue(s) in iPLA$_2$β. Remarkably, acylation of iPLA$_2$β was not detectable utilizing 1-palmitoyl-2-[1-$^{14}$C]-oleoyl-sn-glycero-3-phosphocholine (with or without CoASH) (FIG. 7), suggesting that the acyl-enzyme intermediates formed with oleoyl-CoA are fundamentally distinct from those generated by POPC where the preferred nucleophile is water (hydrolysis) while with oleoyl-CoA, endogenous nucleophilic iPLA$_2$β amino acid residue(s) serve as the preferred donors, resulting in production of a stable and isolatable acyl enzyme.

Attempts at Mass Spectrometric Identification of the Hydrophobic Acylation Site and Trypsin Footprinting Determination of the Oleoylated Domain.

To identify the site(s) of oleoylation in iPLA$_2$β, we utilized MALDI-MS to examine tryptic digests of the protein, specifically searching for unique peptide peaks that were 264.245 mass units (i.e. C 18:1-H$_2$O greater than their respective parent peak. Despite multiple attempts utilizing a wide range of conditions (e.g. in-gel digests, solution digests, multiple proteases, combinations of proteases, organic solvent and detergent extraction/solubilization techniques, etc.), we were unable to identify potential candidate peaks for MALDI-MS/MS analysis. Overall, we were able to achieve 70% sequence coverage of iPLA$_2$β. Addition of oleate would be expected to increase the calculated water-octanol partition coefficient (log (P) value) of the modified peptide by 2.23, representing a significant increase in nonpolarity (for reference, log (P) for phenylalanine=1.000). The relatively low MALDI-MS signal intensity of hydrophobic peptides is well documented (77-79) and has been recently discussed in The Journal (80). Accordingly, we performed tests to identify the region of the protein which contained the oleoyl moiety through partial in-solution trypsinolysis of the [1-$^{14}$C]-oleoyl-iPLA$_2$β and subsequent separation of the radiolabeled peptide fragments by SDS-PAGE. Results from these tests revealed that the majority of the radioactivity was contained within a 25 kDa proteolytic fragment (FIG. 8). In-gel tryptic digestion and subsequent MALDI-MS analysis of the resultant peptides comprising this 25 kDa polypeptide determined that it encompassed residues 408-578 which contains both the nucleotide binding domain and the active site (Table I). Thus, acylation by oleoyl-CoA occurs within the catalytic domain of iPLA$_2$β, although it does not appear to inhibit or block substrate (i.e. palmitoyl-CoA or POPC) access to the active site serine (Ser-465) for catalysis.

Effects of Calcium Activated Calmodulin on iPLA$_2$β Mediated Acyl-CoA Hydrolysis.

Calcium-bound calmodulin has been previously demonstrated to bind to iPLA$_2$β and potently inhibit the phospholipase A$_2$ activity of the enzyme (55,81). We were therefore interested to determine if Ca$^{+2}$-CaM would have a similar effect on the acyl-CoA thioesterase activity of iPLA$_2$β. Although inclusion of Ca$^{+2}$-CaM inhibited the PLA$_2$ activity of recombinant iPLA$_2$β by ≈70-80%, the palmitoyl-CoA thioesterase activity was relatively unaffected (~10% inhibition) under similar conditions (FIG. 9). Thus, while the phospholipase A$_2$ activity of iPLA$_2$β is responsive to changes in intracellular calcium (via calmodulin), iPLA$_2$β would be expected to constitutively hydrolyze acyl-CoA thioesters independent of calcium concentration or the presence of calmodulin.

Calmodulin-Mediated Protection of iPLA$_2$β against Oleoylation by Oleoyl-CoA.

The proximity of the oleoylated iPLA$_2$β 25 kDa tryptic fragment to the calmodulin binding domain next led us to investigate whether Ca$^{2+}$CaM could protect the enzyme against covalent acylation by oleoyl-CoA. Although the addition of either calcium ions or CaM in the presence of EGTA alone did not alter the extent of oleoylation of iPLA$_2$β (FIG. 10), the combination of Ca$^{2+}$ and CaM significantly decreased autoacylation of the enzyme. From these results, acyl-CoA mediated acylation would be predicted to primarily occur after dissociation of the iPLA$_2$β/CaM complex.

Oleoyl-CoA Mediated Reversal of the Inhibition of iPLA$_2$β by Calmodulin.

Figure 11:
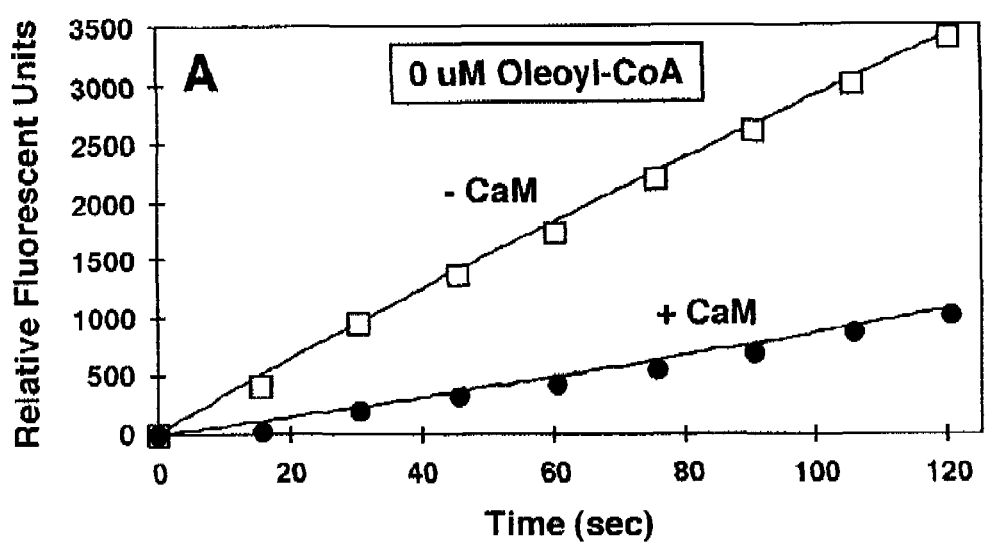
FIGS. 11A-11I depict reversal of $Ca^{2+}$/CaM-Mediated Inhibition of $iPLA_2\beta$ Activity by Oleoyl-CoA.
Figure 11:
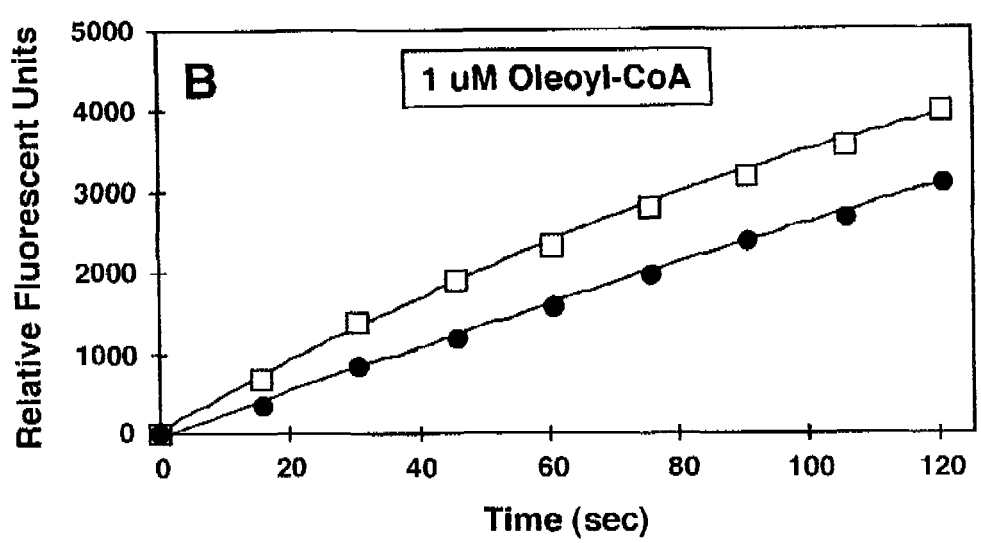
Figure 11:
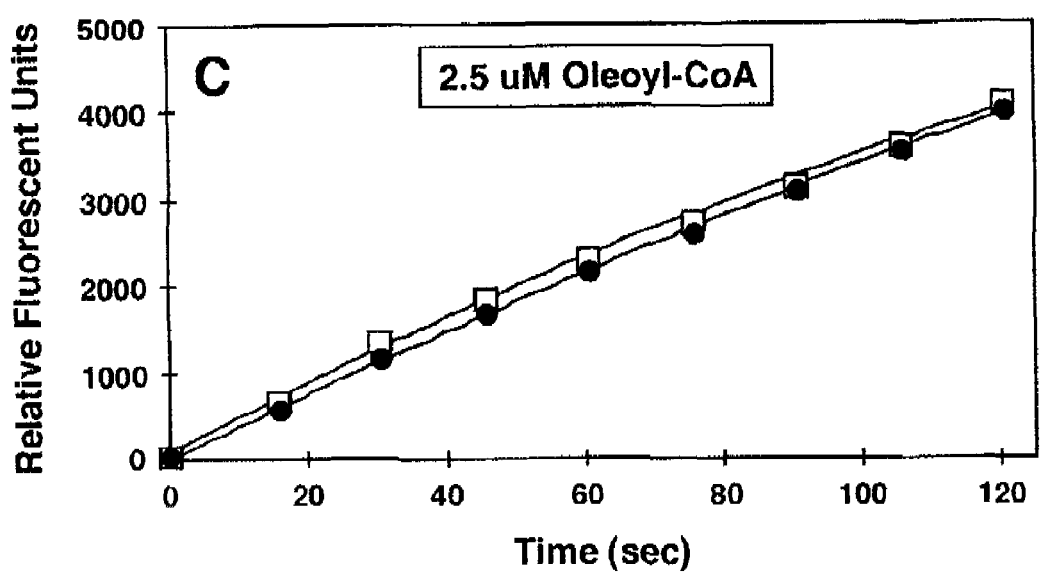
Figure 11:
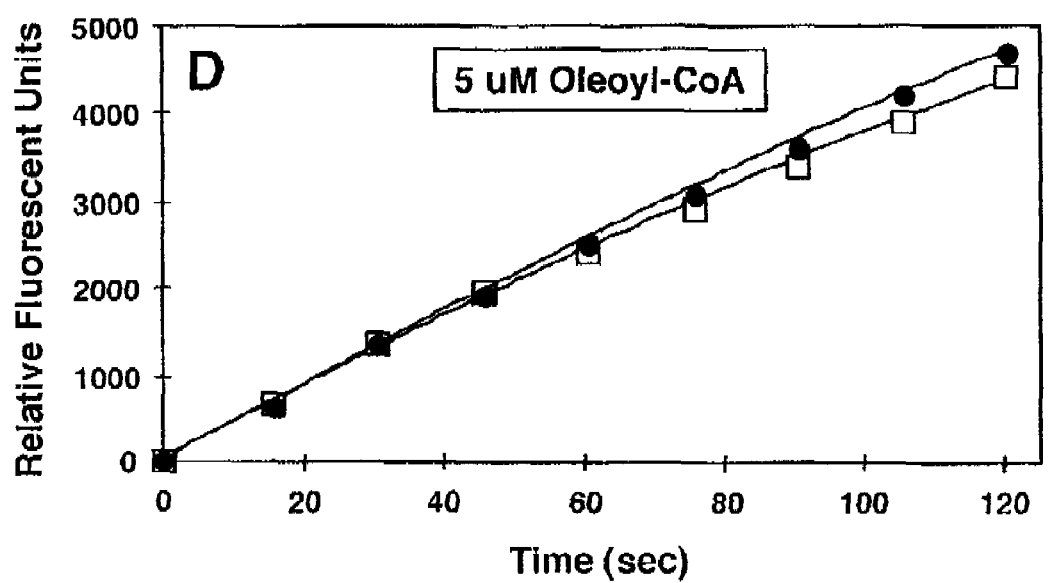
Figure 11:
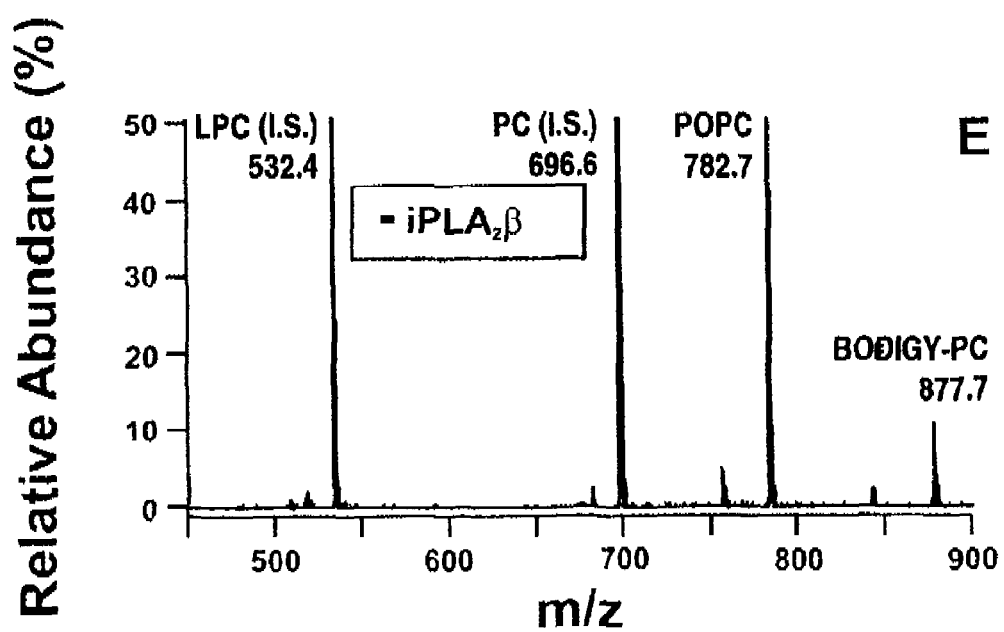
Figure 11:
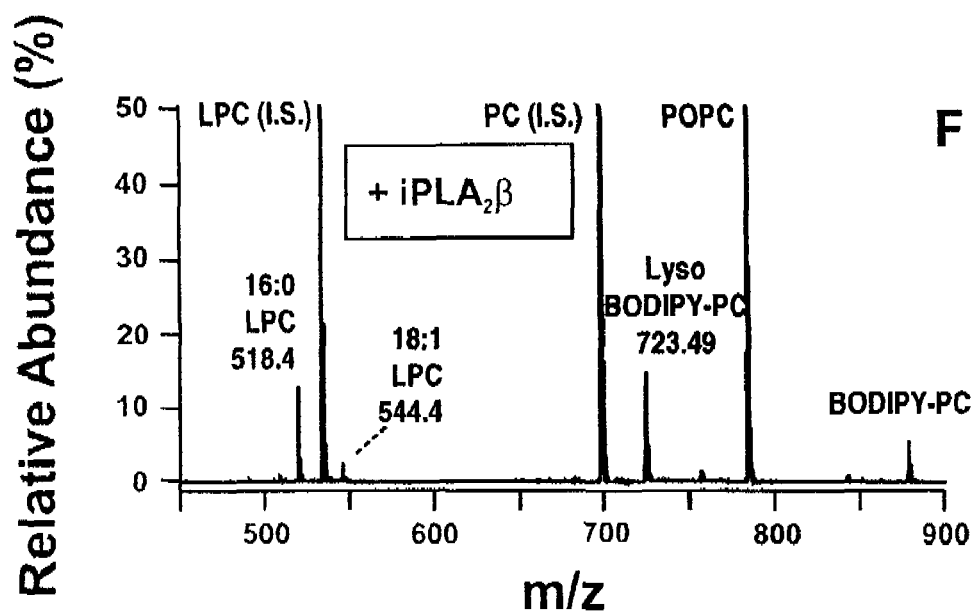
Figure 11:
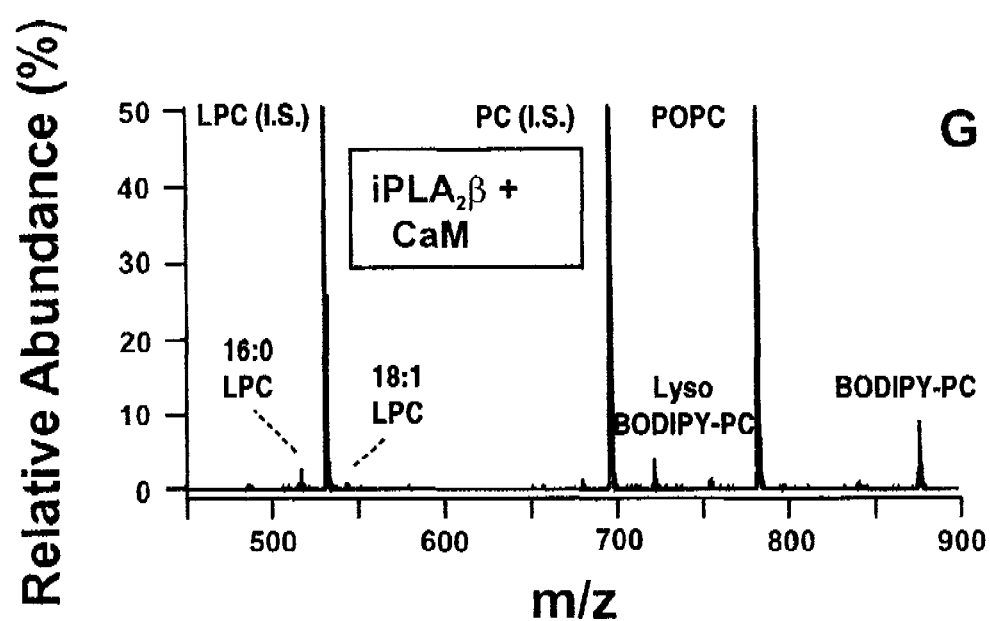
Figure 11:
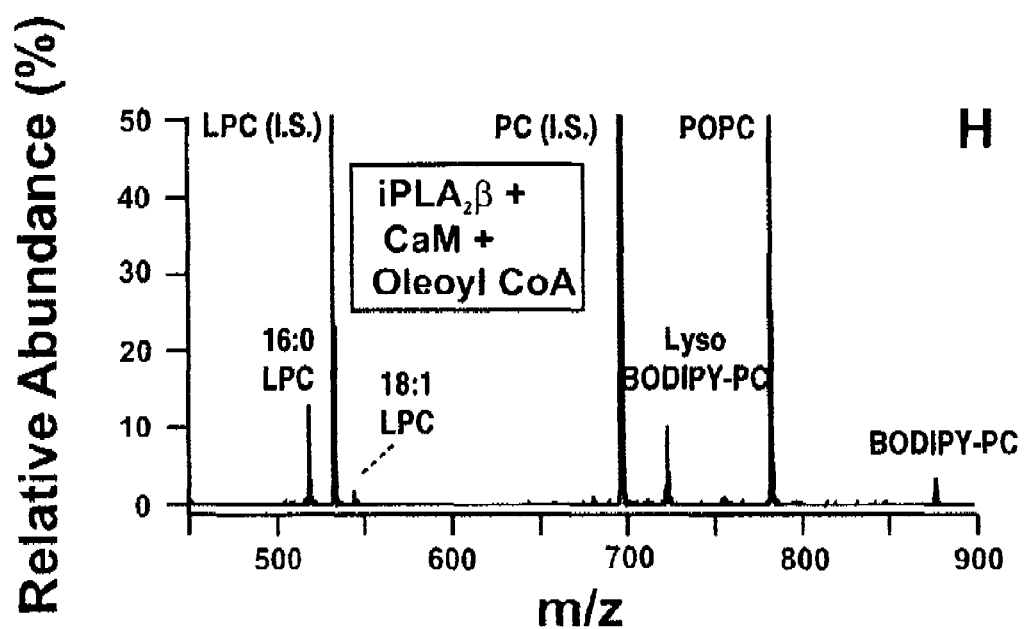
Figure 11:
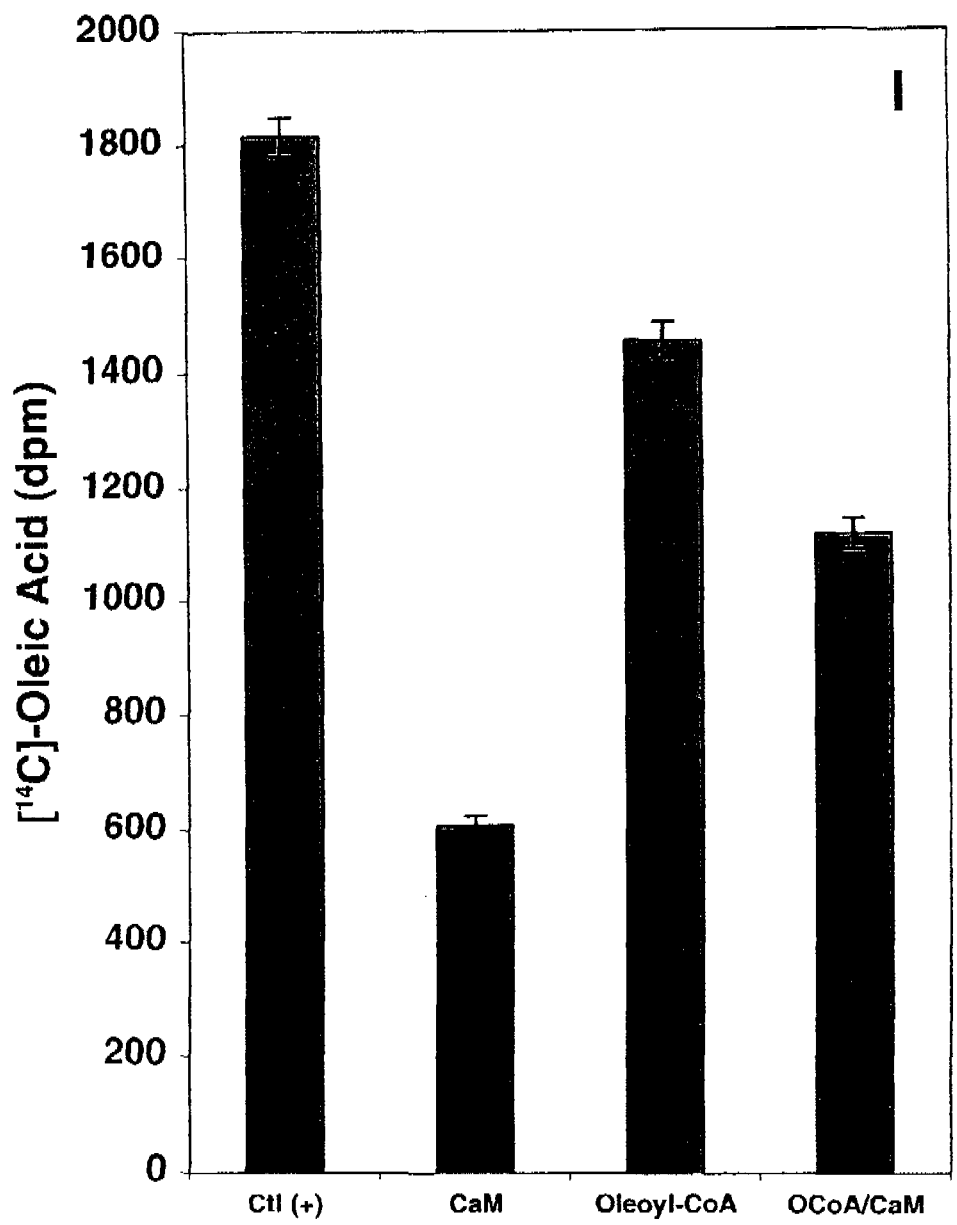

Depletion of intracellular calcium stores has been previously demonstrated to initiate the activation of iPLA$_2$β through a poorly understood process involving reversal of calmodulin inhibition of the enzyme by an unknown cellular metabolite referred to as calcium influx factor (CIF) (52,53, 57-59,82). To address the possibility that acyl-CoA could mitigate the inhibition of iPLA$_2$β by CaM, we utilized a real-time fluorescence assay employing the PLA$_2$ substrate, 2-decanoyl-1-(O-(11-(4,4-difluoro-5,7-dimethyl-4-bora-3α, 4α-diaza-s-indacene-3-propionyl) amino)undecyl)-sn-glycero-3-phosphocholine (BODIPY-PC), to measure the kinetic effects of oleoyl-CoA (guest in POPC (95 mol %)/BODIPY-PC (5 mol %) host vesicles) on CaM inhibition of iPLA$_2$β phospholipase $A_2$ activity. In the absence of calmodulin, iPLA$_2\beta$ efficiently hydrolyzes BODIPY-PC present at 5 mol % in a POPC background as demonstrated by a robust time dependent increase in fluorescence intensity (FIG. 11A). The presence of calcium ion did not appreciably affect the phospholipase $A_2$ activity of iPLA$_2\beta$ under these conditions (data not shown). In contrast, inclusion of Ca$^{2+}$-bound CaM inhibited iPLA$_2\beta$-catalyzed hydrolysis of BODIPY-PC by approximately 70-80% (FIG. 11A). Remarkably, addition of 1 mol % oleoyl-CoA could activate CaM-inhibited iPLA$_2\beta$ (≈40% of initial activity) (FIG. 11B) and the presence of 2.5-5 mol % oleoyl-CoA completely eliminated CaM mediated inhibition of iPLA$_2\beta$ (FIG. 11C-D) under these conditions.

To confirm that iPLA$_2\beta$ was in fact hydrolyzing BODIPY-PC and that the increase in fluorescence observed was not due to either protein-fluorophore or acylCoA-fluorophore interactions, the reaction substrates and products were extracted into chloroform/methanol in the presence of internal standards and subsequently quantified and analyzed by ESI-MS (83). As anticipated, the production of 2-lyso-1-(O-(11-(4,4-difluoro-5,7-dimethyl-4-bora-3α,4α-diaza-s-indacene-3-propionyl)amino)undecyl)-sn-glycero-3-phosphocholine, 1-palmitoyl-2-hydroxy-sn-glycero-3-phosphocholine, and 1-lyso-2-oleoyl-sn-glycero-3-phosphocholine was dependent upon the presence of iPLA$_2\beta$ and the amount of each product was diminished (~80%) by the presence of Ca$^{2+}$-bound CaM (FIG. 11E-G). Importantly, addition of 5 mol % of oleoyl-CoA to the POPC/BODIPY-PC vesicles in the presence of Ca$^{2+}$/CaM/iPLA$_2\beta$ completely reversed the inhibition of iPLA$_2\beta$ by Ca$^{2+}$/CaM as evidenced by the recovery of similar amounts of 16:0-LysoPC, 18:1-LysoPC, and Lyso-BODIPY-PC to that observed with iPLA$_2\beta$ alone (FIG. 11H). Finally, to establish that the effects of oleoyl-CoA on Ca$^{2+}$/CaM mediated inhibition of iPLA$_2\beta$ was not dependent on the presence of BODIPY-PC, similar tests were performed with 1-palmitoyl-2-[1-$^{14}$C]-oleoyl-sn-glycero-3-phosphocholine as substrate. Under these conditions, CaM inhibited iPLA$_2\beta$ activity by approximately 70% and the presence of oleoyl-CoA alone caused moderate inhibition (20%) of iPLA$_2\beta$ activity (FIG. 11I) presumably due to interactions with iPLA$_2\beta$ at or near the substrate binding site. The presence of oleoyl-CoA increased the activity of the CaM-inhibited iPLA$_2\beta$ to approximately 75% of the activity observed with oleoyl-CoA alone (FIG. 11I). Thus, these results demonstrate the rescue of the calmodulin-inhibited iPLA$_2\beta$ activity by oleoyl-CoA by three independent methods and identify fatty acyl-CoAs as potential candidates for calcium influx factor.

Discussion

Since its initial identification (84), purification (65) and cloning (9,10), calcium-independent phospholipase $A_2\beta$ has been demonstrated to be an important enzymatic mediator of multiple cellular regulatory processes which include agonist-stimulated arachidonic acid release (45,47,85,86), lymphocyte proliferation (49,87), store-operated Ca$^{2+}$ entry (46,52, 53), insulin secretion (51,88), ischemia-induced myocardial phospholipid hydrolysis (89,90), and malignant ventricular tachyarrhythmias (54). Prior studies have identified ATP (9) and calmodulin binding domains (56), ankyrin repeats (10, 91), multiple splice variants (92,93), proteolytic products (94,95), phosphorylation (9,96), and interaction with calmodulin kinase II β (97) each of which collectively serve as potential regulators of the pleiotropic signaling functions of iPLA$_2\beta$. It has been demonstrated that iPLA$_2\beta$ efficiently catalyzes the hydrolysis of saturated fatty acyl-CoAs at physiologically relevant concentrations, is selectively autoacylated by oleoyl-CoA, is protected from autoacylation by Ca$^{2+}$-CaM, and is rescued from calmodulin-mediated inhibition by oleoyl-CoA.

Optical antipodes of BEL and site-directed mutagenesis of Ser-465 inhibit both iPLA$_2\beta$ thioesterase and phospholipase $A_2$ activities to identical degrees, indicating that the same active site and nucleophile (Ser-465) is utilized for both reactions. In contrast, Ca$^{2+}$-CaM significantly inhibited only the phospholipase $A_2$ activity of iPLA$_2\beta$, whereas the acylCoA thioesterase activity of the enzyme was unaffected under similar conditions. This suggests that the "monoacyl" acyl-CoA substrate may have greater access to the iPLA$_2\beta$ active site (Ser-465) than the bulkier diacyl phospholipid substrate in the presence of Ca$^{2+}$-bound CaM. Remarkably, native iPLA$_2\beta$ is selectively and stoichiometrically autoacylated by unsaturated acyl-CoAs (particularly oleoyl-CoA), but not saturated acyl-CoAs, present in a phospholipid bilayer. Conversely, autoacylation of iPLA$_2\beta$ by saturated acyl-CoAs is dramatically increased by either mutagenesis of Ser-465 or pretreatment of the enzyme with BEL. In contrast to its inability to inhibit acyl-CoA hydrolysis, calmodulin in the presence of calcium blocked covalent acylation of iPLA$_2\beta$ by oleoyl-CoA. A combination of partial trypsinolysis and MALDI-MS was utilized to localize the region of acylation to amino acid residues ≈400-600 (adjacent to the calmodulin binding domain) which includes the nucleotide and lipase consensus sequence motifs. Clearly, the site of acylation is distinct from the iPLA$_2\beta$ active site serine (Ser-465) and the proximal nucleophilic residue(s) which form(s) a covalent adduct with BEL. In conjunction, these results demonstrate the existence of a second nucleophilic site(s) in iPLA$_2\beta$ capable of cleaving the acyl-CoA thioester bond of both saturated and unsaturated molecular species of acyl-CoA resulting in the formation of a stable acyl-enzyme.

To our knowledge, we believe that iPLA$_2\beta$ is the only intracellular phospholipase $A_2$ to exhibit substantial amounts of long chain acyl-CoA thioesterase activity and represents the first acyl-CoA thioesterase identified at the molecular level shown to efficiently hydrolyze membrane-associated acyl-CoAs. In contrast, in vitro assays with purified recombinant cPLA$_2\gamma$ (98) and iPLA$_2\gamma$ (C. M. Jenkins and R. W. Gross, unpublished observation) in our hands did not detect appreciable long-chain acyl-CoA hydrolase activities. A 54 kDa acyl-CoA hydrolase from rat intestinal microsomes was found to cleave long chain acyl-CoAs in the presence of phosphatidylcholine vesicles, although the sequence identity of this enzyme has not been described since its original purification (99). Intriguingly, iPLA$_2\beta$ has been previously found to be localized to the mitochondrial inner membrane (90) and the plasma membrane (96). One possible role of iPLA$_2\beta$ may be to prevent an excess of palmitoyl-CoA accumulation at plasma membranes (e.g. the sarcolemma which rapidly imports fatty acids and converts them to their acyl-CoA derivatives) or at the mitochondrial inner membrane which, through CPT-1, transfers palmitoyl-CoA to the matrix via a palmitoyl-carnitine intermediate.

Furthermore, considerable work has underscored the importance of both fatty acid and acyl-CoA molecular species as modulators of ion channel function (100,101). Arachidonic acid, either added exogenously or generated in situ by phospholipase $A_2$, is believed to be an important regulator of ARC (102), Kv1.1 (103), Kv1.5 (104), IK1 (105), and epithelial Na+ (106) channels, among others. In addition, physiologically relevant concentrations of acyl-CoAs in patch clamp as well as whole cell studies have been shown to stimulate the activity of multiple different types of K channels presumably through direct interactions of the ion channel with the charged acyl-CoA moiety (100,101,107). Accordingly, cells (e.g. cardiac myocytes) must regulate ion channel function in the proximity of active fatty acid import in which nascent acyl-CoAs are either hydrolyzed by thioesterases (i.e. futile cycling) or transported out of the sarcolemma through the process of diffusion or through specific interactions with acyl-CoA binding proteins.

Considering the ability of iPLA$_2\beta$ to translocate to the plasma membrane in activated cells (96), modulate Kv1.1 electrophysiologic function (103), and precipitate ventricular arrythmias following ischemia (54), we discovered that iPLA$_2\beta$ may regulate ion channel function both by the release of arachidonic acid from phospholipids and modulation of the effective mole concentrations of palmitoyl-CoA and fatty acids (which increase dramatically during ischemia) surrounding sarcolemmal ion channels.

Depletion of intracellular calcium stores in smooth muscle cells has been previously demonstrated to activate iPLA$_2\beta$ through a mechanism hypothesized to involve the dissociation of CaM from the enzyme (46,62). Store operated calcium (cation) channels (SOCs) in the plasma membrane are then activated in response to agonist stimulated intracellular calcium pool depletion for the purpose of replenishing the emptied calcium stores. Recent work by Bolotina and colleagues has provided additional details into this process by showing that iPLA$_2\beta$ is required for activation of SOCs through generation of lysophospholipids (53). Furthermore, the inhibitory complex between CaM and iPLA$_2\beta$ could be disrupted by a partially purified preparation of calcium influx factor (CIF) (53). Although attempts to elucidate the molecular identity of CIF over the past 10 years have not been successful, these studies have determined various chemical properties of calcium influx factor.

In general, CIF is believed to be a non-protein, diffusible, phosphorylated "sugar nucleotide" of approximately 600 Da which is resistant to heat, alkaline pH, protease treatment, and is retained on a C18 reverse phase matrix (108). Although the molecular weight of oleoyl-CoA (1030 Da) and other fatty acyl-CoAs are slightly larger than that approximated for CIF, many of the other chemical characteristics of these compounds are similar. In this work, we demonstrate that oleoyl-CoA is able to mimic the properties of CIF by restoring the phospholipase A$_2$ activity of Ca$^{2+}$/CaM-inhibited iPLA$_2\beta$.

Although acyl-CoAs are considered to be ubiquitous cellular constituents, their acute production due to fatty acid influx and/or increases in acyl-CoA synthetase activity in specific membrane microenvironments proximal to complexes of Ca$^{2+}$/CaM-inhibited iPLA$_2\beta$ would likely be sufficient to mediate activation of iPLA$_2\beta$ through displacement of calmodulin in a temporal and spatially-specific manner. We specifically point out that many other CIF-like cellular constituents capable of reversing Ca$^{2+}$/CaM-iPLA$_2\beta$ inhibition may exist and that other membrane components and conditions which occur in vivo (proteins, membrane surface charge and curvature, membrane electrochemical potential, etc.) may facilitate this process.

The specificity of iPLA$_2\beta$-mediated acyl-CoA hydrolysis for saturated vs. unsaturated acyl-CoA molecular species (FIG. 2) and inverse selectivity for autoacylation (FIG. 5), provides intriguing evidence to suggest their potential functions in cellular lipid homeostasis. Recently, small interfering RNA knockdown of iPLA$_2\beta$ and mechanism-based inhibition of iPLA$_2\beta$ by BEL was demonstrated to inhibit the hormone induced differentiation of 3T3-L1 pre-adipocytes (50). Although the phospholipase A$_2$ activity of iPLA$_2\beta$ likely contributes to its importance in 3T3-L1 differentiation (through production of non-esterified fatty acids and lysophosphatidic acid), the acyl-CoA thioesterase activity of iPLA$_2\beta$ may also be important. For example, iPLA$_2\beta$ could facilitate futile cycling of excess saturated acyl-CoAs, thereby attenuating their inhibition of acetyl-CoA carboxylase and thereby promoting lipogenesis.

In addition, accelerated palm-CoA hydrolysis by iPLA$_2\beta$ could assist 3T3-L1 differentiation by relieving potential palmitoyl-CoA mediated inhibition of PPAR$\gamma$ (34). De novo synthesized monounsaturated fatty acyl-CoAs, produced through the action of stearoyl-CoA desaturases from their saturated precursors, is believed to directly contribute to the high content of monounsaturated fatty acids (primarily 18:1) in adipocyte triglycerides, phospholipids, and cholesterol esters (109). The resistance of oleoyl-CoA to hydrolysis by iPLA$_2\beta$ and the formation of a stable oleoylated enzyme suggest that iPLA$_2\beta$ may be an unsaturated acyl-CoA acyltransferase for as yet undiscovered protein or lipid acceptors.

Multiple acyl-CoA thioesterases have been cloned from mammalian sources and are classified on the basis of their subcellular localization (cytosolic, mitochondrial, or peroxisomal), sequence similarity, and ability to be induced by peroxisome proliferators. The majority of these thioesterases, as well as all known intracellular phospholipases A$_2$, contain the canonical lipase (esterase) consensus sequence motif G-X-S-X-G. Amino acid sequence alignments of iPLA$_2\beta$ with the known mammalian acyl-CoA thioesterases did not reveal any significant sequence homology outside of the G-X-S-X-G consensus motif. This is not completely unexpected given the diversity among the different classes of acyl-CoA thioesterases. Some of the established acyl-CoA thioesterase family members (e.g. MTE-I and CTE-I) possess conserved putative nucleotide binding sequences (G-X-G-X-X-G), however it is currently unknown whether these putative nucleotide binding motifs interact with the CoA nucleotide. Interestingly, calcium-independent phospholipase A$_2\beta$ displays an acyl-CoA substrate selectivity (C14-C20) similar to the cytosolic Type-I thioesterase (CTE-I) (38). In addition, iPLA$_2\beta$, like CTE-I, is not inhibited by high concentrations of CoASH, indicating that these enzymes are probably not involved in "sensing" and regeneration of free CoASH through acyl-CoA hydrolysis as has been ascribed to peroxisomal acyl-CoA thioesterase-2 (70). Calcium-independent phospholipase A$_2\beta$ and other acyl-CoA thioesterases likely serve both metabolic and signaling functions. While the importance of fatty acid synthesis and α/β-oxidation of fatty acids (acyl-CoA-dependent processes) are evident, the metabolic role of the multiple cellular fatty acyl-CoA thioesterase activities in normal and disease states remain to be elucidated.

Covalent fatty acid acylation of eukaryotic proteins has been previously demonstrated to occur either through N-myristoylation, N-palmitoylation, or S-palmitoylation (110-112). Intriguingly, although numerous investigators have described protein palmitoylation utilizing palmitoyl-CoA, iPLA$_2\beta$ represents the first example to our knowledge of an enzyme which is selectively acylated by oleoyl-CoA and arachidonyl-CoA (but not by palmitoyl-CoA). The 54 kDa acyl-CoA hydrolase from rat intestinal microsomes has been shown to be covalently modified by oleoyl-CoA, likely through a thioester linkage, although the susceptibility of this enzyme to acylation by other fatty acyl CoAs was not examined (99). It would appear that this acyl-CoA hydrolase is unrelated to iPLA$_2\beta$ since it did not exhibit detectable phospholipase or lysophospholipase activity (99).

We demonstrated our discovery that purified recombinant iPLA$_2\beta$ possesses robust palmitoyl-CoA hydrolase activity in addition to its previously well-characterized lysophospholipase and phospholipase A$_2$ activities. Thus, iPLA$_2\beta$ could potentially have multiple effects on the production of lipid metabolites (arachidonic acid and lysolipids), or alternatively through removal of saturated acyl-CoAs from cellular membranes, and regulate their metabolic fate. Importantly, calcium-independent phospholipase $A_2\beta$ is present in multiple subcellular compartments, most notably cytosol, mitochondria, and nuclear membranes (84,90,96). The presence of $iPLA_2\beta$ in mitochondria suggests that it may serve a similar function to the mitochondrial acyl-CoA thioesterase which has been proposed to be involved in UCP regulation. Moreover, $iPLA_2\beta$ is autoacylated in a highly substrate-specific fashion (by oleoyl- but not palmitoyl-CoA) which occurs at a second active site distinct from the hydrolytic lipase site (GXSXG). Collectively, these results identify a complex interplay of enzymatic, biophysical, and covalent modifications that likely contribute to the multiple diverse signaling roles of $iPLA_2\beta$ activity in cellular functions. Multiple discrete chemical mechanisms (covalent and non-covalent) likely regulate $iPLA_2\beta$ activity, determine $iPLA_2\beta$ subcellular localization, and contribute to the previously unappreciated biologic complexity of this critical signaling enzyme.

TABLE 1

25 kDa $iPLA_2\beta$ Fragment Tryptic Peptides Identified by MALDI-MS Analysis

| m/z (Obs.) | m/z (Calc.) | Mod. | Sequence | Residues |
|---|---|---|---|---|
| 1076.6085 | 1076.5376 |  | (R)NYDAPEVIR(E) (SEQ ID NO: 7) | 547-555 |
| 1093.6473 | 1093.5795 | pyroGlu | (R)QPAELHLFR(N) (SEQ ID NO: 8) | 538-546 |
| 1110.6732 | 1110.6060 |  | (R)QPAELHLFR(N) (SEQ ID NO: 8) | 538-546 |
| 1149.7157 | 1149.6454 |  | (R)KPAFILSSMR(D) (SEQ ID NO: 9) | 408-417 |
| 1458.8209 | 1458.7341 |  | (R)NYDAPEVIREPR(F) (SEQ ID NO: 10) | 547-558 |
| 1708.9492 | 1708.8546 |  | (R)GSRPYESGPLEEFLK(R) (SEQ ID NO: 11) | 497-511 |
| 2184.2805 | 2184.1599 |  | (K)VMLTGTLSDRQPAELHLFR(N) (SEQ ID NO: 12) | 528-546 |
| 2379.3950 | 2379.2573 |  | (R)FNQNINLKPPTQPADQLVWR(A) (SEQ ID NO: 13) | 559-578 |

TABLE 2

Cardiolipin and Phospholipid Hydrolysis Catalyzed by $iPLA_2\beta$ and $iPLA_2\gamma$ and Inhibition by BEL. Purified calcium-independent phospholipase $A_2\beta$ ($iPLA_2\beta$) or calcium-independent phospholipase $A_2\gamma$ ($iPLA_2\gamma$) were incubated with PAPC (100 µM) vesicles containing 10 mol % tetra-18:1 cardiolipin (CL) for 20 min at 37° C. Following addition of internal standards, lipids were extracted utilizing a modified Bligh-Dyer method prior to infusion and lipid analysis as described in Experimental Procedures.

| Lipid Species | nmol/reaction | | | | |
|---|---|---|---|---|---|
|  | Blank (−Ctl) | $iPLA_2b$ | $iPLA_2b$ + BEL | $iPLA_2g$ | $iPLA_2g$ + BEL |
| Tetra-18:1 CL | 2.04 | 0.29 | 1.95 | 1.85 | 2.18 |
| Tri-18:1 LysoCL | 0.06 | 0.03 | 0.10 | 0.19 | 0.14 |
| Di-18:1 LysoCL | 0.06 | 0.06 | 0.15 | 0.21 | 0.12 |
| 18:1 FA | 0.20 | 6.32 | 0.61 | 1.07 | 0.54 |
| 16:0 FA | 0.35 | 13.72 | 0.96 | 4.99 | 3.07 |
| 20:4 FA | 0.15 | 8.53 | 0.50 | 0.94 | 0.54 |

TABLE 3

Cardiolipin and Phospholipid Hydrolysis Catalyzed by $iPLA_2\beta$. Vesicles (100 µM total lipid) containing PLPC (60 mol %), plasmenyl-PE (30 mol %), and tetra-18:1 cardiolipin (10 mol %) were incubated with purified $iPLA_2\beta$ for the indicated times at 37° C. Following addition of internal standards, lipids were extracted utilizing a modified Bligh-Dyer method prior to infusion and lipid analysis as described in Experimental Procedures.

| Lipid Species | nmol/reaction | | |
|---|---|---|---|
|  | 0 min | 1 min | 5 min |
| PLPC | 30.22 | 29.45 | 29.22 |
| 16:0 LPC | 0.00 | 1.37 | 1.86 |
| 18:2 LPC | 0.00 | 0.65 | 0.95 |
| 16:0 FA | 0.00 | 0.65 | 1.30 |
| 18:2 FA | 0.00 | 1.67 | 2.51 |
| Plasm-PE | 14.29 | 13.80 | 12.28 |
| LPE | 0.00 | 0.68 | 0.91 |
| 20:4 FA | 0.00 | 0.72 | 1.13 |

TABLE 3-continued

Cardiolipin and Phospholipid Hydrolysis Catalyzed by $iPLA_2\beta$. Vesicles (100 µM total lipid) containing PLPC (60 mol %), plasmenyl-PE (30 mol %), and tetra-18:1 cardiolipin (10 mol %) were incubated with purified $iPLA_2\beta$ for the indicated times at 37° C. Following addition of internal standards, lipids were extracted utilizing a modified Bligh-Dyer method prior to infusion and lipid analysis as described in Experimental Procedures.

| Lipid Species | nmol/reaction | | |
|---|---|---|---|
|  | 0 min | 1 min | 5 min |
| Tetra 18:1-CL | 6.06 | 5.96 | 5.84 |
| Tri-18:1 LysoCL | 0.00 | 0.03 | 0.05 |
| 18:1 FA | 0.00 | 0.60 | 0.90 |

Cardiolipin Hydrolysis

Purified calcium-independent phospholipase $A_2$ ($iPLA_2\beta$) and calcium-independent phospholipase $A_2\gamma$ were incubated with vesicles containing 10% cardiolipin (tetra 18:1) for 20 min at 37° C. For some samples, BEL was added at 10 µM final concentration. Following addition of internal standards, lipids were extracted into chloroform/methanol (modified Bligh-Dyer method) as previously described (10.1) in the presence of internal standards (14:1-14:1-PC (15 nmol/rxn), tetra 14:0-CL (2 nmol/rxn), and 16:0 d4 FA (5 nmol/rxn). Lipids from each sample were extracted twice against 50 mM LiCl, back-extracted once against 10 mM LiCl, dried under $N_2$, and stored at −20° C. Samples were dissolved in 100 μl 1 of 1:1 (v/v) chloroform/methanol and diluted 20-fold immediately prior to infusion and lipid analysis.

```
SEQUENCE
Human Oleoyl-iPLA₂β
SEQUENCE NO. 1
[MQFFGRLVNTFSGVTNLFSNPFRVKEVAVADYTSSDRVREEGQLILFQN

TPNRTWDCVLVNPRDSQSGFRLFQLELEADALVNFHQYSSQLLPFYESSP

QVLHTEVLQHLTDLIRNHPSWSVAHLAVELGIRECFHHSRIISCANCAEN

EEGCTPLHLACRKGDGEILVELVQYCHTQMDVTDYKGETVFHYAVQGDNS

QVLQLLGRNAVAGLNQVNNQGLTPLHLACQLGKQEMVRVLLLCNARCNIM

GPNGYPIHSAMKFSQKGCAEMIISMDSSQIHSKDPRYGASPLHWAKNAEM

ARMLLKRGCNVNSTSSAGNTALHVAVMRNRFDCAIVLLTHGANADARGEH

GNTPLHLAMSKDNVEMIKALIVFGAEVDTPNDFGETPTFLASKIGRQLQD

LMHISRARKPAFILGSMRDEKRTHDHLLCLDGGGVKGLIIIQLLIAIEKA

SGVATKDLFDWVAGTSTGGILALAILHSKSMAYMRGMYFRMKDEVFRGSR

PYESGPLEEFLKREFGEHTKMTDVRKPKVMLTGTLSDRQPAELHLFRNYD

APETVREPRFNQNVNLRPPAQPSDQLVWRAARSSGAAPTYFRPNGRFLDG

GLLANNPTLDAMTEIHEYNQDLIRKGQANKVKKLSIVVSLGTGRSPQVPV

TCVDVFRPSNPWELAKTVFGAKELGKMVVDCCTDPDGRAVDRARAWCEMV

GIQYFRLNPQLGTDIMLDEVSDTVLVNALWETEVYIYEHREEFQKLIQLL

LSP]-CO(CH₂)₇CHCH(CH₂)₇CH₃*
*Oleoylation at any iPLA₂β residue
```

Shotgun lipidomics: multidimensional MS analysis of cellular lipidomes The technical article SHOTGUN LIPIDOMICS: ELECTROSPRAY IONIZATION MASS SPECTROMETRIC ANALYSIS AND QUANTITATIN OF CELLULAR LIPIDOMES DIRECTLY FROM CRUDE EXTRACTS OF BIOLOGICAL SAMPLES, Zianlin Han and Richard W. Gross, Washington University School of Medicine, St. Louis Mo., Mass Spectrometry Reviews, 2005, 24, 367-412 is incorporated herein in its entirety by reference. This article illustrates shotgun lipidomics.

Shotgun lipidomics comprises intrasource separation, multidimensional mass spectrometry and computer-assisted array analysis and is an emerging powerful technique in lipidomics. Through effective intrasource separation of predetermined groups of lipid classes based on their intrinsic electrical propensities, analyses of lipids from crude extracts of biologic samples can be directly and routinely performed. Appropriate multidimensional array analysis of lipid pseudomolecular ions and fragments can be performed leading to the identification and quantitation of targeted lipid molecular species. Since most biologic lipids are linear combinations of aliphatic chains, backbones and head groups, a rich repertoire of multiple lipid building blocks present in discrete combinations represent experimental observables that can be computer reconstructed in conjunction with their pseudomolecular ions to directly determine the lipid molecular structures from a lipid extract. Through this approach, dramatic increases in the accessible dynamic range for ratiometric quantitation and discrimination of isobaric molecular species can be achieved without any prior column chromatography and operator-dependent supervision. At its current gate of development, shotgun lipidomics can analyze over 20 lipid classes, hundreds of lipid molecular species and more than 95% of the mass content of a cellular lipidome. Thus, understanding the biochemical mechanisms underlying lipid-mediated disease states will be greatly facilitated by the power of shotgun lipidomics.

Expert Rev Proteomics 2(2), 253-264 (2005)

Lipidomics, the metabolomics of lipids, is a rapidly expanding field following the tremendous progress that has been made in genomics and proteomics [1.1, 2.1]. As such, lipidomics is an essential component of systems biology [3.1, 4.1]. Specifically, lipidomics is the large-scale study of organic solvent-soluble lipids by integrating many different modern techniques (e.g., mass spectrometry [MS]). The first essential step in lipidomics is to determine a total lipid profile (i.e., lipidome). The total lipid profile reflects the functional status of the cellular metabolic history and the lipid-related protein expression and functional profile of the cell resulting from metabolic, environmental or nutritional clues [5.1, 6.1]. The lipidome provides information on the biophysical state of cellular membranes [5.1], differences in lipid pools and turnover rates by dynamic lipidomics) [7.1-10.1], alterations in cellular energy supply [6.1], and lipid second messenger levels reflecting cellular metabolic responses and transcriptional programs [11.1]. The field of lipidomics has been greatly advanced by the development and application of MS, particularly electrospray ionization (ESI)/MS [1.1, 12.1-15.1]. Investigations in lipidomics are currently focused on identifying alterations in cellular and/or body fluid lipid levels indicative of pathology (e.g., the onset and progression of disease), environmental perturbations (e.g., diet, toxins or drugs), or response to treatment. Therefore, lipidomics is directly related to drug discovery and evaluation of drug efficacy in addition to its fundamental role in identifying the biochemical mechanisms of lipid metabolism and the discovery of novel biomarkers.

Cellular lipidomes are highly complex and variable, depending upon the species, cell type, internal organelles, micro-domains (e.g., rafts) and growth conditions. Furthermore, each cell type possesses different mole percentages of specific lipid classes, subclasses and molecular species (that are comprised of the differential lengths, degree of unsaturation and branching of aliphatic chains). Tens of thousands of possible lipid molecular species are predictably present in a cellular lipidome at the level of attomole to nanomole of lipids per milligram of protein. Studies in lipidomics by many investigators have focused on either one class/subclass of lipids or one of the physical/chemical properties of lipids [16.1-24.1], which is now referred to as targeted lipidomics. However, the emergence of Intrasource separation with multidimensional MS has allowed global lipid profiling and quantitation directly from crude extracts of biologic samples [1.1, 6.1, 9.1, 15.1, 25.1-27.1]. These methods have now been referred to as shotgun lipidomics, which was developed to exploit the synergy between the uses of intrasource separation and multidimensional MS.

Shotgun Lipidomics: Intrasource Separation

An essential point of ESI is the charge separation and selective ionization that separated charges undergo at a high electrical potential (typically ~4 kV) in the ion source [32.1-35.1]. Specifically, an electrospray ion source selectively generates gas-phase cations in the positive-ion mode and results in anions in the negative-ion mode if both inherently charged moieties are present in the infused solution. If the analytes in the infused solution do not carry net inherent charge(s), these compounds can interact with small cation(s) or anion(s) available in the matrix to yield adduct ions in positive- or negative-ionmode (i.e., in conjunction with the imposed field), respectively. The ionization efficiencies of these electrically neutral compounds depend on the inherent dipoles of the compounds. The authors recognized this physical process in the electrospray ion source in their earliest study and used it to resolve lipid classes in a crude lipid extract into different categories based on the intrinsic electrical properties of each lipid class (see [1.1, 15.1] for reviews) [36.1]. With regard to the separation of lipid classes, this technique is analogous to using ion-exchange chromatography for separation of lipid classes (as the authors have previously employed [37.1]). However, this approach is rapid, direct, reproducible and avoids artifacts inherent in chromatography-based systems [38.1]. This new methodology has now been referred to as intrasource separation [15.1, 26.1].

Although there are tens of thousands of potential lipid molecular species present in a cellular lipidome, these species can generally be classified into three main categories based upon their electrical properties [15.1]. The lipid classes in the first category are those carrying at least one net negative charge under weakly acidic conditions and are therefore referred to as anionic lipids, which can be directly analyzed from diluted lipid extracts by negative-ion ESI/MS. Lipid classes in this category include cardiolipin, phosphatidylglycerol, phosphatidylinositol and its polyphosphate derivatives, phosphatidylserine, phosphatidic acid, sulfatide, acyl-CoA and anionic lysophospholipids. The lipid classes in the second category are those that are electrically neutral under weakly acidic conditions, but become negatively charged under alkaline conditions. Therefore, they are referred to as weakly anionic lipids and can be analyzed in negative-ion ESI/MS after addition of a small amount of LiOH (or other suitable bases). Ethanolamine glycerophospholipid (PE), lysoPE, nonesterified fatty acids and their derivatives, bile acids and ceramide are some examples in this category. The remaining lipid classes belong to the third category, which includes choline glycerophospholipid (PC), lysoPC, sphingomyelin, cerebroside, acylcarnitine, diacylglycerol, triacylglycerol, cholesterol and its esters. All of these lipid classes in the third category can be analyzed in positive-ion ESI/MS after addition of a small amount of LiOH to the Infused solution as lipids in the first and second categories are now anionic under these conditions. It should be pointed out that the authors generally assess the content of cholesterol and its esters in lipid extracts by employing a simple fluorometric method [39.1, 40.1]. Individual molecular species of cholesterol esters can be profiled by precursor-ion analysis as previously described [41.1]. Alternatively, a method to quantitate cholesterol and its derivatives by ESI tandem MS (MS/MS) after a simple one-step chemical derivatization of cholesterol to cholesterol-3-sulfate by a sulfur trioxide-pyridine complex may be employed [42.1].

Through these methods, a comprehensive series of mass spectra with respect to each of the aforementioned conditions can be obtained for each category of lipids. Each ion peak in each of these mass spectra represents at least one lipid molecular species. This set of three multiplexed truss spectra effectively replace high-performance liquid chromatography (HPLC) column separation by exploiting intrasource separation. Of course, each pseudomolecular ion peak in each mass spectrum may contain nominal isobaric species resulting from either members of the same lipid class or from other class(es) in the category. Although product ion PSI/MS analyses can be performed to identify the molecular species underneath each ion peak at this stage (as the authors routinely conducted previously [15.1]), It is labor Intensive and the results of product ion analysis may be affected by the presence of neighboring peaks. More effective and accurate deconvolution of isobaric species can be accomplished through multidimensional MS with appropriate array analysis.

Shotgun Lipidomics: Multidimensional MS

The inventors recognize that most classes of lipids in a cellular lipidome are multiple discrete covalent assemblies of a lipid backbone (typically glycerol) with linear combinations of various aliphatic chains (typically 14-22 carbons long containing variable degrees of unsaturation) with (or without) a wide variety of polar head groups (e.g., choline, ethanolamine, serine and inositol). Therefore, if one could effectively and unambiguously identify the presence of each building block of polar head groups and aliphatic chains (and combinations thereof) in each pseudomolecular ion, the complexities in the lipidome could be deconvoluted and readily solved. The techniques of neutral loss and precursor-ion scanning each exploits at least one of the structural characters of these building blocks to provide the tools to efficiently profile each ion peak after army construction, and deconvolution to identify the building blocks present and identify the moieties from which they were derived. Following this concept, a new technique, referred to as multidimensional MS, has recently been developed [1.1, 9.1, 15.1, 25.1-27.1].

A coordinated series of sequential 2D mass spectra are the basic components of multidimensional MS. In the first dimension, each 2D mass spectrum contains the primary (molecular or pseudomolecular) ions in the x axis of mass-to-charge ratio (m/z) while the second dimension, in most cases, is comprised of the individual building blocks (i.e., polar head groups and/or aliphatic chains) of lipids (which are characterized by either neutral loss scanning or precursor-ion scanning or both) in an axis of mass (in the rare of neutral loss scanning) or m/z (in the case of precursor-ion scanning). One feature of a 2D mass spectrum is that each imaginary mass spectrum along a vertical line through each m/z of the primary ion represents a pseudo product ion mass spectrum of a precursor ion at the primary ion mass spectrum crossed with the broken line. This series of arrayed spectra is entirely analogous to a 2D-NMR spectroscopy where axes are comprised of distinct frequency domains.

Each 2D-ESI mass spectrum predictably varies with different:
Infused solution conditions (e.g., lipid concentration, acidic/alkaline condition and solvent polarity, which can be readily achieved by installation of a mixer in the front of a spray capillary tube and can be controlled by operational software)
Ionization conditions (e.g., source temperature and spray voltage)
Fragmentation conditions (e.g., collision gas pressure, collision energy, collision gas and MS/MS scanning modes/settings)

These points aid in the identification, quantitation and study of lipids. Each of these variables facilitates the construction of additional dimensions that can be built upon each 2D mass spectrum foundation, which collectively constitutes a new level of information directly obtainable from lipid mass spectrometric analysis (i.e., multidimensional MS). Specifically, multidimensional MS is defined as the aggregate of mass spectrometric analyses conducted under a variety of instrumental variables that collectively comprise an n-dimensional spectrum. Each of these variables forms one dimension of the multidimensional mass spectrum from which a 2D mass spectrum can be constructed for ease of use and display.

2D mass spectrometric analysis for the identification of lipid building blocks is different from MS/MS analysis, although a 2D mass spectrum for building block analysis includes of a collection of MS/MS spectra from neutral loss and/or precursorion scanning of numerous precursor ions in its arrayed format. The 2D mass spectrum for building block analysis exploits array analysis techniques integrating both the primary ion mass spectrum and associated neutral loss/precursorion spectra to determine molecular composition and amount of a lipid constituent from a single automated platform. As previously mentioned, one very important feature of a 2D mass spectrum is the presence of pseudo product-ion mass spectra for each pseudomolecular ion in the primary ion mass spectrum. Therefore, many of the characteristics of product-ion analysis can be extracted from the 2D mass spectrometric analysis. Regiospecific identification of each individual molecular species [43.1] and quantitative analysis of isobaric species are two important features of product-ion analyses (among others) that can be readily achieved in 2D-MS analysis [9.1, 26.1]. Another very important feature of a 2D mass spectrum is the increase of dynamic range relative to a selected internal standard. Therefore, quantitation and refinement of low-abundance molecular species with a selected internal standard for each lipid class can also be readily achieved by 2D [26.1, 27.1], but not by MS/MS analyses where a set of internal standards must be employed [44.1-47.1]. Most Importantly, identification and quantitation of each individual molecular species by multidimensional MS can be automated, and thus multidimensional MS analysis of lipids represents a high-throughput platform for global studies of the cellular lipidome.

Shotgun Lipidomics: Quantitation of Individual Molecular Species

Accurate quantitation of each individual molecular species can be achieved by multidimensional MS through a two-stage ratiometric process [26.1, 27.1]. First, the abundant molecular species in a class are quantitated by comparison with a preselected internal standard for the lipid class in the 1D (primary ion) mass spectrum. Next, these quantified values are used as endogenous internal standards in combination with the original exogenous internal standard for ratiometric comparisons. This is performed to quantitate or reline the mass content of low-abundance individual molecular species from at least one representative MS/MS scan for the class of interest in the 2D-MS for building block analyses.

The key advantage in this two-stage process is the increase of dynamic range. There are many different measures of dynamic range that it affords. For example, the dynamic range of concentration in which the quantitative technique is linear. This is the most commonly accepted meaning of the concept for dynamic mange in the literature. The authors have demonstrated this measure of dynamic mange in the low lipid concentration range in many of their studies [25.1, 36.1, 48.1, 49.1]. Another measure of dynamic range is the relative ratio of internal standard versus individual molecular species of interest. A 100-fold dynamic range (from 0.1 to 10 of the ratio) can generally be achieved. However, this dynamic range can suffer by the presence of background noise (i.e., chemical noise) and baseline drift (i.e., instrumental stability) in some cases. Therefore, under adverse experimental conditions, low-abundance molecular species can only be approximated (or not quantitated at all) and require 2D analyses. Through MS/MS in a 2D-MS format, a 400-fold (even up to 1000-fold as long as the concentration measures of dynamic range are linear over 1000-fold in comparison with controls) increase can be obtained. The authors find that this dynamic range can be achieved in almost all cases since background noise is dramatically reduced and different intensity peaks of the sane class can be found in the primary ion spectra to serve as ratiometric makers for the quantitation of low-abundant molecular species. However, the authors specifically point out that these conditions must be validated and that additional internal standards ray need to be employed in rare cases.

The main advantage of this approach for the quantitation of individual lipid molecular species in each lipid class is its simplicity in comparison with the quantitation of lipid species by MS/MS (in which multiple internal standards for each lipid class must be selected to eliminate the effects of acyl chain length, degrees of saturation and double bond locations on the kinetics of pseudomolecular ion fragmentation [44.1, 45.1, 50.1, 51.1]). The authors have demonstrated that the response factors of individual molecular species in most of the polar lipid classes rarely depend on the physical properties of aliphatic chains in biologic samples, but rather on the electrical properties of the polar head groups (i.e., dipole moments) under conditions that utilize low concentrations of lipids (<10 pmol/µl) so that aggregates do not form in 1:1 $CHCl_3/MeOH$ (36.1,48.1,52.1). In all cases, corrections for any differences in $^{13}C$ isotopomer peak intensities must be made for accurate results [15.1,25.1]. In this study, the authors further examined the response factors of 11 PC molecular species that possess different aliphatic chains in equimolar mixtures of 1 pmol/µl or less (each) and found that the response factors of these PC species were essentially identical within experimental error after correction for different $^{13}C$ isotopomer distribution. These results demonstrate that individual molecular species of a polar lipid class can be quantitated using one internal standard for the class. Somerharju and colleagues independently examined the effects of acyl chain length, unsaturation and lipid concentration on the response factors of instruments and found that the response factors were similar within experimental errors in the low lipid concentration region, supporting the authors' previous observations [53.1]. Furthermore, if their data were corrected to account for the different $^{13}C$ isotopomer distributions, the response factors of molecular species containing different acyl chain lengths would then yield virtually identical results to those previously described [25.1, 49.1]. Thus, the response factors of individual molecular species in a polar lipid class rarely depend on the physical properties of acyl chains in the low concentration range as determined in independent laboratories.

A set of endogenous internal standards from a given class in addition to the original external standard are generally well distributed in biologic samples regarding different aliphatic chain lengths and degrees of unsaturation. Therefore, these endogenous standards represent superior standards to human-selected internal standards for lipid quantitation by MS/MS where the overlap of added internal standard ions with endogenous molecular ions must be considered, thereby limiting the candidates that can be selected for exogenous internal standards. One weakness present in 2D-MS analysis of lipids to quantitate and/or refine low-abundance molecular species is that the endogenous set of standards are secondary to the original internal standard and thus the experimental errors of the mass content of these low-abundance molecular species are amplified. However, the total mass content of these low-abundance molecular species typically only account for less than 5 mol % of the entire mass of the class. Therefore, the amplified experimental error for the mass content of these low-abundance species will not substantially affect the accuracy of quantitation for the entire class of lipids. The authors would also like to point out that the peaks composed of multiple isobaric molecular species should not be selected as an endogenous internal standard to minimize the effects of differential fragmentation on quantitation as previously discussed [15].

Utilities

The first application of shotgun lipidomics after intrasource separation and multidimensional MS was the quantitation and fingerprinting of triacylglycerol (TAG) molecular species directly from a crude lipid extract of a biologic sample [25.1]. Since there is no polar head group present in TAG molecular species, the second dimension of a 2D mass spectrum for TAG analysis represents the building blocks of TAG aliphatic chains that can readily be identified by neutral loss scanning of all naturally occurring fatty acids from lithiated or sodiated TAG molecular ions as previously described [25.1, 54.1-56.1]. One important feature of this methodology for TAG analysis is the ease in identifying individual isobaric TAG molecular species due to the abundance of multiple TAG molecular species present at each m/z value in lipid extracts of biologic samples. To date, this methodology represents the most sensitive, accurate and efficient technique for individual TAG molecular species analysis. This method has been extensively used in biologic, pathologic and pathophysiologic studies in the last 3 years (e.g., [9.1, 11.1, 26.1, 57.1-60.1). It should be emphasized that the location of double bonds in the constituent acyl chains is not identified by this method. However, if that is desirable, the regiospecificity of acyl chains in TAG species maybe identified in multidimensional MS by varying collision energy.

Recently, multidimensional ESI/MS has been used to identify the critical role of peroxisomal processing of fatty acids in adipocyte lipid storage and metabolism [9.1]. 2D-ESI/MS analyses demonstrated the accumulation of old chain length unbranched fatty acids in all major lipid classes in 3T3-L1 differentiating adipocytes, indicating the rapid α-oxidation of unbranched fatty acids. Further studies identifying the double bond location in odd chain length unbranched fatty acids found the exclusive presence of Δ9 olefinic species, suggesting the presence of two critical processes in fatty acid handling in adipocyte lipid storage and metabolism. First, monounsaturated fatty acids (e.g., oleic and palmitoleic acids) are not subject to α-oxidation, resulting in the absence of Δ8 unsaturated odd chain length fatty acids. Second, α-oxidation of saturated fatty acid substrate obeys the obligatory sequential ordering of α-oxidation prior to Δ9 desaturation [9.1].

Very recently, 2D-MS analysis has been exploited to investigate the energy mobilization in modest caloric restriction in mice and the mobilization of lipids in this process. Remarkably, only brief periods of fasting (4 and 12 h) result in multiple specific changes in the murine myocardial lipidome [6.1]. Specifically, substantial and specific depletion of PC and PE species containing polyunsaturated acyl chains occurred in murine myocardial, accounting for a total decrease of 39 nmol/mg protein in these pools after 12 h fasting and representing approximately 25% of total phospholipid mass and approximately 20 cal of Gibbs free energy/g wet weight of tissue. Furthermore, other myocardial phospholipid pods such as phosphatidylserine and phosphatidylinositol were not altered after fasting. No decrease in TAG mass was observed in myocardium during fasting; however, during 12 h of refeeding, myocardial TAG increased nearly threefold and returned to baseline levels after 24 h of refeeding. In contrast to the lipid alterations in myocardium, no changes in phospholipid mass were present in skeletal muscle and a dramatic decrease in skeletal muscle (or skeletal muscle associated) TAG mass was prominent after 12 h of fasting. These results identify phospholipids as a rapidly mobilizable energy source during modest caloric deprivation in murine myocardium while TAGs are a major source of energy reserves in skeletal muscle.

Summary

Shotgun lipidomics, based on intrasource separation, multidimensional MS and array analysis, has recently emerged as a powerful technique in the direct analysis of global cellular lipidomes. Intrasource separation can largely replace ion-exchange chromatography steps, allowing resolution of lipid classes based on the electrical properties of individual lipid classes. Multidimensional MS analysis facilitates an efficient identification of each subsequent individual molecular ion peak including potential nominal isobaric molecular species as well as the polar head groups, acyl moieties and the regiospecificity of each molecular species. The two-step quantitation process in 2D-MS for the analysis of building blocks provides an expanded dynamic range relative to a selected internal standard for each lipid class and represents an efficient and accurate method to quantify individual lipid molecular species. At the current stage of shotgun lipidomics, the analyses of over 20 lipid classes, hundreds of lipid molecular species and greater than 95% of the mass content of a cellular lipidome can be readily achieved. Its broad applications in biologic, pathologic and pathophysiologic studies have demonstrated the power and utility of shotgun lipidomics. It is anticipated that identification of many biochemical mechanisms underlying lipid metabolism critical to disease states will be uncovered through the use of shotgun lipidomics.

One key step to successfully perform shotgun lipidomics is the preparation of the sample. Commonly, crude lipid extracts are prepared by the Folch method [61.1] or the modified method of Bligh and Dyer [62.1]. Small residual aqueous phase contaminants in the extracts is inevitable, and thus back extraction or multiple extractions against an aqueous phase with a low salt concentration should be used to remove aqueous-soluable contaminants that adversely effect spectral quality. Correct pH and ionic strength conditions must be employed during sample preparation since acidic conditions in the aqueous phase can improve the extraction efficiency for acidic lipids (e.g., PtdH and acyl CoA) while destroying others (note that vinyl ether-containing compounds [i.e., plasmalogens] are acid labile). in addition, acidic/alkaline conditions must be strictly maintained to facilitate the selectivity of intrasource separation. The authors have found that lipid extraction against a low concentration LiCl solution (a weakly acidic condition) represents a suitable condition for extracts of most tissues, fluids and cells [15.1]. Since extraction recoveries of different lipid classes can vary, it is recommended to re-extract multiple times (at least twice) to afford a nearly complete extraction of all relevant lipids. The authors have found that the effects of differences in molecular species in a class on the extraction recoveries of these species are quite small. In addition, it is emphasized that the internal standard for each of the lipid classes should be added prior to lipid extractions for lipid analyses. Accordingly, the extraction recoveries of lipid classes are accounted for by comparisons with internal standards even if a complete extraction cannot be achieved.

Response factors of different molecular species in a class depend on the physical properties (i.e., length and saturation) of aliphatic chains to only a small degree after correction of isotopomer content when experiments are performed in the appropriate (low) concentration region [38.1, 53.1, 63.1]. The first consideration is the lipid concentration of the infused solution. Lipids, unlike other analytes, are unique in terms of their high hydrophobicity. When concentrations of lipids increase, they tend to aggregate to form micelles, even in some organic solvents [64.1]. It is well known that the longer the chain length and the higher the degrees of saturation of a lipid species, the lower the critical micellar concentration of the compound. Therefore, molecular species containing short acyl chains and/or polyunsaturation might show higher apparent response factors than those containing long and/or saturated acyl chains at a high lipid concentration if the lipid concentration exceeds approximately 10 pmol/μl [53.1, 63.1]. However, at low concentrations (<10 pmol/μl) in 1:1 (v/v) of chloroform/methanol, lipid-lipid interactions are rare and ionization efficiency of lipid mixtures largely depends on the electrical properties of each lipid molecular species, which is predominantly determined by the dipole in the polar head groups. Therefore, identical response factors for different molecular species in a class can be obtained and have been repeatedly and independently verified by multiple groups [36.1, 38.1, 53.1, 65.1]. However, when the concentration of lipids in the infusion solution increases to the point where lipid-lipid interactions become apparent, these response factors are no longer identical. Thus, concentration of lipids by straight or reversed phase chromatography must be performed with extreme caution since it promotes lipid-lipid interactions [38.1]. The maximal concentrations of lipids at which lipid-lipid interactions are small evidently depend on the solvent components used in the infusion solution. Therefore, a solvent system containing water, acetonitrile or a high percentage of methanol is not favored for global lipid analysis by shotgun lipidomics, although such a solvent system may be used for the analysis of a specific class of lipids by ESI/MS. The second crucial consideration is the different $^{13}$C isotopomer intensity distributions as described previously 15.1, 25.1, 49.1]. These effects could cause considerable differences between the apparent response factors of different molecular species and must be corrected in comparison with a selected internal standard as shown in. Alternatively these effects can be eliminated by determining the peak intensities after a deisotope calculation.

Caution should be exercised in employing ESI/MS/MS for quantitation of individual molecular species of each class of lipids, since the fragmentation patterns of each lipid molecular species depend on both the applied energy for collision-induced dissociation and on the structure of individual molecular species [25.1, 38.1, 43.1, 49.1, 66.1]. Changes in applied collision energy alter the kinetics of individual fragmentation pathways and result in changes in the distribution of the observed fragment ions. Thus, it is important to closely control fragmentation energies and to utilize both appropriate internal standards for each lipid class and molecular species as well as ratiometrically quantify each individual species so that identical physical parameters are compared.

Shotgun lipidomics is a rapidly evolving technology. The authors believe the techniques described herein will be extended to identify low-abundance concentration lipid classes through the integration of enrichment techniques (e.g., nano-HPLC) and the development of new MS/MS methods for the identification of these classes. Additionally, the development of instruments with greatly improved sensitivity and resolution will extend penetration into the low-abundance region of cellular lipidomes. To this end, enrichment approaches in conjunction with ESI Fourier transform ion cyclotron resonance MS holds much promise [13.1]. Second, high-efficiency direct-infusion techniques such as microfluidic approaches will be integrated into shotgun lipidomics to accommodate the need for high through put. Third, bioinformatics in lipidomics through database development and automation of data processing will play an essential role in the development and utility of shotgun lipidomics. Finally, it appears likely that affordable robust platforms for shotgun lipidomics will be made available to the biomedical research community for even routine clinical applications such as diagnosis and monitoring of drug therapy. The authors speculate that the large flux of quantitative lipidomics data integrated with genomic and proteomic studies will significantly enhance our understanding of the role of lipids in biologic systems. Advances in this field may also lead to enhanced diagnosis of lipid-related disease states at earlier time points to enhance therapeutic efficacy and tailor drug therapy in the next 5 years.

This work was supported by NIH grant PO1HL57278 and RO1HL41250 as well as the U.S. Neurosciences Education and Research Foundation.

In an aspect, the methods of the present disclosure are carried out by screening a library of compounds in an expression vector system (e.g., mammalian expression vector) and identifying compounds that alter the specific activity of the enzyme as assessed by shotgun lipidomics (or other techniques such as thin layer chromatography and scintillation spectrometry), or alter either the amount of the protein, or the structure of the protein as determined by 1D or 2D Western blot analysis or by mass spectrometry. Then determining if a compound has an effect on the ratio of the specific activity of the reaction of hydrolysis of AcylCoA or phosphatidylcholine. Alterations in the mass of the protein can be identified by Western blot analysis when a change in change in the molecular weight or the isoelectric point of the enzyme has occurred. Other methods known to those skilled in the art can be used in conjunction with the above approaches to identify altered binding characteristics, subcellular localization or covalent modifications. Such techniques include, but are not limited to mass spectrometric study of the protein either as an intact entity or through a bottom up mass spectrometric approach. The physiologic effects of such identified compounds can then be determined through comparisons of the effects of said agents in models of the above identified disease state to demonstrate the presence of physiologic benefit of said agent.

In one embodiment, a method is provided of altering the interaction of iPLA$_2$β with its endogenous calmodulin inhibitor through the actions of acyl-CoA or acyl-CoA like compounds that increase the inhibition of enzymic activity resulting in a decrease of iPLA$_2$β activity and a decrease in the production of lipid second messengers.

In one embodiment, a method is provided of altering the interaction of iPLA$_2$β with its endogenous calmodulin inhibitor through the actions of an acyl-CoA or acyl-CoA-like compound that decreases the inhibition of enzymic activity resulting in an increase of iPLA$_2$β activity and an increase in the production of lipid second messengers.

In one embodiment, a method is provided that identifies an exocyte in an iPLA$_2$β-calmodulin complex capable of modifying the interaction of iPLA$_2$β with calmodulin resulting in a change of enzymic activity.

In one embodiment, a means is provided to identify effective treatment modalities of calcium mediated or related disease processes that depend, either directly or indirectly, on the influence of capacitative calcium influx. These include, but are not limited to inflammation, heart attack, congestive heart failure and blood pressure.

In one embodiment, a method is provided for treating inflammation in living mammals. The method administering a compound that alters the interaction of iPLA$_2$β and its inhibitor and subsequently determining if that compound alters the inflammatory response.

In one embodiment, a method is provided for treating platelet thrombosis in living mammals. The method comprises administering a compound that alters the interaction of iPLA$_2$β and its inhibitor and subsequently determining if that compound alters platelet function.

In one embodiment a method is provided for screening a library of compounds to identify modulators of the iPLA$_2$β-calmodulin interaction by reconstitution of the enzyme modulator interaction and use of calcium entry fluorescence to screen for modulators of this interaction.

In one embodiment, a method is provided to screen natural product or combinatorial libraries by calcium sensitive dyes to identify modulators of the iPLA$_2$β-calmodulin interaction.

In one embodiment, a mechanism is provided to screen for compounds that alter the deleterious effects of congestive heart failure by promoting calcium uptake into the sarcoplasmic reticulum through modulating iPLA$_2$β activity and regulatory interactions.

In one embodiment, a mechanism is provided to modulate hormone or neurotransmitter release by intentionally altering capacitive calcium influx by modulation of iPLA$_2$β activity in a living mammal.

In one embodiment, a mechanism is provided to modulate the local concentrations of calcium by modulating iPLA$_2$β enzymic activity and subsequent capacitative calcium entry.

In one embodiment, a means is provided to attenuate arrhythmias or damage from a heart attack by modulating the calcium influx through regulation of iPLA$_2$β.

In one embodiment, a means is provided of identifying those living animals having disorders related to alteration of capacitative calcium influx by determining alterations in the iPLA$_2$β-calmodulin interaction.

In one embodiment, a method is provided of determining an inhibitor of iPLA$_2$β or iPLA$_2$γ. The method comprises obtaining an cardiolipin analysis by shotgun lipidomic technology on a living mammalian subject, determining the results of that analysis and determining the iPLA$_2$β or iPLA$_2$γ is inhibited when the cardiolipin content of the serum/biopsy sample is increased.

In one embodiment, a method is provided of treating a living mammal having diabetic cardiomyopathy which comprising administering an effective amount of an inhibitor to that subject, performing a shotgun lipidomics analysis on the subject and determining that the treatment was successful when and if serum or tissue biopsy cardiolipin levels are increased and/or lysocardiolipin levels are decreased.

In one embodiment, a pharmaceutical composition is provided that is effective to treat cardiomyopathy. The composition comprises a gene expressing a protein which synthesizes cardiolipin, increases the synthesis of cardiolipin, or is in a metabolic pathway of cardiolipin synthesis.

In one embodiment, a method is provided for treating diabetes in living mammals. The method comprises administering a gene, enzyme or pharmaceutical which decreases the concentration iPLA$_2$β and/or iPLA$_2$γ through transcriptional and/or translational regulation or effectively increases the inhibition of iPLA$_2$β through calmodulin or derivatives thereof.

In one embodiment, a method is provided of treating a living mammal having diabetic cardiomyopathy. The method comprising administering an effective amount of an inhibitor to that subject, performing a shotgun lipidomics analysis on the subject and determining that the treatment was successful when and if serum or tissue biopsy cardiolipin levels are increased and/or lysocardiolipin levels are decreased.

In one embodiment, a pharmaceutical composition is provided that is effective to treat cardiomyopathy. The composition comprises a gene capably expressing a protein which synthesizes cardiolipin, increases the synthesis of cardiolipin, or is in a metabolic pathway of cardiolipin synthesis.

In one embodiment, a method is provided for treating diabetes in living mammals. The method comprises administering a gene, enzyme or pharmaceutical which decreases the concentration iPLA$_2$β and/or iPLA$_2$γ through transcriptional and/or translational regulation or effectively increases the inhibition of iPLA$_2$β through calmodulin or derivatives thereof.

The article Global analyses of cellular lipidomes directly from crude extracts of biological samples by ESI mass spectrometry: a bridge to lipidomes, Xianlin Han, Richard W. Gross, Washington University in St. Louis, Lipid Research, Inc. is incorporated herein in its entirety by reference. Volume 44, 2003, used with permission.

This discovery is important to use an effective research tool because specific interactions are involved in almost any physiological process. If mankind is ever to cure diabetes and other debilitating diseases killing humans, thus mankind must have and use bedrock effective diagnostic and treatment tools.

REFERENCES

1. Kudo, I., and Murakami, M. (2002) Prostaglandins Other Lipid Mediat 68-69, 3-58
2. Scott, D. L., and Sigler, P. B. (1994) Adv Protein Chem 45, 53-88
3. Tischfield, J. A. (1997) J Biol Chem 272, 17247-17250
4. Leslie, C. C. (1997) J Biol Chem 272, 16709-16712
5. Underwood, K. W., Song, C., Kriz, R. W., Chang, X. J., Knopf, J. L., and Lin, L. L. (1998) J Biol Chem 273, 21926-21932
6. Pickard, R. T., Strifler, B. A., Kramer, R. M., and Sharp, J. D. (1999) J Biol Chem 274, 8823-8831
7. Chiba, H., Michibata, H., Wakimoto, K., Seishima, M., Kawasaki, S., Okubo, K., Mitsui, H., Torii, H., and Imai, Y. (2004) J Biol Chem 279, 12890-12897
8. Andrews, D. L., Beames, B., Summers, M. D., and Park, W. D. (1988) Biochem J 252, 199-206
9. Wolf, M. J., and Gross, R. W. (1996) J Biol Chem 271, 30879-30885
10. Tang, J., Kriz, R. W., Wolfman, N., Shaffer, M., Seehra, J., and Jones, S. S. (1997) J Biol Chem 272, 8567-8575
11. Mancuso, D. J., Jenkins, C. M., and Gross, R. W. (2000) J Biol Chem 275, 9937-9945
12. Schaffer, J. E., and Lodish, H. F. (1994) Cell 79, 427-436
13. Hall, A. M., Smith, A. J., and Bernlohr, D. A. (2003) J Biol Chem 278, 43008-43013
14. Marszalek, J. R., Kitidis, C., Dararutana, A., and Lodish, H. F. (2004) J Biol Chem 279, 23882-23891
15. Smith, S., Witkowski, A., and Joshi, A. K. (2003) Prog Lipid Res 42, 289-317
16. Moon, Y. A., and Horton, J. D. (2003) J Biol Chem 278, 7335-7343
17. Dircks, L., and Sul, H. S. (1999) Prog Lipid Res 38, 461-479
18. Coleman, R. A., and Lee, D. P. (2004) Prog Lipid Res 43, 134-176
19. Hiltunen, J. K., and Qin, Y. (2000) Biochim Biophys Acta 1484, 117-128
20. Eaton, S., Bartlett, K., and Pourfarzam, M. (1996) Biochem J 320 (Pt 2), 345-357

21. Mannaerts, G. P., Van Veldhoven, P. P., and Casteels, M. (2000) Cell Biochem Biophys 32 Spring, 73-87
22. Kakar, S. S., Huang, W. H., and Askari, A. (1987) J Biol Chem 262, 42-45
23. Branstrom, R., Leibiger, I. B., Leibiger, B., Corkey, B. E., Berggren, P. O., and Larsson, O. (1998) J Biol Chem 273, 31395-31400
24. Gribble, F. M., Proks, P., Corkey, B. E., and Ashcroft, F. M. (1998) J Biol Chem 273, 26383-26387
25. Glick, B. S., and Rothman, J. E. (1987) Nature 326, 309-312
26. Pfanner, N., Orci, L., Glick, B. S., Amherdt, M., Arden, S. R., Malhotra, V., and Rothman, J. E. (1989) Cell 59, 95-102
27. Ostermann, J., Orci, L., Tani, K., Amherdt, M., Ravazzola, M., Elazar, Z., and Rothman, J. E. (1993) Cell 75, 1015-1025
28. Fitzsimmons, T. J., McRoberts, J. A., Tachiki, K. H., and Pandol, S. J. (1997) J Biol Chem 272, 31435-31440
29. Knudsen, J., Jensen, M. V., Hansen, J. K., Faergeman, N. J., Neergaard, T. B., and Gaigg, B. (1999) Mol Cell Biochem 192, 95-103
30. Linder, M. E., and Deschenes, R. J. (2003) Biochemistry 42, 4311-4320
31. Hertz, R., Magenheim, J., Berman, I., and Bar-Tana, J. (1998) Nature 392, 512-516
32. Rajas, F., Gautier, A., Bady, I., Montano, S., and Mithieux, G. (2002) J Biol Chem 277, 15736-15744
33. Elholm, M., Dam, I., Jorgensen, C., Krogsdam, A. M., Holst, D., Kratchmarova, I., Gottlicher, M., Gustafsson, J. A., Berge, R., Flatmark, T., Knudsen, J., Mandrup, S., and Kristiansen, K. (2001) J Biol Chem 276, 21410-21416
34. Murakami, K., Ide, T., Nakazawa, T., Okazaki, T., Mochizuki, T., and Kadowaki, T. (2001) Biochem J 353, 231-238
35. Forman, B. M., Chen, J., and Evans, R. M. (1997) Proc Natl Acad Sci USA 94, 4312-4317
36. Kliewer, S. A., Sundseth, S. S., Jones, S. A., Brown, P. J., Wisely, G. B., Koble, C. S., Devchand, P., Wahli, W., Willson, T. M., Lenhard, J. M., and Lehmann, J. M. (1997) Proc Natl Acad Sci USA 94, 4318-4323
37. Xu, H. E., Lambert, M. H., Montana, V. G., Parks, D. J., Blanchard, S. G., Brown, P. J., Sternbach, D. D., Lehmann, J. M., Wisely, G. B., Willson, T. M., Kliewer, S. A., and Milburn, M. V. (1999) Mol Cell 3, 397-403
38. Hunt, M. C., and Alexson, S. E. (2002) Prog Lipid Res 41, 99-130
39. Gross, R. W. (1983) Biochemistry 22, 5641-5646
40. Nocito, M., Roy, G., Villar, L. M., Palacios, C., Serrano, A., Alvarez-Cermeno, J. C., and Gonzalez-Porque, P. (1996) Biochim Biophys Acta 1299, 17-22
41. Camp, L. A., Verkruyse, L. A., Afendis, S. J., Slaughter, C. A., and Hofmann, S. L. (1994) J Biol Chem 269, 23212-23219
42. Soyombo, A. A., and Hofmann, S. L. (1997) J Biol Chem 272, 27456-27463
43. Duncan, J. A., and Gilman, A. G. (1998) J Biol Chem 273, 15830-15837
44. Hertz, R., Kalderon, B., Byk, T., Berman, I., Za'tara, G., Mayer, R., and Bar-Tana, J. (2005) J Biol Chem 280, 24451-24461
45. Lehman, J. J., Brown, K. A., Ramanadham, S., Turk, J., and Gross, R. W. (1993) J Biol Chem 268, 20713-20716
46. Wolf, M. J., Wang, J., Turk, J., and Gross, R. W. (1997) J Biol Chem 272, 1522-1526
47. Atsumi, G., Tajima, M., Hadano, A., Nakatani, Y., Murakami, M., and Kudo, I. (1998) J Biol Chem 273, 13870-13877
48. Ramanadham, S., Hsu, F. F., Zhang, S., Jin, C., Bohrer, A., Song, H., Bao, S., Ma, Z., and Turk, J. (2004) Biochemistry 43, 918-930
49. Roshak, A. K., Capper, E. A., Stevenson, C., Eichman, C., and Marshall, L. A. (2000) J Biol Chem 275, 35692-35698
50. Su, X., Mancuso, D. J., Bickel, P. E., Jenkins, C. M., and Gross, R. W. (2004) J Biol Chem 279, 21740-21748
51. Ramanadham, S., Song, H., Hsu, F. F., Zhang, S., Crankshaw, M., Grant, G. A., Newgard, C. B., Bao, S., Ma, Z., and Turk, J. (2003) Biochemistry 42, 13929-13940
52. Smani, T., Zakharov, S. I., Leno, E., Csutora, P., Trepakova, E. S., and Bolotina, V. M. (2003) J Biol Chem 278, 11909-11915
53. Smani, T., Zakharov, S. I., Csutora, P., Leno, E., Trepakova, E. S., and Bolotina, V. M. (2004) Nat Cell Biol 6, 113-120
54. Mancuso, D. J., Abendschein, D. R., Jenkins, C. M., Han, X., Saffitz, J. E., Schuessler, R. B., and Gross, R. W. (2003) J Biol Chem 278, 22231-22236
55. Wolf, M. J., and Gross, R. W. (1996) J Biol Chem 271, 20989-20992
56. Jenkins, C. M., Wolf, M. J., Mancuso, D. J., and Gross, R. W. (2001) J Biol Chem 276, 7129-7135
57. Bolotina, V. M. (2004) Sci STKE 2004, pe34
58. Randriamampita, C., and Tsien, R. Y. (1993) Nature 364, 809-814
59. Randriamampita, C., and Tsien, R. Y. (1995) J Biol Chem 270, 29-32
60. Hazen, S. L., and Gross, R. W. (1991) J Biol Chem 266, 14526-14534
61. Hazen, S. L., and Gross, R. W. (1991) Biochem J 280 (Pt 3), 581-587
62. Jenkins, C. M., Han, X., Mancuso, D. J., and Gross, R. W. (2002) J Biol Chem 277, 32807-32814
63. Cohen Simonsen, A., Bernchou Jensen, U., Faergeman, N. J., Knudsen, J., and Mouritsen, O. G. (2003) FEBS Lett 552, 253-258
64. Chao, H., Martin, G. G., Russell, W. K., Waghela, S. D., Russell, D. H., Schroeder, F., and Kier, A. B. (2002) Biochemistry 41, 10540-10553
65. Hazen, S. L., Stuppy, R. J., and Gross, R. W. (1990) J Biol Chem 265, 10622-10630
66. Wessel, D., and Flugge, U. I. (1984) Anal Biochem 138, 141-143
67. Laemmli, U. K. (1970) Nature 227, 680-685
68. Nesterenko, M. V., Tilley, M., and Upton, S. J. (1994) J Biochem Biophys Methods 28, 239-242
69. Gross, R. W. (1984) Biochim Biophys Acta 802, 197-202
70. Hunt, M. C., Solaas, K., Kase, B. F., and Alexson, S. E. (2002) J Biol Chem 277, 1128-1138
71. Hazen, S. L., Zupan, L. A., Weiss, R. H., Getman, D. P., and Gross, R. W. (1991) J Biol Chem 266, 7227-7232
72. Zupan, L. A., Weiss, R. H., Hazen, S. L., Parnas, B. L., Aston, K. W., Lennon, P. J., Getman, D. P., and Gross, R. W. (1993) J Med Chem 36, 95-100
73. O'Brien, P. J., St Jules, R. S., Reddy, T. S., Bazan, N. G., and Zatz, M. (1987) J Biol Chem 262, 5210-5215
74. Duncan, J. A., and Gilman, A. G. (1996) J Biol Chem 271, 23594-23600
75. Tu, Y., Wang, J., and Ross, E. M. (1997) Science 278, 1132-1135
76. Ford, D. A., Horner, C. C., and Gross, R. W. (1998) Biochemistry 37, 11953-11961
77. Schaller, J. (2000) Methods Mol Biol 146, 425-437
78. Quach, T. T., Li, N., Richards, D. P., Zheng, J., Keller, B. O., and Li, L. (2003) J Proteome Res 2, 543-552

79. Zischka, H., Gloeckner, C. J., Klein, C., Willmann, S., Swiatek-de Lange, M., and Ueffing, M. (2004) Proteomics 4, 3776-3782
80. Eichacker, L. A., Granvogl, B., Minis, O., Muller, B. C., Miess, C., and Schleiff, E. (2004) J Biol Chem 279, 50915-50922
81. Nowatzke, W., Ramanadham, S., Ma, Z., Hsu, F. F., Bohrer, A., and Turk, J. (1998) Endocrinology 139, 4073-4085
82. Thomas, D., and Hanley, M. R. (1995) J Biol Chem 270, 6429-6432
83. Han, X., and Gross, R. W. (1994) Proc Natl Acad Sci U S A 91, 10635-10639
84. Wolf, R. A., and Gross, R. W. (1985) J Biol Chem 260, 7295-7303
85. McHowat, J., and Creer, M. H. (1998) Am J Physiol 274, C447-454
86. Murakami, M., Shimbara, S., Kambe, T., Kuwata, H., Winstead, M. V., Tischfield, J. A., and Kudo, I. (1998) J Biol Chem 273, 14411-14423
87. Tessier, C., Hichami, A., and Khan, N. A. (2002) FEBS Lett 520, 111-116
88. Ma, Z., Ramanadham, S., Wohltmann, M., Bohrer, A., Hsu, F. F., and Turk, J. (2001) J Biol Chem 276, 13198-13208
89. Hazen, S. L., Ford, D. A., and Gross, R. W. (1991) J Biol Chem 266, 5629-5633
90. Williams, S. D., and Gottlieb, R. A. (2002) Biochem J 362, 23-32
91. Ma, Z., Ramanadham, S., Kempe, K., Chi, X. S., Ladenson, J., and Turk, J. (1997) J Biol Chem 272, 11118-11127
92. Larsson Forsell, P. K., Kennedy, B. P., and Claesson, H. E. (1999) Eur J Biochem 262, 575-585
93. Larsson, P. K., Claesson, H. E., and Kennedy, B. P. (1998) J Biol Chem 273, 207-214
94. Atsumi, G., Murakami, M., Kojima, K., Hadano, A., Tajima, M., and Kudo, I. (2000) J Biol Chem 275, 18248-18258
95. Lauber, K., Bohn, E., Krober, S. M., Xiao, Y. J., Blumenthal, S. G., Lindemann, R. K., Marini, P., Wiedig, C., Zobywalski, A., Baksh, S., Xu, Y., Autenrieth, I. B., Schulze-Osthoff, K., Belka, C., Stuhler, G., and Wesselborg, S. (2003) Cell 113, 717-730
96. Tay, H. K., and Melendez, A. J. (2004) J Biol Chem 279, 22505-22513
97. Wang, Z., Ramanadham, S., Ma, Z. A., Bao, S., Mancuso, D. J., Gross, R. W., and Turk, J. (2005) J Biol Chem 280, 6840-6849
98. Jenkins, C. M., Han, X., Yang, J., Mancuso, D. J., Sims, H. F., Muslin, A. J., and Gross, R. W. (2003) Biochemistry 42, 11798-11807
99. Lehner, R., and Kuksis, A. (1993) J Biol Chem 268, 24726-24733
100. Liu, G. X., Hanley, P. J., Ray, J., and Daut, J. (2001) Circ Res 88, 918-924
101. Rohacs, T., Lopes, C. M., Jin, T., Ramdya, P. P., Molnar, Z., and Logothetis, D. E. (2003) Proc Natl Acad Sci USA 100, 745-750
102. Mignen, O., Thompson, J. L., and Shuttleworth, T. J. (2003) J Biol Chem 278, 10174-10181
103. Gubitosi-Klug, R. A., Yu, S. P., Choi, D. W., and Gross, R. W. (1995) J Biol Chem 270, 2885-2888
104. Honore, E., Barhanin, J., Attali, B., Lesage, F., and Lazdunski, M. (1994) Proc Natl Acad Sci USA 91, 1937-1941
105. Hamilton, K. L., Syme, C. A., and Devor, D. C. (2003) J Biol Chem 278, 16690-16697
106. Carattino, M. D., Hill, W. G., and Kleyman, T. R. (2003) J Biol Chem 278, 36202-36213
107. Paucek, P., Yarov-Yarovoy, V., Sun, X., and Garlid, K. D. (1996) J Biol Chem 271, 32084-32088
108. Bolotina, V. M., and Csutora, P. (2005) Trends Biochem Sci 30, 378-387
109. Kim, Y. C., Gomez, F. E., Fox, B. G., and Ntambi, J. M. (2000) J Lipid Res 41, 1310-1316
110. Resh, M. D. (1999) Biochim Biophys Acta 1451, 1-16
111. Bijlmakers, M. J., and Marsh, M. (2003) Trends Cell Biol 13, 32-42
112. Smotrys, J. E., and Linder, M. E. (2004) Annu Rev Biochem 73, 559-587
1.1 Lopaschuk, G. D., and Russell, J. C. (1991) Myocardial function and energy substrate metabolism in the insulin-resistant JCR:LA corpulent rat, J. Appl. Physiol. 71, 1302-1308.
2.1 Han, X., Abendschein, D. R., Kelley, J. G., and Gross, R. W. (2000) Diabetes-induced changes in specific lipid molecular species in rat myocardium, Biochem. J. 352, 79-89.
3.1 Kraegen, E. W., Cooney, G. J., Ye, J. M., Thompson, A. L., and Furler, S. M. (2001) The role of lipids in the pathogenesis of muscle insulin resistance and beta cell failure in type II diabetes and obesity, Exp. Clin. Endocrinol. Diabetes 109 Suppl 2, S189-201.
4.1 Finck, B. N., Lehman, J. J., Leone, T. C., Welch, M. J., Bennett, M. J., Kovacs, A., Han, X., Gross, R. W., Kozak, R., Lopaschuk, G. D., and Kelly, D. P. (2002) The cardiac phenotype induced by PPAR overexpression mimics that caused by diabetes mellitus, J, Clin. Invest. 109, 121-130.
5.1 Kelley, D. E. (2002) Skeletal muscle triglycerides: an aspect of regional adiposity and insulin resistance, Ann. N.Y. Acad. Sci. 967, 135-145.
6.1 Unger, R. H. (2002) Lipotoxic diseases, Annu. Rev. Med. 53, 319-336.
7.1 Hung, T., Sievenpiper, J. L., Marchie, A., Kendall, C. W., and Jenkins, D. J. (2003) Fat versus carbohydrate in insulin resistance, obesity, diabetes and cardiovascular disease, Curr Opin Clin Nutr Metab Care 6, 165-176.
8.1 Finck, B. N., Han, X., Courtois, M., Aimond, F., Nerbonne, J. M., Kovacs, A., Gross, R. W., and Kelly, D. P. (2003) A critical role for PPARα-mediated lipotoxicity in the pathogenesis of diabetic cardiomyopathy: modulation by dietary fat content, Proc. Natl. Acad. Sci. U.S.A., 100, 1226-1231.
9.1 Su, X., Han, X., Mancuso, D. J., Abendschein, D. R., and Gross, R. W. (2005) Accumulation of long-chain acylcarnitine and 3-hydroxy acylcarnitine molecular species in diabetic myocardium: identification of alterations in mitochondrial fatty acid processing in diabetic myocardium by shotgun lipidomics, Biochemistry 44, 5234-5245.
10.1 Han, X., and Gross, R. W. (2003) Global analyses of cellular lipidomes directly from crude extracts of biological samples by ESI mass spectrometry: a bridge to lipidomics, J. Lipid Res. 44, 1071-1079.
11.1 Han, X., and Gross, R. W. (2005) Shotgun lipidomics: Electrospray ionization mass spectrometric analysis and quantitation of the cellular lipidomes directly from crude extracts of biological samples, Mass Spectrom. Rev. 24, 367-412.
12.1 Han, X., and Gross, R. W. (2005) Shotgun lipidomics: multi-dimensional mass spectrometric analysis of cellular lipidomes, Expert Rev. Proteomics 2, 253-264.
13.1 Pulfer, M., and Murphy, R. C. (2003) Electrospray mass spectrometry of phospholipids, Mass Spectrom. Rev. 22, 332-364.

14.1 Welti, R., and Wang, X. (2004) Lipid species profiling: a high-throughput approach to identify lipid compositional changes and determine the function of genes involved in lipid metabolism and signaling, Curr. Op/n. Plant Biol. 7, 337-344.

15.1 Forrester Jeffrey, S., Milne Stephen, B., Ivanova Pavlina, T., and Brown, H. A. (2004) Computational Lipidomics: A Multiplexed Analysis of Dynamic Changes in Membrane Lipid Composition during Signal Transduction, Mol. Pharmacol. 65, 813-821.

16.1 Ekroos, K., Chernushevich, I. V., Simons, K., and Shevchenko, A. (2002) Quantitative profiling of phospholipids by multiple precursor ion scanning on a hybrid quadrupole time-of-flight mass spectrometer, Anal. Chem. 74, 941-949.

17.1 Hermansson, M., Uphoff, A., Kakela, R., and Somerharju, P. (2005) Automated quantitative analysis of complex lipidomes by liquid chromatography/mass spectrometry, Anal. Chem. 77, 2166-2175.

18.1 Ishida, M., Yamazaki, T., Houjou, T., Imagawa, M., Harada, A., Inoue, K., and Taguchi, R. (2004) High-resolution analysis by nano-electrospray ionization Fourier transform ion cyclotron resonance mass spectrometry for the identification of molecular species of phospholipids and their oxidized metabolites, Rapid Commun Mass Spectrom. 18, 2486-2494.

19.1 Han, X., Holtzman, D. M., and McKeel, D. W., Jr. (2001) Plasmalogen deficiency in early Alzheimer's disease subjects and in animal models: molecular characterization using electrospray ionization mass spectrometry, J. Neurochem. 77, 1168-1180.

20.1 Han, X., Holtzman, D. M., McKeel, D. W., Jr., Kelley, J., and Morris, J. C. (2002) Substantial sulfatide deficiency and ceramide elevation in very early Alzheimer's disease: potential role in disease pathogenesis, J. Neurochem. 82, 809-818.

21.1 Mancuso, D. J., Abendschein, D. R., Jenkins, C. M., Han, X., Saffitz, J. E., Schuessler, R. B., and Gross, R. W. (2003) Cardiac ischemia activates calcium-independent phospholipase $A_2\beta$, precipitating ventricular tachyarrhythmias in transgenic mice: rescue of the lethal electrophysiologic phenotype by mechanism-based inhibition, J. Biol. Chem. 278, 22231-22236.

22.1 Jam, S., Jayasimhulu, K., and Clark, J. F. (2004) Metabolomic analysis of molecular species of phospholipids from normotensive and preeclamptic human placenta electrospray ionization mass spectrometry, Front. Biosci. 9, 3167-3175.

23.1 Sparagna, G. C., Johnson, C. A., McCune, S. A., Moore, R. L., and Murphy, R. C. (2005) Quantitation of cardiolipin molecular species in spontaneously hypertensive heart failure rats using electrospray ionization mass spectrometry, J. Lipid Res. 46, 1196-1204.

24.1 Vreken, P., Valianpour, F., Nijtmans, L. G., Grivell, L. A., Plecko, B., Wanders, R. J., and Barth, P. G. (2000) Defective remodeling of cardiolipin and phosphatidylglycerol in Barth syndrome, Biochem. Biophys. Res. Commun. 279, 378-382.

25.1 Schlame, M., Towbin, J. A., Heerdt, P. M., Jehle, R., DiMauro, S., and Blanck, T. J. (2002) Deficiency of tetralinoleoyl-cardiolipin in Barth syndrome, Ann. Neurol. 51, 634-637.

26.1 Valianpour, F., Wanders, R. J., Overmars, H., Vreken, P., Van Gennip, A. H., Baas, F., Plecko, B., Santer, R., Becker, K., and Barth, P. G. (2002) Cardiolipin deficiency in Xlinked cardioskeletal myopathy and neutropenia (Barth syndrome, MIM 302060): a study in cultured skin fibroblasts, J. Pediatr. 141, 729-733.

27.1 Barth, P. G., Valianpour, F., Bowen, V. M., Lam, J., Duran, M., Vaz, F. M., and Wanders, R. J. (2004) X-linked cardioskeletal myopathy and neutropenia (Barth syndrome): an update, Am J Med Genet A 126, 349-354.

28.1 Gu, Z., Valianpour, F., Chen, S., Vaz, F. M., Hakkaart, G. A., Wanders, R. J., and Greenberg, M. L. (2004) Aberrant cardiolipin metabolism in the yeast tazl mutant: a model for Barth syndrome, Mol. Microbiol. 51, 149-158.

29.1 Han, X., Yang, J., Cheng, H., Ye, H., and Gross, R. W. (2004) Towards fingerprinting cellular lipidomes directly from biological samples by two-dimensional electrospray ionization mass spectrometry, Anal. Biochem. 330, 317-331.

30.1 Bligh, E. C., and Dyer, W. J. (1959) A rapid method of total lipid extraction and purification, Can. J. Biochem. Physiol. 37, 911-917.

31.1 Le Belle, J. F., Harris, N. G., Williams, S. R., and Bhakoo, K. K. (2002) A comparison of cell and tissue extraction techniques using high-resolution 1H-NMR spectroscopy, NMR Biomed. 15, 37-44.

32.1 Gibon, Y., Vigeolas, H., Tiessen, A., Geigenberger, P., and Stitt, M. (2002) Sensitive and high throughput metabolite assays for inorganic pyrophosphate, ADPGlc, nucleotide phosphates, and glycolytic intermediates based on a novel enzymic cycling system, Plant J. 30, 221-235.

33.1 Schlame, M., and Haldar, D. (1993) Cardiolipin is synthesized on the matrix side of the inner membrane in rat liver mitochondria, J Biol. Chem. 268, 74-79.

34.1 Mandieau, V., Martin, I., and Ruysschaert, J. M. (1995) Interaction between cardiolipin and the mitochondrial presequence of cytochrome c oxidase subunit IV favours lipid mixing without destabilizing the bilayer structure, FEBS Lett. 368, 15-18.

35.1 Zhang, M., Mileykovskaya, E., and Dowhan, W. (2002) Gluing the respiratory chain together. Cardiolipin is required for supercomplex formation in the inner mitochondrial membrane, J. Biol. Chem. 277, 43553-43556.

36.1 Pfeiffer, K., Gohil, V., Stuart, R. A., Hunte, C., Brandt, U., Greenberg, M. L., and Schagger, H. (2003) Cardiolipin stabilizes respiratory chain supercomplexes, J. Biol. Chem. 278, 52873-52880.

37.1 McMillin, J. B., and Dowhan, W. (2002) Cardiolipin and apoptosis, Biochim. Biophys. Acta 1585, 97-107.

38.1 Degli Esposti, M. (2004) Mitochondria in apoptosis: past, present and future, Biochem. Soc. Trans. 32, 493-495.

39.1 Ostrander, D. B., Sparagna, C. C., Amoscato, A. A., McMillin, J. B., and Dowhan, W. (2001) Decreased cardiolipin synthesis corresponds with eytoehrome c release in palmitate-induced cardiomyocytc apoptosis, J. Biol. Chem. 276, 38061-38067.

40.1 Ortiz, A., Killian, J. A., Verkleij, A. J., and Wilschut, J. (1999) Membrane fusion and the lamellar-to-inverted-hexagonal phase transition in cardiolipin vesicle systems induced by divalent cations, Biophys. 1. 77, 2003-2014.

41.1 Bossy-Wetzel, F., Barsoum, M. J., Godzik, A., Schwarzenbacher, R., and Lipton, S. A. (2003) Mitochondrial fission in apoptosis, neurodegeneration and aging, Curr. Opin. Cell Biol. 15, 706-716.

42.1 Xu, Y., Kelley, R. I., Blanek, T. J., and Schlame, M. (2003) Remodeling of cardiolipin by phospholipid transacylation, J. Biol. Chem. 278, 51380-51385.

43.1 Vaz, F. M., Houtkooper, R. H., Valianpour, F., Barth, P. G., and Wanders, R. J. (2003) Only one splice variant of the human TAZ gene encodes a functional protein with a role in cardiolipin metabolism, J. Biol. Chem. 278, 43089-43094.
44.1 Lopaschuk, G. D., Tahiliani, A. G., Vadlamudi, R. V., Katz, S., and McNeill, J. H. (1983) Cardiac sarcoplasmic reticulum function in insulin- or carnitine-treated diabetic rats, Am. J. Physiol. 245, H969-976.
45.1 Katz, F. B., Stenbit, A. E., Hatton, K., DePinho, R., and Charron, M. J. (1995) Cardiac and adipose tissue abnormalities but not diabetes in mice deficient in GLUT4, Nature 377, 151-155.
46.1 Stenbit, A. F., Tsao, T. S., Li, J., Burcelin, R., Geenen, D. L., Factor, S. M., Houseknecht, K., Katz, F. B., and Charron, M. J. (1997) GLUT4 heterozygous knockout mice develop muscle insulin resistance and diabetes, Nat. Med. 3, 1096-1101.
47.1 Dhalla, N. S., Liu, X., Panagia, V., and Takeda, N. (1998) Subcellular remodeling and heart dysfunction in chronic diabetes, Cardiovasc. Res. 40, 239-247.
48.1 Godin, D. V., Lopaschuk, G. D., and McNeill, J. H. (1986) Subcellular myocardial abnormalities in experimental diabetes: role of long-chain acylcarnitines, Can. J. Cardiol. 2, 222-229.
49.1 Valianpour, F., Wanders, R. J., Overmars, H., Vaz, F. M., Barth, P. G., and van Gennip, A. H. (2003) Linoleic acid supplementation of Barth syndrome fibroblasts restores cardiolipin levels: implications for treatment, J. Lipid Res. 44, 560-566.
50.1 Broekemeier, K. M., Iben, J. R., LeVan, E. G., Crouser, E. D., and Pfeiffer, D. R. (2002) Pore formation and uncoupling initiate a Ca2+-independent degradation of mitochondrial phospholipids, Biochemistry 41, 7771-7780.
51.1 Han, X., and Gross, R. W. (1990) Plasmenylcholine and phosphatidylcholine membrane bilayers possess distinct conformational motifs, Biochemistry 29, 4992-4996.

While the invention has been described in terms of various specific embodiments, those skilled in the art will recognize that the invention can be practiced with modification within the spirit and scope of the claims.

What is claimed is:

1. An in vitro screening method for identifying a compound with iPLA$_2$β modulating activity, the method comprising:
   a) providing a preparation of iPLA$_2$β in vitro;
   b) inhibiting iPLA$_2$β by adding calcium activated calmodulin to the preparation;
   c) adding the compound to be screened to the preparation;
   d) adding an acyl-CoA to the preparation; and
   e) determining iPLA$_2$β activity.

2. The method of claim 1, wherein failure of added acyl-CoA to activate iPLA$_2$β indicates that the compound is an iPLA$_2$β inhibitor.

3. The method of claim 1 wherein said method is a high throughput screening assay.

4. The method of claim 1, wherein the determining step is by measuring hydrolysis of added acyl-CoA.

5. The method of claim 1, wherein the acyl-CoA is palmitoyl-CoA and the determining step is by measuring hydrolysis of palmitoyl-CoA.

6. The method of claim 1, wherein the iPLA$_2$β is a purified recombinant iPLA$_2$β.

7. The method of claim 1, wherein the preparation of iPLA$_2$β comprises a cell culture wherein the cells overexpress iPLA$_2$β.

8. The method of claim 7, wherein the cells comprise an expression vector encoding iPLA$_2$β.

* * * * *